(12) United States Patent
Graham et al.

(10) Patent No.: US 8,772,256 B2
(45) Date of Patent: Jul. 8, 2014

(54) CODON MODIFIED IMMUNOGENIC COMPOSITIONS AND METHODS OF USE

(75) Inventors: Barney S. Graham, Rockville, MD (US); Teresa R. Johnson, Gaithersburg, MD (US)

(73) Assignee: The United States of America as represented by the Secretary, Department of Health and Human Services, Rockville, MD (US)

( * ) Notice: Subject to any disclaimer, the term of this patent is extended or adjusted under 35 U.S.C. 154(b) by 909 days.

(21) Appl. No.: 12/517,194

(22) PCT Filed: Nov. 30, 2007

(86) PCT No.: PCT/US2007/024625
§ 371 (c)(1),
(2), (4) Date: Jun. 2, 2010

(87) PCT Pub. No.: WO2008/133663
PCT Pub. Date: Nov. 6, 2008

(65) Prior Publication Data
US 2010/0247621 A1    Sep. 30, 2010

Related U.S. Application Data

(60) Provisional application No. 60/872,071, filed on Nov. 30, 2006.

(51) Int. Cl.
| | |
|---|---|
| *A61K 48/00* | (2006.01) |
| *C07H 21/04* | (2006.01) |
| *C12N 15/85* | (2006.01) |
| *C12N 5/10* | (2006.01) |

(52) U.S. Cl.
USPC ... 514/44 R; 435/320.1; 435/325; 536/23.72; 424/199.1

(58) Field of Classification Search
USPC .......... 514/44 R; 435/320.1, 325; 536/23.72; 424/199.1
See application file for complete search history.

(56) References Cited

PUBLICATIONS

Li et al. (1998) J. Exp. Med., vol. 188(4), 681-688.*
Ramakrishna et al. (2004) J. Virol., vol. 78(17), 9174-9189.*
Haas et al. (1996) Current Biol., vol. 6(3), 315-324.*
Bembridge et al. (1998) J Virol., vol. 72(5):4080-4087.*

* cited by examiner

*Primary Examiner* — Anne Marie S Wehbe
(74) *Attorney, Agent, or Firm* — Edwards Wildman Palmer LLP; Peter F. Corless

(57) ABSTRACT

The present invention features immunogenic compositions comprising codon modified genes that encode viral proteins and/or glycoproteins or fragments. The immunogenic compositions of the invention are useful in various methods of treatment, such as preventing or treating viral infection. Also provided in the present invention are kits and instructions for use.

17 Claims, 57 Drawing Sheets

Figure 4

Codon Modification of RSV M-M2 Fusion

Motif alterations

- Procarya inhibitory motifs — None
- AT-rich or GC-rich sequences stretches — 8 → 0
- poly(A) sites — 12 → 0
- Consensus (cryptic) splice donor site — 6 → 0
- RNA instability motif (ARE) — 6 → 0

*Codon Quality Plot* (non-optimized vs GeneOptimizer-optimized)

Fig. 2a / Fig. 2b — The plots show the quality of the used codon at the indicated codon position.

*GC content*

Fig. 3a — Average GC content: 36%
Fig. 3b — Average GC content: 52%

The plots show the GC content in a 40bp window centered at the indicated nucleotide position.

Figure 5c Weight Loss and Virus Replication After RSV Challenge
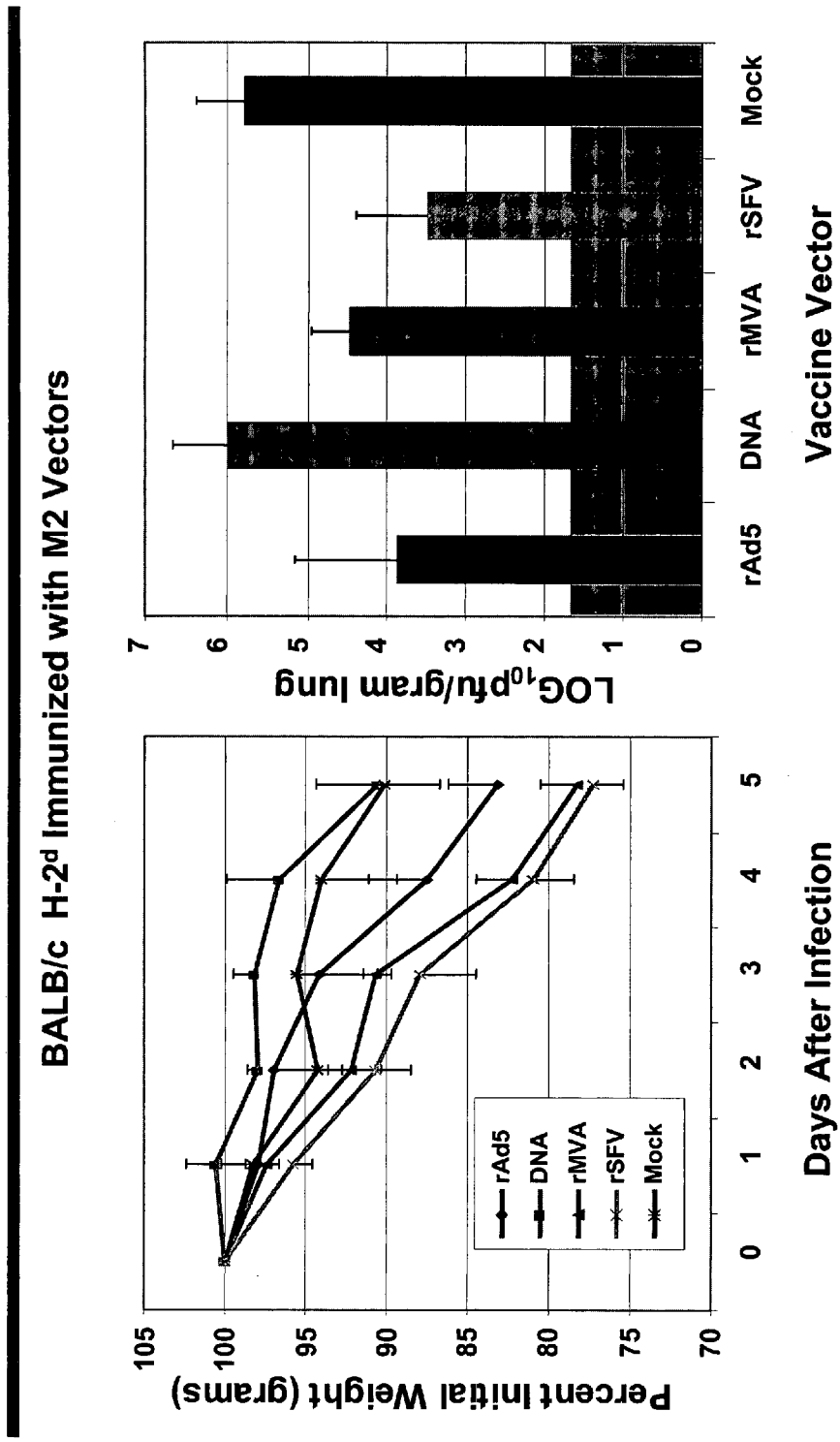

Cytokine Production in Lung Day 5 Post RSV Challenge

M2 or M-Specific Responses in Spleen Prior to Challenge

Figure 12a

Cytotoxic T Cell Activity in Lung

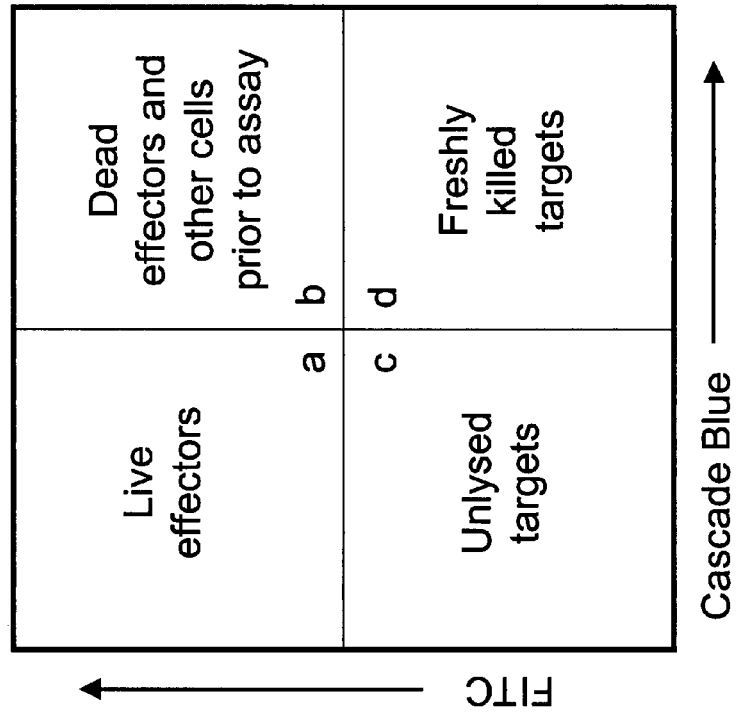

Lung mononuclear cells isolated by Ficoll or CD8+ T cells isolated with magnetic beads labeled with CFSE P815 H-$2^d$ targets pulsed with M2 peptide and EL-4 H-$2^b$ targets pulsed with M peptide. Labeled with Annexin V-FITC 3 hour incubation at effector:target ~20:1 for mononuclear cells or ~2:1 ratio for CD8+ T cells Label with Annexin-V-Cascade blue % Specific Cytotoxicity = d/(c+d) X 100

Weight Loss and Virus Replication After RSV Challenge

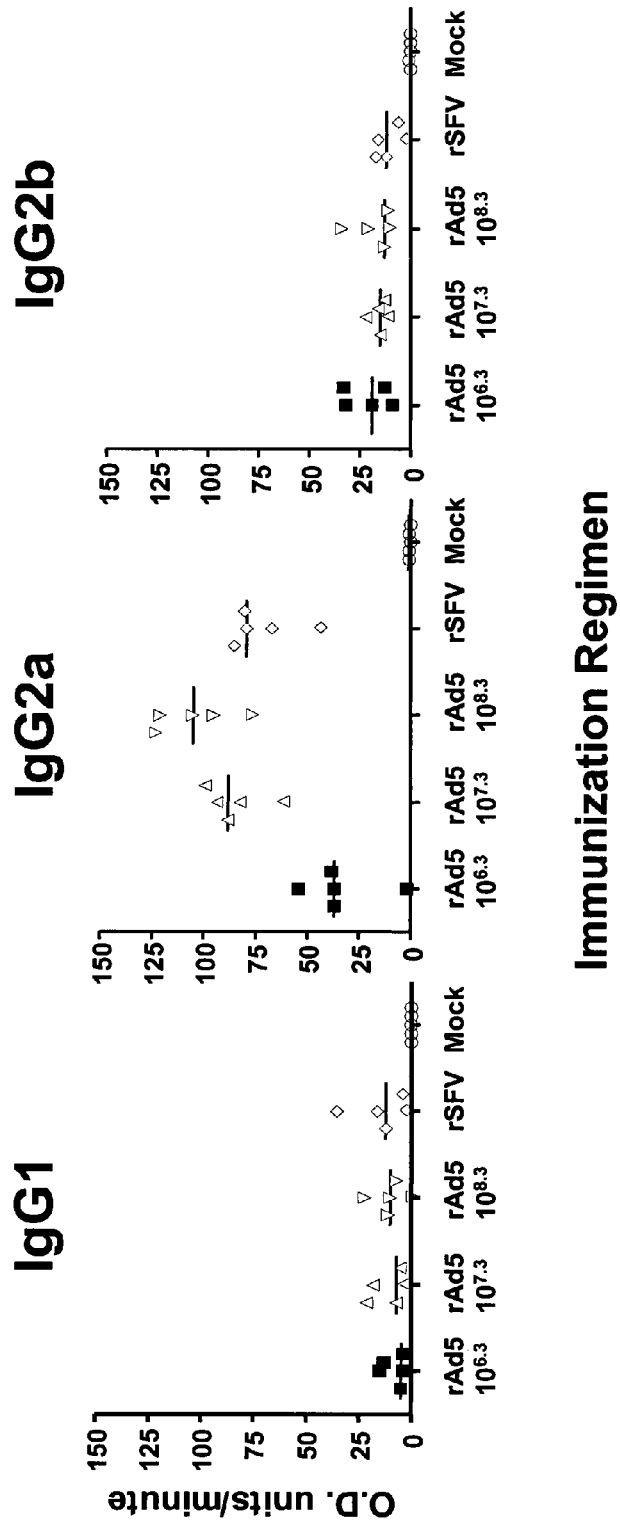
Figure 16a M/M2-Specific Antibody Response by Kinetic ELISA

Cytokine Production in Lung Day 5 Post RSV Challenge

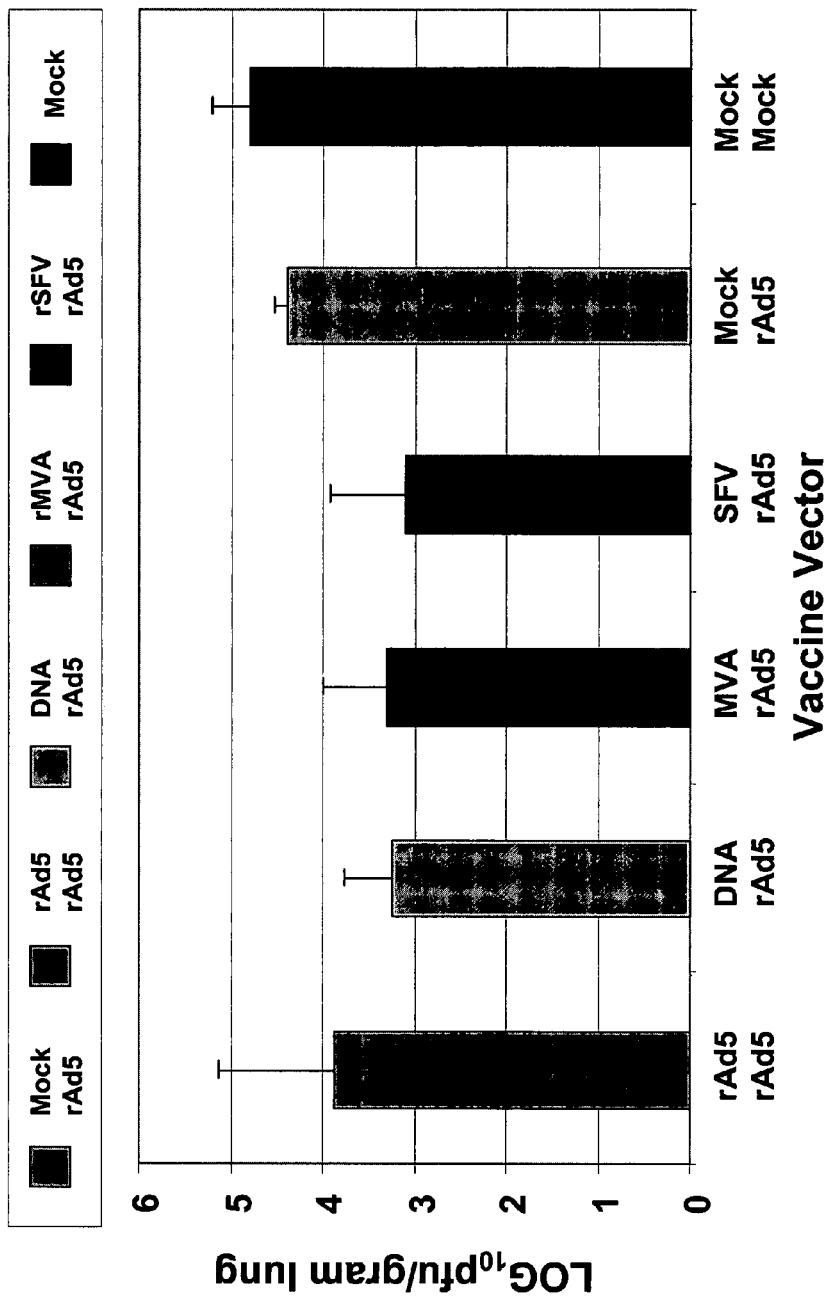
Figure 21a Virus Replication in Mice Immunized with Heterologous Vectors

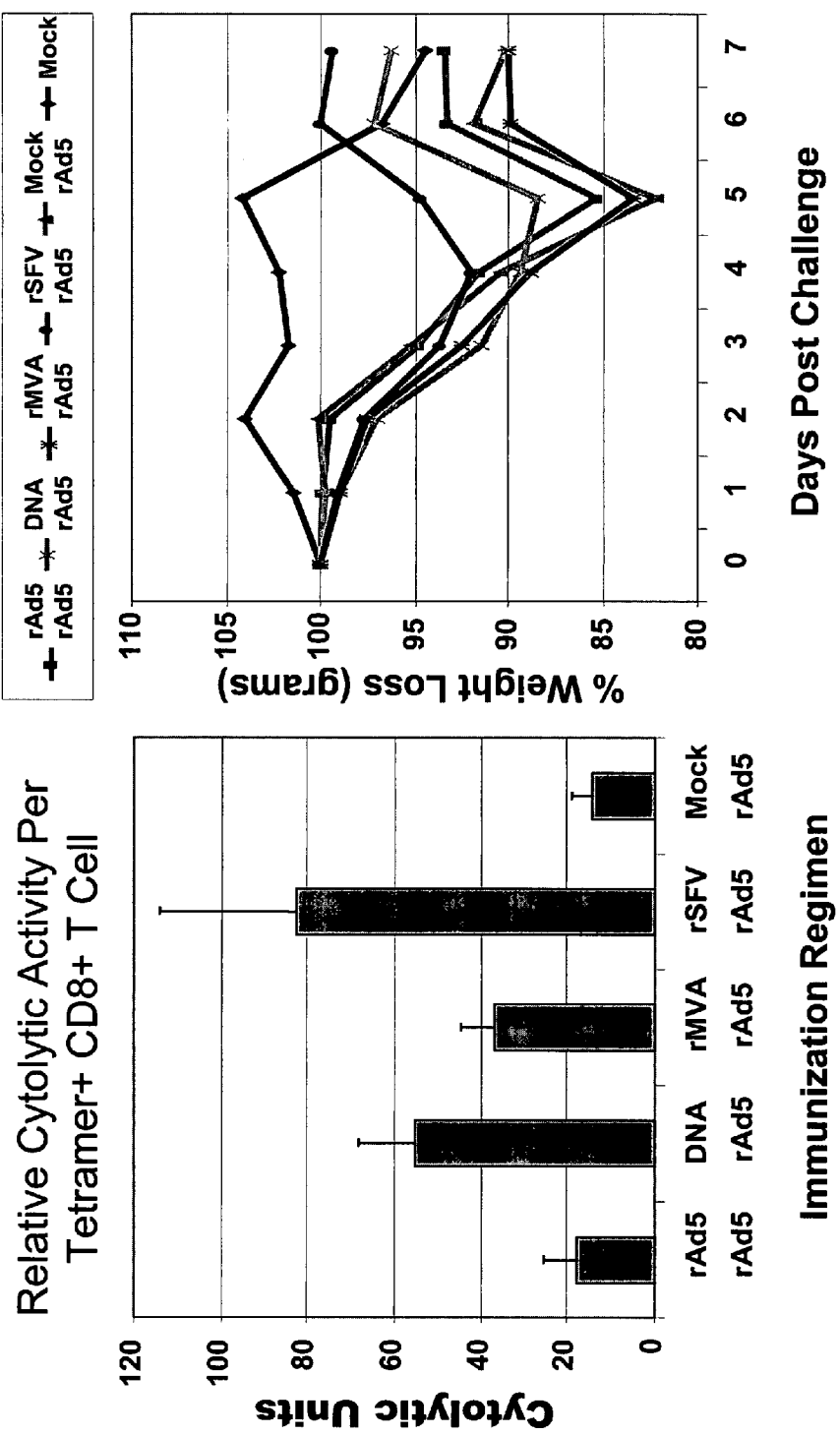
Figure 23 Correlation of CTL Efficiency with Reduced Illness

Weight Loss in Mice Serially Immunized with Heterologous Vectors

Phenotype of Tetramer-Positive CD8+ T Cells After Heterologous Boosting

Figure 28

SEQ ID NO: 1

MSKNKDQRTAKTLERTWDTLNHLLFISSCLYKLNLKSVAQITLSILAMIISTSLIIAAIIFIASANHKVTPTT
AIIQDATSQIKNTTPTYLTQNPQLGISPSNPSEITSQITTILASTTPGVKSTLQSTTVKTKNTTTQTQPS
KPTTKQRQNKPPSKPNNDFHFEVFNFVPCSICSNNPTCWAICKRIPNKKPGKKTTTKPTKKPTLKTTK
KDPKPQTTKSKEVPTTKPTEEPTINTTKTNIITTLLTSNTTGNPELTSQMETFHSTSSEGNPSP
SQVSTTSEYPSQPSSPPNTPRQ

SEQ ID NO: 2

ATGAGCAAGAACAAGGACCAGCGGACCGCCAAGACCCTGGAGAGAACCTGGGACACCCTGAACCACCTGC
TGTTCATCAGCAGCTGCCTGTACAAGCTGAACCTGAACAAGAGCGTGGCCCAGATCACCCTGTCTATCCTGGCC
ATGATCATCAGCACCAGCCTGATCATCGCCGCCATCATCTTCATCGCCAGCGCCAACCACAAGGTGACCCC
CACCACAGCCATCATCCAGGACGCCACCTCCCAGATCAAGAACACCACCCCCACCTACCTGACCCAGAACC
CTCAGCTGGGCATCAGCCCTAGCAACCCCAGCGAGATCACCTCTCAGATCACCACCATCCTGGCCTCTACC
ACCCCTGGCGTGAAGTCTACCCTGCAGAGCACCACCGTCAAGACAAAGAACACCACCACCCAGACCCC
AGCCTAGCAAGCCTACCACCAAGCAGAGGCAGAACAAGCCTCCCAGCAAGCCTAACAACGACTTCCACTTT
GAAGTGTTCAACTTCGTGCCCTGCAGCATCTGCAGCAACAACCCTACCTGCTGGGCCATCTGCAAGCGCAT
CCCCAACAAGAAGCCCGGCAAGAAAACCACCACAAAGACCAAGGAAGTGCCCACACCCTGGACCCTGACCCGGACCCTGAGCCCACCA
AGGACCCCAAGCCCCAGACCAACATCATCACCACCACCAGGAAGCCTGTGACCCTCTAACACCACCGGCAACCCTGAGCTGACC
TCAACACGACAGACCTTCCACAGCACCTCTAGCGAGGGCAACCCTAGCCCCTAGCCCTAGCCAACCCTAGCCAACCCTCGAGCTGACC
AGCCAGATGGAGACCTTCCACAGCACCTCTAGCGAGGGCAACCCTAGCCCCTAGCCAGCCAAGTGAGCACCACCT
CTGAGTACCCCTAGCCAGCCTCTCCTCCTAATACCCCCTCGGCAGTG

Figure 29

SEQ ID NO: 3

METYVNKLHEGSTYTAAVQYNVLEKDDDPASLTIWVPMFQSSMPADLLIKELANVNILVKQISTPKGPSLRV
MINSRSAVLAQMPSKFTICANVSLDERSKLAYDVTTPCEIKACSLTCLKSKNMLTTVKDLTMKTLNPTHDIIA
LCEFENIVTSKKVIIPTYLRSISVRNKDLNTLENITTEFKNAITNAKIIPYSGLLLVITVTDNKGAFKYIKPQSQF
IVDLGAYLEKESIYYVTTNWKHTATRFAIKPMED

SEQ ID NO: 4

ATGGAGACCTACGTGAATAAGCTGCACGAGGGAAGCACCTACACCGCGCTGTGCAGTACAATGTGC
TGGAGAAGGACGATGATCCTGCTTCCCTGACCATCTGGGTGCCCATGTTCAGTCTAGCATGCCCGC
CGATCTGCTGATTAAGGAGCTGGCCAACGTGAACATCCTGGTGAAGCAGATCAGCACCCCAAGGGA
CCTTCCCTGAGAGTGTGATGATTAACTCCAGAGAGATCCAGAAGTCCAAGATGTGACCCTAAGTTCACAA
TCTGCGCTAATGTGTCCCTGGACGAGAGATCTGAAGTCCAAGAATGCTGACCACCGTGAAGGACCTGACAATGA
CAAGGCTTGTTCTGCAGCGATATCATCGCCCTGTGTGAGTTTGAGAATATCGTGACAAGCAAGAAG
AAACACTGAATCCCACCACGAGTTTAAGAACGCTATCACAAACGCCAAGATCATCCCTTACAGCGGACTGCTGCTG
GTCATCACAGTGACCGATAACAAGGGCGCCTTCAAGTACATCAAGCCACAGTCCCAGTTCATCGTGG
ATCTGGGCGCTTACCTGGAGAAGGAGAGCATCTACTACGTGACCACCAACTGGAAGCACACCAGCTAC
AAGATTCGCCATCAAGCCCATGGAGGAC

Figure 30

SEQ ID NO: 5

MSRRNPCKFEIRGHCLNGKRCHFSHNYFEWPPHALLVRQNFMLNRILKSMDKSIDTLSEISGAAELDRT
EEYALGVVGVLESYIGSINNITKQSACVAMSKLLTELNSDDIKKLRDNEELNSPKIRVYNTVISYIESNRKN
NKQTIHLLKRLPADVLKKTIKNTLDIHKSITINNPKESTVSDTNDHAKNNDTT

SEQ ID NO: 6

ATGAGCCGGCGGAATCCATGTAAGTTCGAGATCAGAGGCCACTGCCTGAATGGAAAGAGATGCCACTT
CAGCCACAACTACTTCGAGTGGCCCCCACACGCTCTGCTGGTGAGACAGAATTTCATGCTGAACCGCA
TCCTGAAGAGCATGGATAAGAGCATCGACACACTGAGCGAGATCTCTGGCGCTGCCGAGCTGGATCG
GACAGAGGAGTACGCCCTGGGAGTGGTGGGAGTGCTGGAGAGCTACATCGGCTCCATCAATAACATC
ACCAAGCAGAGCGCCTGCGTGGCTATGAGCAAGCTGCTGACCGAGTGTACAATACAGTGATCTCTTACATC
AGCTGAGAGACAACGAGGAGCTGAACAGCCAAAGATCAGAGTGTACAATACAGTGATCTCTTACATC
GAGAGCAATAGGAAGAACAACAAGCAGACATCCACCTGCTGAAGAGACTGCCCGCTGATGTGCTGA
AGAAACCATCAAGAATACACTGGACATCCACAAGTCTATCACAATCAACAATCCTAAGGAGAGCACAG
TGAGCGATACAAACGACCACGCTAAGAATAATGATAC

FIG. 31A

SEQ ID NO: 7

ATGAGCAAGAAGAACAAGGACCAGGACCGGCCAAGACCCTGGAGAGAACCTGGGACACCCTGAACCACCTGC
TGTTCATCAGCAGCTGCCTGTACAAGCTGAACCTGAAGAGCGTGGCCCAGATCACCCTGTCTATCCTGGCC
ATCATCAGCACCAGCCTGATCATCGCCGCCATCTTCATCGCCAGCGCCAACCACACAAAGTGACCCC
CACCACAGCCATCATCCAGGACGCCACCTCCCAGCAACCCCAGCACCACCCCACCTACTGACCCAGAACC
CTCAGCTGGGCATCAGCAGCCTAGCAGCCAGCAGCACCACCGTCAGATCACCACCATCCTGGCCTCTACC
ACCCCTGGGCGTGAAGTCTACCCTGCAGAGACCAAGCCAAGAACACGACCACCACACAGACCC
AGCCTAGCAAGCCTACCACCACAAGCAGAGGCAGAACAAGCCTCCCAGCAAGCCCAACAACGACTTCCACTTT
GAAGTGTTCAACTTCGTGCCCTGCCCTGCAGCATCTGCAGCAACCTACCCTGCTGGGCCATCTGCAAGGCAT
CCCAACAAGAAGCCCGGCAAGAACCACAAGAAAACCACCAAGAAGAGCCTACCCTCAAGACCACCAAG
AAGGACCCCAAGCCAAGACCACAACATCATCACCACCCTGCTGACCTCTAACACCACCACCGGCAACCCACCA
TCAACACGACCAAGACCAACATCATCACCACCCTGCTGACCCTCTAACACCACCACCGGCAACCCTGAGCTGACC
AGCCAGATGGAGACCTTCCACAGCCCCAGCAACCCCTAGCGGCAACCCCTAGCCCTAGCCAAGTGAGCACCCACCT
CTGAGTACCCCTAGCCCAGCAGCCCAGCTCTCCTCCTAATACCCCCTCGGGCAGTGAGGAT

FIG. 31B

SEQ ID NO: 8

ATGGAGACCTACGTGAATAAGCTGCACGAGGAAGCACCTACACCGCCGCTGTGCAGTACAATGTGC
TGGAGAAGGACGATGATCCTCCTTCCCTGACCATCTGGGTGCCCATGTTTCAGTCTAGCATGCCCGC
CGATCTGCTGATTAAGGAGCTGGCCAACATCCTGGTGAAGCAGATCAGCAGCACCCAAAGGGA
CCTTCCCTGAGAGTGATGATTAACTCCAGAGAGATCCAGATGCCCTCTAAGTTCACAA
TCTGCGCTAATGTGTCCCTGGACGAGATCTCAAGCTGGCTTACGATGTGACCACCCATGCGAGAT
CAAGGCTTGTTCTCTGACCTGTCTGAAGTCTCCAAGAATATGCTGACCACCGTGAAGGACCTGACAATGA
AAACACTGAATCCCAACACTGAATCATCGCCCTGTGTGAGTTTGAGAATATCGTGACAAGCAAGAAG
GTCATCATCAGTCGAGTTTAAGAACGCTATCTCTGTGAGGAATAAGGATCTGAACACACTGGACTGCTG
CACAACCACCGAGTTTAAGAACGCTATCAACAAGCCAAGATCATCCCTTACAGCGGACTGCTG
GTCATCACAGTGACCGATAACAAGGGCGCCTTCAAGTACATACAAGCCACACAGTCCCAGTTCATCGTGG
ATCTGGGCGCTTACCTGGAGAAGGAGCATCTACTACGTGACCACCAACTGGAAGCACACAGCTAC
AAGATTCGCCATCAAGCCCATGGAGGACCCTGATCAGGCTATGTCTAGGCGCAACCCTTGCAAGTTT
GAGATCCGGGACACTGTCTGAACGGCAAGCGGTGTCACTTTTCTCACAATTACTTTGAGTGGCCTC
CTCACGCCCTGGTGGCGGCAAGAACTTTATGCTGAATGAATCCTGAAGTCTATGGACAAGTCTATC
GATACCCTGTCCGAGATCTCCGAGCTGAGCTGAGCTGGACAGAACCGAGGAGTACGCTCTGGGCGTG
GTGGGCGTGGAGTCTTACATCGGCAGCATCAACAATCACAAGCAGTCCGCCTTGTGTGGCCA
TGTCTAAGCTGCTGAGAGATCTGAACTCTGACGATATCAAGAAGCTGCGGGATAACGAGGAGCTGAA
TTCCCCTAAGATCCACTCTGCTGAAGCGGCTGCCGACGTGCTGAAGAAAACAATCAAGAACACCCTGGA
AGACAATCCACCTGCTGAAGCGGCTGCCGACGTGCTGAAGAAACAATCAAGAACACCCTGGA
TATCCACAAGAGCATCACCATCAATAACCCCAAGGAGTCTACCGTGTCCGACACAAACGATCACGCCA
AGAACAACGACACAA

Figure 32

SEQ ID NO: 9

MALSKVKLNDTLNKDQLLSSSKYTIQRSTGDSIDTPNYDVQKHINKLCGMLLITEDANHKFTGLIGMLYA
MSRLGREDTIKILRDAGYHVKANGVDVTTHRQDINGKEMKFEVLTLASLTTEIQINIEIESRKSYKKMLKE
MGEVAPEYRHDSPDCGMIILCIAALVITKLAAGDRSGLTAVIRRANNVLKNEMKRYKGLLPKDIANSFYE
VFEKHPHFIDVFVHFGIAQSSTRGGSRVEGIFAGLFMNAYGAGQVMLRWGVLAKSVKNIMLGHASVQA
EMEQVVEVYEYAQKLGEEAGFYHILNNPKASLLSLTQFPHFSSVVLGNAAGLGIMGEYRGTPRNQDLY
DAAKAYAEQLKENGVINYSVLDLTAEELEAIKHQLNPKDNDVEL

SEQ ID NO: 10

ATGGCCCTGAGCAAGGTCAAGCTGAACGACACCCTGAACAAGGACCAGCTGCTGTCCAGCAGCAAGTAC
ACCATCCAGAGAAGCACCGGCGATCACCGGCGATGATCACCGGCGACATCTACGACGTGCAGAAGCACATCAACAAG
CTGTGCGGCATGCTGCTGATCACCGAGGACGCCAACCACAAGTTCACCGGCCTGATCGGCATGCTGTAC
GCCATGAGCAGGCTGGGCCGAGAGGACACCATCAAGATCCTGAGGGACGCCGGCTACCACGTGAAGGC
CAACGGCGTGGACGTGACCACCCACAGGCAGGACATCAACGGCAAGGAGAACAAGTTCGAGGTCCTGA
CCCTGGCCAGCCTGACCACCGAGATCCAGATCAACATCGAGATCGAGAGCAGCCCCGACTGCGCATGATCATC
CTGTCATCGCCGCCTGGTCATCACCAAGCTGCTGCCGGCGACAAGAGGGCCTGCTGCCCAAGGACATCG
CAGACGGCCAACACGTGCTGAAGAACGAGATGAAGAGGTACAAGGGCCATCTTCATGACGTTCGGCATCG
CCAACAGCTTCTACGAGGTGTTCGAGAAGCACCCCACTTCATCGACGTCTTCGCCGGCATCGCCCAGAG
CTCCAGAGCAGCAGGGGCGACCAGGGTCATGCCGAGATGGGCGAGGTGCTGCGCAGCGTGAAGACATCGCTGGGCCA
GGAGCCGGCCAGTCATGTCGAGGCCGAGATGGAACAGGTGGAGGTGTACGAGTACGCCCAGAAGCTGGGCGGC
CGCCAGCGTGCAGGCCAGATACCACATCTGAACAACCCCAAGGCCTCCCTGCTGTCCCTGACCCAGTTCCCCCAC
GAGGCCGGCAGATACCACATCTGGGCAATGCCGCCAAGGCCTACGCCGAGCAGCTGAAGGAGAACGGCGTCATCAACT
ACAGCGTGCTGGATCTGACCGCCGAGGAACTGGAAGCCATCAAGCACCAGCTGAACCCCAAGGACAAC
GACGTGGAGCTGTGATGAGGATCCGAGCTC

Figure 33

SEQ ID NO: 11

MENTSITIEFSSKFWPYFTLIHMITTIISLLIIISIMIAILNKLCEYNVFHNKTFELPRARVNT

SEQ ID NO: 12

ATGGAAAACACCAGCATCACCATCGAGTTCAGCAGCAAGTTCTGGCCCTACTTCACCCTGATCCACATGATC
ACCACCATCATCAGCCTGCTGATCATCATCAGCATCATGATCGCCATCCTGAACAAGCTGTGCGAGTACAAC
GTGTTCCACAACAAGACCTTCGAGCTGCCCAGGGCCAGGGTGAACACCT

FIG. 34A

SEQ ID NO: 13

MELLILKANAITTILTAVTFCFASGQNITEEFYQSTCSAVSKGYLSALRTGWYTSVITIELSNIKENKC
NGTDAKVKLIKQELDKYKNAVTELQLLMQSTPPTNNRARRELPRFMNYTLNNAKKTNVTLSKKRK
RRFLGFLLGVGSAIASGVAVSKVLHLEGEVNKIKSALLSTNKAVVSLSNGVSVLTSKVLDLKNYIDK
QLLPIVNKQSCSISNIETVIEFQQKNNRLLEITREFSVNAGVTTPVSTYMLTNSELLSLINDMPITNDQ
KKLMSNNVQIVRQQSYSIMSIIKEEVLAYVVQLPLYGVIDTPCWKLHTSPLCTTNTKEGSNICLTRTD
RGWYCDNAGSVSFFPQAETCKVQSNRVFCDTMNSLTLPSEINLCNVDIFNPKYDCKIMTSKTDVS
SSVITSLGAIVSCYGKTKCTASNKNRGIIKTFSNGCDYVSNKGMDTVSVGNTLYVVNKQEGKSLYV
KGEPIINFYDPLVFPSDEFDASISQVNEKINQSLAFIRKSDELLHNVNAGKSTTNIMITTIIVIVILLSLI
AVGLLLYCKARSTPVTLSKDQLSGINNIAFSN

SEQ ID NO: 16 - New F sequence

MELLILKANAITTILTAVTFCFASGQNITEEFYQSTCSAVSKGYLSALRTGWYTSVITIELSNIKENKC
NGTDAKVKLIKQELDKYKNAVTELQLLMQSTPATNNRARRELPRFMNYTLNNAKKTNVTLSKKRK
RRFLGFLLGVGSAIASGVAVSKVLHLEGEVNKIKSALLSTNKAVVSLSNGVSVLTSKVLDLKNYIDK
QLLPIVNKQSCSISNIETVIEFQQKNNRLLEITREFSVNAGVTTPVSTYMLTNSELLSLINDMPITNDQ
KKLMSNNVQIVRQQSYSIMSIIKEEVLAYVVQLPLYGVIDTPCWKLHTSPLCTTNTKEGSNICLTRTD
RGWYCDNAGSVSFFPQAETCKVQSNRVFCDTMNSLTLPSEVNLCNVDIFNPKYDCKIMTSKTDVS
SSVITSLGAIVSCYGKTKCTASNKNRGIIKTFSNGCDYVSNKGVDTVSVGNTLYVVNKQEGKSLYV
KGEPIINFYDPLVFPSDEFDASISQVNEKINQSLAFIRKSDELLHNVNAGKSTTNIMITTIIVIVILLSLI
AVGLLLYCKARSTPVTLSKDQLSGINNIAFSN**

FIG. 34B

SEQ ID NO: 14

ATGGAGCTGCTGATCCTGAAGGCCAACGCCATCACCACCATCCTGACCGCCGTGACCTTCTGCTT
CGCCAGCGCCCAGAATATCACCGAGGAGTTCTACCAGAGCACCTGTAGCGCCGTGTCCAAGGGC
TACCTGAGCGCCCTGAGAACCGGCTGGTACACCGCCAAGTTGATCACCATCGAGCTGTCCAACATCAA
GGAAAACAAGTGTAACGGCACCGACGCCAAGGTGAAGCTGATCAAGCAGGAGCTGGACAAGTAC
AAGAACGCCGTGAGCTGCAGCTGTGATGCAGAGACACCCCCACCAACGCCAAGAACAACGTGACCCT
GGCGCGAGCTGCCCGGTTCATGAACGGAGATTCCTGGGCTTCCTGCTGGGAGTGGGCAGCGCCATCGCCAG
GAGCAAGAAGCGGAAGCGGAGAGTCTGCTAAGGCAGCCTGAGAGACAGATCAAGAGCGCCCTG
CGGAGTGGCCCGTGTCTAAGGCCGTGGTGTCCCTGAGCAACAGCAACGGCGTGTCCGTGCTGACCAGCAAGGTGC
CTGTCCACCAACAAGGCCGTGAGTTCGACAAGCAGCTGCTGACACCCCCTGTGAGATCGGAGATCACCAGG
TGGATCTGAAGAACTACATCGACAGACCGTGATCGAGTTCCAGCAGCTGCTGACCACCATCCACCTACATGCTGACCACTACATGCTGACCACTACATGCTGAACAAGCAGCTGCTCCATC
AGCAACATCGAGACCGTGAACGCCGGCACCGTGAACATCAGCGCTACATGCTGACCACCGCTGGGAGATCACCAGG
AGTTCAGCGTGAACGCCGGCACCGTGAACATCAGCGCTACATGCTGACCAACAAAAGCTGATGAGCAACAACGTGC
GCTGTCCCTGATCAATGACATGCAGCAGACTACAGACATCATGAGCATCATCAAGGAAGAGGTGCTGGCCTACGTG
AGATTGTGAGGCAGCAGACTACAGACATCATGAGCATCATCAAGGAAGAGGTGCTGGCCTACGTG
GTGCAGCTGCCCGTGACGGCGTGATCGATACCCCTTGCTGTGGAAGCTGCACACCAGCCCTCTGT
GTACCACCAACAACAAGGAGGCAGCAACATCTGCCTGACCAGGCCGATAGAGGCTGGTACTG
TGACAATGCGGCAGCCGTGTCCTTCTTCCCCCAGCCCAGACCTGTAAGGTGCAGAGCAACCGG
GTGTTCTGTGACACCCAAGTACGACTGTAAGATCATGACCTCCAAGACCAAGAGTGTCCAGCAGCGTGATTA
CTTCAACCCCAAGTACGACTGTAAGATCATGACCTCCAAGACCAAGAGTGTACCGCCAGCAACAAGAACCG
CCAGCTGGGCCGCCATCGTCGTCCTACGGCAACGGCTGTGACTACGTGTCAACAAGGGCAAGAGCCTGTAACGTGACCGTGTC
GGGATCATCAAGACCTTCAGCAACGGCTGTGACTACGTGTCAACAAGGGCATGACCAGCATGACCGTGAAGGGCGAG
TGTGGGCAACACTGTACTACGTGAATAAGCAGGAGGCAAGTTCCCTAGCGACGAGTTCGATGCCAGCATCAGCCA
CCATCATCAACTTCTACGACCCCGGGTTGGTTCCCTAGCGACGAGTTCGATGCCAGCATCAGCCA
GGTGAACGAGAAGATCAACCAGAGCCACCAGAGCCTGGCCTTCATCAGGAAGAGCGACGAGCTGCTGCACAAT
GTGAATGCCGGCAAGAGCACCACAACATCATGATCACCACCATCATCATCATCATCGTGATC
CTGCTGTCTCTGATTGCTGTGGGCCTGGTGCTGTGTAAGGCCAGATCATCATCGTCTAGCACCCCCGTGACCCT
GTCCAAGGACCAGCTGTCCGGCATCAACAACATCGCCCTTCTCCAACTGATGAGGATCCAG

FIG. 34C

SEQ ID NO: 17 New F nucleotide sequence

GGTACCGTCGACGCCACCATGGAGCTGCTGATCCTGAAGGCCAACGCCATCACCACCATCCTGACC
GCCGTGACCTTCTGCTTCGCCAGCGGCCAGAATATCACCGAGGAGTTCTACCAGAGCACCTGTAGCG
CCGTGTCCAAGGGCTACCTGAGCGCCCTGAGAACCGGCTGGTACACCAGCGTGATCACCATCGAGC
TGTCCAACATCAAGGAAAACAAGTGTAACGGCACCGACGCCAAGGTGAAGCTGATCAAGCAGGAGCT
GGACAAGTACAAGAACGCCGTGACCGAGCTGCAGCTGCTGATGCAGAGCACCCCCGCCACCAACAA
CAGAGCCAGGCGCGAGCTGCCCCGGTTCATGAACTACACCCTGAACAACGCCAAGAAAACCAACGT
GACCCTGAGCAAGAAGCGGAAGCGGAGATTCCTGGGCTTCCTGCTGGGAGTGGGCAGCGCCATCGC
CAGCGGAGTGGCCGTGTCTAAGGTGCTGCACCTGGAGGGCGAGGTGAACAAGATCAAGAGCGCCCT
GCTGTCCACCAACAAGGCCGTGGTGTCCCTGAGCAACGGCGTGTCCGTGCTGACCAGCAAGGTGCT
GGATCTGAAGAACTACATCGACAAGCAGCTGCTGCCCATCGTGAACAAGCAGAGCTGCTCCATCAGC
AACATCGAGACCGTGATCGAGTTCCAGCAGAAGAACAACCGGCTGCTGGAGATCACCAGGGAGTTCA
GCGTGAACGCCGGCGTGACCACCCCTGTGAGCACCTACATGCTGACCAACAGCGAGCTGCTGTCCC
TGATCAATGACATGCCCATCACCAACGACCAGAAAAAGCTGATGAGCAACAACGTGCAGATTGTGAG
GCAGCAGAGCTACAGCATCATGAGCATCATCAAGGAAGAGGTGCTGGCCTACGTCGTGCAGCTGCC
CCTGTACGGCGTGATCGATACCCCTTGCTGGAAGCTGCACACCAGCCCTCTGTGTACCACCAACACC
AAGGAGGGCAGCAACATCTGCCTGACCAGGACCGATAGAGGCTGGTACTGTGACAATGCCGGCAGC
GTGTCCTTCTTCCCCCAGGCCGAGACCTGTAAGGTGCAGAGCAACCGTGTCTTCAACCCCAAGTACGACTG
ACAGCCTGACCCTGCCCAGCGAGGTGAACCTGTGTAACGTGGACATCTTCAACCCCAAGTACGACTG
TAAGATCATGACCTCCAAGACCGACGTGTCCAGCAGCGTGATTACCAGCCTGGGCGCCATCGTGTCC
TGCTACGGCAAGACCAAGTGTACGCCAGCTGTCAGCATCAGCGGCGATCATCAAGACCTTCAGCAACG
GCTGTGACTACGTGTCCAACAAGGGCGTGGACACCGTGTCTGTGGGCAACACACTGTACTACGTGAA
TAAGCAGGAGGGCAAGAGCCTGTACGTGAAGGGCGAGCCCATCATCAACTTCTACGACCCCCTGGT
GTTCCCTAGCGACGAGTTCGATGCCAGCATCAGCCAGGTGAACGAGAAGATCAACCAGAGCCTGGC
CTTCATCAGGAAGAGCGACGAGCTGCTGCACAATGTGAATGCCGGCAAGAGCACCACCAACATCATG
ATCACCACAATCATCATCGTGATCATTGTGATCCTGCTGTCTCTGATTGCTGTGGGCCTGCTGCTGTA
CTGTAAGGCCAGATCTACCACCCCCGTGTCCAAGGACCAGCAGCTGCCGGCATCAACAACATCGCC
TTCTCCAACTGATGAGGATCCGAGCTC

FIG. 34D

SEQ ID NO: 18   New F nucleotide sequence - modified

GGTACCGTCGACGCCACCATGGAGCTGCTGATCCTGAAGGCCAACGCCATCACCACCATCCTGACC
GCCGTGACCTTCTGCTTCGCCAGCGGCCAGAATATCACCGAGGAGTTCTACCAGAGCACCTGTAGCG
CCGTGTCCAAGGGCTACCTGAGCGCCCTGAGAACCGGCTGGTACACCAGCGTGATCACCATCGAGC
TGTCCAACATCAAGGAAAACAAGTGTAACGGCACCGACGCCAAGGTGAAGCTGATCAAGCAGGAGCT
GGACAAGTACAAGAACGCCGTGCCCGAGCTGCTGCAGCACCCCGCCACCAACAA
CAGAGCCAGGCGCGAGCTGCCCCGGTTCATGAACTACACACCCTGAACAACGCCAAGAAAACCAACGT
GACCCTGAGCAAGGTGGAGATTCCTCGGCTTCCTGCTGGGAGTGGGCAGCGCCATCGC
CAGCGGAGTGGCCGTGTCTAAGGTGCTGCACCTGGAGGGCGAAGTGAACAAGATCAAGAGCGCCCT
GCTGTCCACCAACAAGGCCGTGGTGTCCCTGAGCAACGGCGTGTCCGTGCTGACCAGCAAGGTGCT
GGATCTGAAGAACTACATCGACAAGCAGTTGATCGAGTTGACCAACCGGCTGCTGGAGATCACCAGGAGTTCA
ACATCAGAGACCGTGACCATCCCGCGTGACCATGCCCATCGACAACCAGAGCAACAACGTGCAGATTGTGAG
GCGTGAACGCCGGCGTGACCATCGCCATGCCCATCGACAACCAGAGCAACAACGTGCAGATTGTGAG
TGATCAATGACATGACATGCCCATCGACATCAACCAGAGCAACAACGTGCAGATTGTGAG
GCAGCAGAGCTACAGCATCATGAGCATCATCAAGGAAGAGGTGCTGGCCTACGTGGTGCAGCTGCC
CCTGTACGGCGTGATCGATACCCCTTGCTGGAAGCTGCACACCAGCCCTCTGTGTACCACCAACACC
AAGGAGGCGCAGCAACATCTGCCTGACCAGACCTGGTACTGTGACAATGCCGGCAGC
GTGTCCTTCTTTCCGCAAGCCAAGAGACCCTGCCCAGCGAGGTGAACCTGTGTAACGTGTCTGACTGCTGTCCACCATGA
ACAGCCTGACCCTGCCCAGCGAGGTGAACCTGTGTAACGTGTCTGACTGTGGACATCTTCAACCCCAAGTACGACTG
TAAGATCATGACCTCCAAGACCGACGTGTCCAGCAGCGTGATTACCAGCCTGGGCGCCATCGTGTCC
TGCTACGGCAAGACCAAGTGTACCGCCAGCAACAAGAACCGGGGATCATCAAGACCTTCAGCAACG
GCTGTGACTACGTGTCCAACAAGGGCGTGGACACTGGCTGGGCAACACACTGTACTACGTGAA
TAAGCAGGAGGGCAAGAGCCTGTACGTGAAGGCCGAGCCATCATCAACGAGAAGATCAACCAGAGCCTGGC
GTTCCCCTAGCCGACGAGTTCGATGCCAGCATCAGCCAGGTGAATGAGAGAGCACCAACATCATG
CTTCATCAGGAAGAGACGAGTTCGATGCCAGCATCAGCCAGGTGAATGCCGGCAAGAGCACCACCAACATCATG
ATCACCACAATCATCATCGACCTGTCTCTGATTGTCTGCTGTGGGCCTGCTGCTGTA
CTGTAAGGCCAGATCCACCCCGTGACCCTGTCCAAGGACCAGCTGTCCGGCATCAACAACATCGCC
TTCTCCAACTGATGAGGATCCGAGCTC

Figure 35

SEQ ID NO: 15

MSKNKDQRTAKTLERTWDTLNHLLFISSCLYKLNLKSVAQITLSILAIIISTSLIIAAIIFIASANHKVTPTTAII
QDATSQIKNTTPTYLTQNPQLGISPSNPSEITSQITILASTTPGVKSTLQSTTVKTKNTTTTQTQPSKP
TTKQRQNKPPSKPNNDFHFEVFNFVPCSICSNNPTCWAICKRIPNKKPGKKTTTKPTKKPTLKTTKKD
PKPQTTKSKEVPTTKPTEEPTINTTKTNIITTLLTSNTTGNPELTSQMETFHSTSSEGNPSPSQVSTTSE
YPSQPSSPPNTPRQ

CODON MODIFIED IMMUNOGENIC COMPOSITIONS AND METHODS OF USE

RELATED APPLICATIONS

This application claims the benefit of U.S. Provisional Application No. 60/872,071, filed Nov. 30, 2006. The entire contents of the aforementioned application are hereby incorporated herein by reference.

SEQUENCE LISTING

The instant application contains a Sequence Listing which has been submitted via EFS-Web and is hereby incorporated by reference in its entirety. Said ASCII copy, created on Mar. 24, 2010, is named 66425479.txt and is 39,200 bytes in size.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

The human Paramyxoviruses are important human pathogens, and are a common cause of respiratory disease in children. Approximately half of the cases of infantile bronchiolitis, croup, and pneumonia are caused by parainfluenza viruses and respiratory syncytial viruses. Although measles and mumps used to be a significant problem worldwide, their incidence has decreased greatly in developed nations due to the success of immunization campaigns, although measles remains to be a major cause of death among malnourished infants in the developing world.

Human respiratory Syncytial virus (RSV) is the main cause of lower respiratory tract infections among infants and young children. Globally, 65 million infections occur every year resulting in 160,000 deaths (Robbins, A., and Freeman, P. (1988) Sci. Am. 259, 126-133). In the United States alone, 100,000 children may require hospitalization for pneumonia and bronchiolitis caused by RSV in a single year (Glezen, W. P., Taber, L. H., Frank, A. L. and Kasel, J. A. (1986) Am. J. Dis. Child. 140, 143-146; Katz, S. L. New vaccine development establishing priorities. Vol. 1. Washington: National Academic Press. (1985) pp. 397-409). Providing inpatient and ambulatory care for children with RSV infections costs in excess of $340 million annually in the USA (Wertz, G. W., Sullender, W. M. (1992) Biotech. 20, 151-176). Severe lower respiratory tract disease due to RSV infection predominantly occurs in infants two to six months of age. Approximately 4,000 infants in the United States die each year from complications arising from severe respiratory tract disease caused by infection with RSV and Parainfluenza type 3 virus (PIV-3). The World Health Organization (WHO) and the National Institute of Allergy and Infectious Disease (NIAID) vaccine advisory committees have ranked RSV second only to HIV for vaccine development. RSV is highly infectious, and is transmitted by respiratory secretions. Although it typically presents as a febrile rhinitis and/or pharyngitis and commonly involves the inner ear, RSV results in severe illness in about 1% of all babies. Severe RSV infection is characterized by a pronounced cough and wheezing, which eventually develops into dyspnea and a high respiratory rate and hypoxemia. Additionally, pregnant women, young children, the elderly and immunosuppressed organ transplant patients are at risk for developing pneumonia due to RSV infection. Among the major challenges for RSV vaccine development include the young age of onset of serious disease, the failure of natural immunity to protect against reinfection, and the legacy of vaccine-enhanced disease.

As described above, Paramyxoviral infection, and specifically RSV infection, are prevalent throughout the population, and pose a particular risk in certain vulnerable subpopulations. Thus, there remains a need in the art for the development of an effective vaccine to treat human Paramyxovirus, and specifically RSV.

SUMMARY OF THE INVENTION

As described below, the present invention features immunogenic compositions comprising codon modified genes. In certain embodiments of the invention, the codon-modified genes encode viral glycoproteins or fragments. The immunogenic compositions of the invention are useful in various methods of treatment, such as preventing or treating viral infection, as described herein.

In one aspect, the invention provides an immunogenic composition comprising one or more codon modified viral genes or fragments thereof, wherein the codon-modified genes or fragments thereof encode Paramyxovirus gene products. In one embodiment, the Paramyxovirus is selected from the group consisting of: Pneumovirus, Avulavirus, Henipavirus, Morbillivirus, Respirovirus, Rubulavirus, Parainfluenza virus and Metapneumovirus. In a further particular embodiment, the Pneumovirus is Respiratory Syncytial Virus (RSV).

In a particular embodiment of any of the above aspects, the codon-modified genes or fragments thereof encode viral surface proteins. In another embodiment, the codon-modified genes or fragments thereof encode viral glycoproteins or fragments thereof. In another particular embodiment, the viral glycoproteins or fragments thereof encode one or more of the fusion (F), membrane anchored attachment (Gr), matrix (M) or (M2), small hydrophobic (SH), nucleoprotein (N), surface (HN) glycoproteins, or fragments thereof. In still a further embodiment, the codon-modified genes, or fragments thereof, induce an immune response. In one embodiment, the immune response is an antibody response. In another embodiment, the immune response is a T cell response. In another particular embodiment, the codon-modified genes, or fragments thereof, enhance protein expression.

In one embodiment of the immunogenic composition comprising one or more codon modified viral genes or fragments thereof, the codon-modified gene, or fragments thereof, comprises the Paramyxovirus membrane anchored attachment (Gr) glycoprotein. In a particular embodiment, the codon-modified gene, or fragments thereof, comprises the membrane anchored attachment (Gr) glycoprotein of RSV. In another embodiment, the codon-modified membrane anchored attachment (Gr) glycoprotein comprises SEQ ID NO: 2.

In another embodiment of the immunogenic composition comprising one or more codon modified viral genes or fragments thereof, the codon-modified gene, or fragments thereof, comprises the Paramyxovirus matrix (M) glycoprotein. In a particular embodiment, the codon-modified gene, or fragments thereof, comprises the matrix (M) glycoprotein of RSV. In another embodiment, the codon-modified matrix (M) gene comprises SEQ ID NO: 4.

In another embodiment of the immunogenic composition comprising one or more codon modified viral genes or fragments thereof, the codon-modified gene, or fragments thereof, comprises the Paramyxovirus matrix (M2) glycoprotein. In a particular embodiment, the codon-modified gene, or fragments thereof, comprises the matrix (M2) glycoprotein of RSV. In another embodiment, the codon-modified matrix (M2) gene comprises SEQ ID NO: 6.

In another embodiment of the immunogenic composition comprising one or more codon modified viral genes or fragments thereof, the codon-modified gene, or fragments thereof, the codon-modified gene, or fragments thereof, comprises a fusion of the Paramyxovirus codon-modified (M) matrix glycoprotein and codon-modified (M2) matrix glycoprotein. In a particular embodiment, the codon-modified gene, or fragments thereof, comprises a fusion of codon-modified (M) matrix glycoprotein and codon-modified (M2) matrix glycoprotein of RSV. In another embodiment, the codon-modified matrix fusion (M/M2) gene comprises SEQ ID NO: 8.

In another embodiment of the immunogenic composition comprising one or more codon modified viral genes or fragments thereof, the codon-modified gene, or fragments thereof, comprises the Paramyxovirus nucleoprotein (N). In a particular embodiment, the codon-modified gene, or fragments thereof, comprises the nucleoprotein (N) of RSV. In another embodiment, the codon-modified nucleoprotein (N) gene comprises SEQ ID NO: 10

In another embodiment of the immunogenic composition comprising one or more codon modified viral genes or fragments thereof, the codon-modified gene, or fragments thereof, comprises the Paramyxovirus SH small hydrophobic glycoprotein. In a particular embodiment, the codon-modified gene, or fragments thereof, comprises the SH envelope glycoprotein of RSV. In another embodiment, the codon-modified SH envelope glycoprotein comprises SEQ ID NO: 12.

In another embodiment of the immunogenic composition comprising one or more codon modified viral genes or fragments thereof, the codon-modified gene, or fragments thereof, comprises the Paramyxovirus fusion (F) glycoprotein. In a particular embodiment, the codon-modified gene, or fragments thereof, comprises the fusion (F) glycoprotein of RSV. In another embodiment, the codon-modified F gene comprises SEQ ID NO: 14. In another embodiment, the codon-modified F gene comprises SEQ ID NO: 17. In another embodiment, the codon-modified F gene comprises SEQ ID NO: 18.

In another embodiment of any of the immunogenic compositions described herein, the codon-modified gene, or fragments thereof, comprises the cytoplasmic tail plus one amino acid residue of the fusion (F) glycoprotein of RSV. In a particular embodiment, the fragment comprising the cytoplasmic tail plus one amino acid residue corresponds to residues 1-551 of SEQ ID NO: 13, SEQ ID NO:14 or SEQ ID NO: 16.

In a particular embodiment of any of the immunogenic compositions described herein, the codon-modified genes, or fragments thereof, further comprise one or more additional mutations.

In another embodiment of the invention, a nucleic acid molecule encodes any one of the codon modified genes, or fragments thereof as described herein.

In one particular embodiment, the invention provides an immunogenic composition comprising one or more of the codon modified nucleic acid molecules encoding the genes or fragments of any one of the aspects or embodiments described herein, wherein the codon modification enhances protein expression and modulates an immune response.

In a further embodiment, the invention provides a vector comprising a nucleic acid molecule encoding one or more codon modified genes, or fragments thereof, of any of the aspects or embodiments described herein.

In yet another further embodiment, the invention provides a plurality of vectors, each comprising one or more of the codon-modified genes, or fragments thereof, of any one of the aspects and embodiments described herein. In one embodiment of the plurality of vectors, two or more vectors each comprise one or more of the codon-modified genes, or fragments thereof, of any one of the aspects and embodiments described herein. In another embodiment, the additional codon-modified gene or fragment comprises the membrane anchored attachment (Gr) glycoprotein of RSV. In a further embodiment, the additional codon-modified gene or fragment comprises SEQ ID NO: 2. In another further embodiment, the additional codon-modified gene or fragment comprises the matrix fusion (M/M2) glycoprotein of RSV. In another further embodiment, the additional codon-modified gene or fragment comprises SEQ ID NO: 8. In still another further embodiment, the additional codon-modified gene or fragment comprises the nucleoprotein (N) glycoprotein of RSV. In another further embodiment, the additional codon-modified gene or fragment comprises SEQ ID NO: 10.

In another embodiment, the invention provides the vector or plurality of vectors of any one of the aspects or embodiments as described herein, wherein the vector is a replication competent or replication defective vector. In certain embodiments, the replication competent vector is selected from the group consisting of parainfluenza virus, Paramyxovirus, Newcastle disease virus, VSV, BCG, vaccinia, reovirus, rhinovirus, poliovirus, and adenovirus. In other certain embodiments, the vector is a replication defective vector. In still further embodiments, the replication defective vector is selected from the group consisting of poxviruses, alpha viruses, Venezuelan equine encephalitis viruses (EEV), Sinbis viruses, DNA viruses, adeno associated viruses (AAV), herpes simplex viruses (HSV), adenoviruses, and HPV viruslike particles. In a related embodiment, the poxvirus is selected from modified virus Ankara (MVA), NYVAC, Fowlpox, or canarypox. In a further embodiment, the adenoviral vector is selected from the group consisting of rAd5, rAd26, rAd 41, rAd6, and rAd35. In still a further embodiment, the nucleic acid vector is Semliki forest vector.

In another embodiment, the vector is a chimeric vector. In still another embodiment, in any of the vectors as described herein the codon modified nucleic acid molecule or fragment is operably linked to a promoter.

In another embodiment of the invention is a host cell comprising the vector of any one of the aspects and embodiments as described herein. In a particular embodiment, the cell expresses a codon modified nucleic acid molecule or fragment. In one embodiment, contacting the host cell with the vector occurs in vitro. In another embodiment, contacting the host cell with the vector occurs in vivo. In another embodiment, the cell is a mammalian cell. In another embodiment, the cell is a human cell.

Another aspect of the invention teaches a method of eliciting an immune response capable of preventing viral infection in a subject comprising administering to the subject an immunogenic composition comprising one or more vectors comprising one or more viral codon modified genes, or fragments thereof, wherein the codon modification induces an immune response, and a pharmaceutically acceptable carrier, and thus eliciting an immune response capable of preventing viral infection in a subject.

Another particular aspect of the invention teaches a method of treating a subject having a viral infection comprising administering to the subject an immunogenic composition comprising one or more vectors comprising one or more viral codon modified genes, or fragments thereof, wherein the codon modification induces an immune response, and a pharmaceutically acceptable carrier, and thus treating viral infection in a subject.

Another aspect of the invention teaches a method of eliciting an immune response capable of preventing Paramyxoviral infection in a subject comprising administering to the subject an immunogenic composition comprising one or more vectors comprising one or more Paramyxovirus codon modified genes, or fragments thereof, wherein the codon modification induces an immune response, and a pharmaceutically acceptable carrier, and thus eliciting an immune response capable of preventing Paramyxoviral infection in a subject.

Another particular aspect of the invention teaches a method of treating a subject having Paramyxoviral infection comprising administering to the subject an immunogenic composition comprising one or more vectors comprising one or more Paramyxovirus codon modified genes, or fragments thereof, wherein the codon modification induces an immune response, and a pharmaceutically acceptable carrier, and thus treating Paramyxoviral infection in a subject.

Another aspect of the invention teaches a method of eliciting an immune response capable of preventing RSV infection in a subject comprising administering to the subject an immunogenic composition comprising: one or more vectors comprising one or more RSV codon modified genes, or fragments thereof encoding one or more polypeptides of claims 1-36, wherein the codon modification induces an immune response, and a pharmaceutically acceptable carrier, and thus eliciting an immune response capable of preventing RSV infection in a subject.

Another particular aspect of the invention teaches a method of treating a subject having RSV infection comprising administering to the subject an immunogenic composition comprising: one or more vectors comprising one or more RSV codon modified genes, or fragments thereof encoding one or more polypeptides of any of the aspects as described herein, wherein the codon modification induces an immune response, and a pharmaceutically acceptable carrier, and thus treating a subject having RSV infection.

Another aspect of the invention teaches a method for eliciting an immune stimulatory activity of an RSV glycoprotein, the method comprising: introducing a codon modification in one or more RSV glycoprotein genes, or fragments into one or more vectors for administration to a subject thereby eliciting an immune stimulatory activity of an RSV glycoprotein.

In one embodiment, the method further comprises the step of detecting an alteration in the immune stimulatory activity of the RSV glycoprotein.

In a particular embodiment of any of the aspects of the above methods, the one or more vectors are administered in a prime boost regimen. In another embodiment, the prime boost regimen is homologous. In a related embodiment, the prime boost regimen is heterologous. In still another related embodiment, the one or more vectors are administered together, either sequentially or in admixture. In a further embodiment, vector priming increases T cell cytolytic function.

In a particular embodiment of any of the aspects of the above methods, the alteration in immune stimulatory activity is an antibody response. In another particular embodiment of any of the aspects of the above methods, the alteration in immune stimulatory activity is a T cell response. In a further embodiment, the alteration is detected by detection of cytokine levels. In another further embodiment, the alteration is detected by CD8 T+ cell activity. In another further embodiment, the alteration is detected by number of T regulatory cells. In another further embodiment, the alteration is detected by the alteration is detected by T cell cytolytic function. In another particular embodiment of any of the aspects of the above methods, the codon modification enhances protein expression.

Another particular aspect of the invention teaches a method for enhancing protein production of a Paramyxovirus glycoprotein, the method comprising: introducing a codon modification in one or more Paramyxovirus glycoprotein genes or fragments into one or more vectors for administration to a subject and thus enhancing protein production of a Paramyxovirus glycoprotein.

In one embodiment, the one or more vectors are administered in a prime boost regimen.

In one embodiment, the codon modification is in the promoter region of the gene. In another embodiment, the method further comprises the step of detecting an enhancement in protein production. In a particular embodiment, the enhancement in protein production is detected by a method selected from the group consisting of: ELISA, Western Blot, fluorimetry or colorimetry.

In a particular embodiment of any of the aspects of the above methods, the immune response or increase in protein production is generated by a single administration of the immunogenic composition.

In another particular embodiment of any of the aspects of the above methods, the immune response or increase in protein production is generated by more than one administration of the immunogenic composition.

In a particular embodiment of any of the aspects of the above methods, the subject is a human. In a further embodiment, the human is selected from the group consisting of: pregnant women, neonates, young infants, organ transplantation patients, and the elderly. In another embodiment, the organ transplantation patient is selected from the group consisting of: lung transplantation patients prior to transplant and bone marrow transplantation patients prior to transplant.

In another particular embodiment of any of the aspects of the above methods, the vector comprising the codon-modified genes or fragments is a replication competent or replication defective vector.

In another embodiment the replication competent vector is selected from the group consisting of: parainfluenza virus, Paramyxovirus, Newcastle disease virus, VSV, BCG, vaccinia, reovirus, rhinovirus, poliovirus, and adenovirus. In a related embodiment, the replication defective vector is selected from the group consisting of: poxviruses, alpha viruses, Venezuelan equine encephalitis viruses (EEV), Sinbis viruses, DNA viruses, adeno associated viruses (AAV), herpes simplex viruses (HSV), adenoviruses, and HPV virus-like particles. In particular embodiments, the poxvirus is selected from modified virus Ankara (MVA), NYVAC, Fowlpox, or canarypox.

In a particular embodiment of any of the aspects of the above methods, the immunogenic composition is administered by a route selected from the group consisting of: orally, intramuscularly, intradermally, intravenously, intranasally, and intraperintoneally.

In another particular embodiment of any of the aspects of the above methods, the immunogenic composition is delivered in a cochlear delivery system.

In a particular embodiment of any of the aspects of the above methods, the immunogenic composition is delivered in an exosomal delivery system.

In another particular embodiment of any of the aspects of the above methods, the immunogenic composition is delivered using a nanoparticle delivery system.

In a particular embodiment of any of the aspects of the above methods, the immunogenic composition further comprises an adjuvant. In one embodiment, the adjuvant is selected from the group consisting of oil emulsions, mineral compounds, bacterial products, liposomes, and immunostimulating complexes.

In a particular embodiment of any of the aspects of the above methods, the Paramyxoviral infection is by a virus selected from the group consisting of: Avulaviral infection, Henipaviral infection, Morbilliviral infection, Respiroviral infection, Rubulaviral infection, Pneumoviral infection, and Metapneumoviral infection.

In another particular embodiment of any of the aspects of the above methods, the Paramyxovirus is selected from the group consisting of human, canine, feline, avian, murine, simian, bovine or ovine Paramyxovirus.

In a particular embodiment of any of the aspects of the above methods, the Paramyxovirus is selected from the group consisting of: Pneumovirus, Avulavirus, Henipavirus, Morbillivirus, Respirovirus, Rubulavirus, and Metapneumovirus. In a further embodiment, the Pneumovirus is Respiratory Syncytial Virus (RSV).

In a further aspect, the invention provides a kit for, use in eliciting an immune response capable of preventing a viral infection in a subject, the kit comprising one or more vectors comprising one or more codon modified viral genes or fragments thereof, and a pharmaceutically acceptable carrier.

In another aspect, the invention provides a kit for use in eliciting an immune response capable of preventing Paramyxoviral infection in a subject, the kit comprising one or more vectors comprising one or more codon modified Paramyxovirus genes or fragments thereof, and a pharmaceutically acceptable carrier.

In a further aspect, the invention provides a kit for use in treating a subject having a viral infection, the kit comprising one or more vectors comprising one or more codon modified viral genes or fragments thereof, and a pharmaceutically acceptable carrier.

In another aspect, the invention provides a kit for use in treating a subject having Paramyxoviral infection, the kit comprising one or more vectors comprising one or more codon modified Paramyxovirus genes or fragments thereof, and a pharmaceutically acceptable carrier.

In a further aspect, the invention provides a kit for use in eliciting an immune response capable of preventing a viral infection in a subject, the kit comprising one or more vectors comprising one or more codon modified viral genes or fragments thereof encoding one or more polypeptides of any of the above aspects as described herein, and a pharmaceutically acceptable carrier.

In another aspect, the invention provides a kit for use in eliciting an immune response capable of preventing Paramyxoviral infection in a subject, the kit comprising: one or more vectors comprising one or more codon modified Paramyxovirus genes or fragments thereof encoding one or more polypeptides of any of the aspects as described herein, and a pharmaceutically acceptable carrier.

In a further aspect, the invention provides a kit for use in enhancing protein production of a viral glycoprotein, the kit comprising one or more vectors comprising one or more codon modified viral genes or fragments thereof encoding one or more polypeptides of any of the aspects as described herein, and a pharmaceutically acceptable carrier.

In another aspect, the invention provides a kit for use in enhancing protein production of a Paramyxovirus glycoprotein, the kit comprising one or more vectors comprising one or more codon modified Paramyxovirus genes or fragments thereof encoding one or more polypeptides of any of the aspects as described herein, and a pharmaceutically acceptable carrier.

In one embodiment, the Paramyxovirus of any of the kits as described in the above aspects, is selected from the group consisting of: Avulaviral infection, Henipaviral infection, Morbilliviral infection, Respiroviral infection, Rubulaviral infection, Pneumoviral infection, and Metapneumoviral infection. In a particular embodiment, the Paramyxovirus is selected from the group consisting of: human, avian, murine, simian, bovine or ovine Paramyxovirus. In another particular embodiment, the Pneumovirus is Respiratory Syncytial Virus (RSV).

In another embodiment, the kits of any of the aspects as described herein further contain a plurality of vectors comprising one or more Paramyxovirus codon modified genes or fragments thereof.

In another embodiment, the kits of any of the aspects as described herein further contain two or more vectors each comprising one or more Paramyxovirus codon modified gene or fragment thereof.

In another embodiment, the kits of any of the aspects as described herein further contain one or more vectors each comprising one or more Paramyxovirus codon modified gene or fragment thereof.

In another embodiment, the kits of any of the aspects as described herein further contain an adjuvant. In a particular embodiment, the adjuvant is selected from the group consisting of: oil emulsions, mineral compounds, bacterial products, liposomes, and immunostimulating complexes.

Other features and advantages of the invention will be apparent from the detailed description, and from the claims.

BRIEF DESCRIPTION OF THE DRAWINGS

FIG. 4 shows codon modification of RSV M-M2 fusion.

The pie charts represent the relative ratios of effector and memory CD8+M2- or M-specific populations in each treatment group.

Figure 12B:
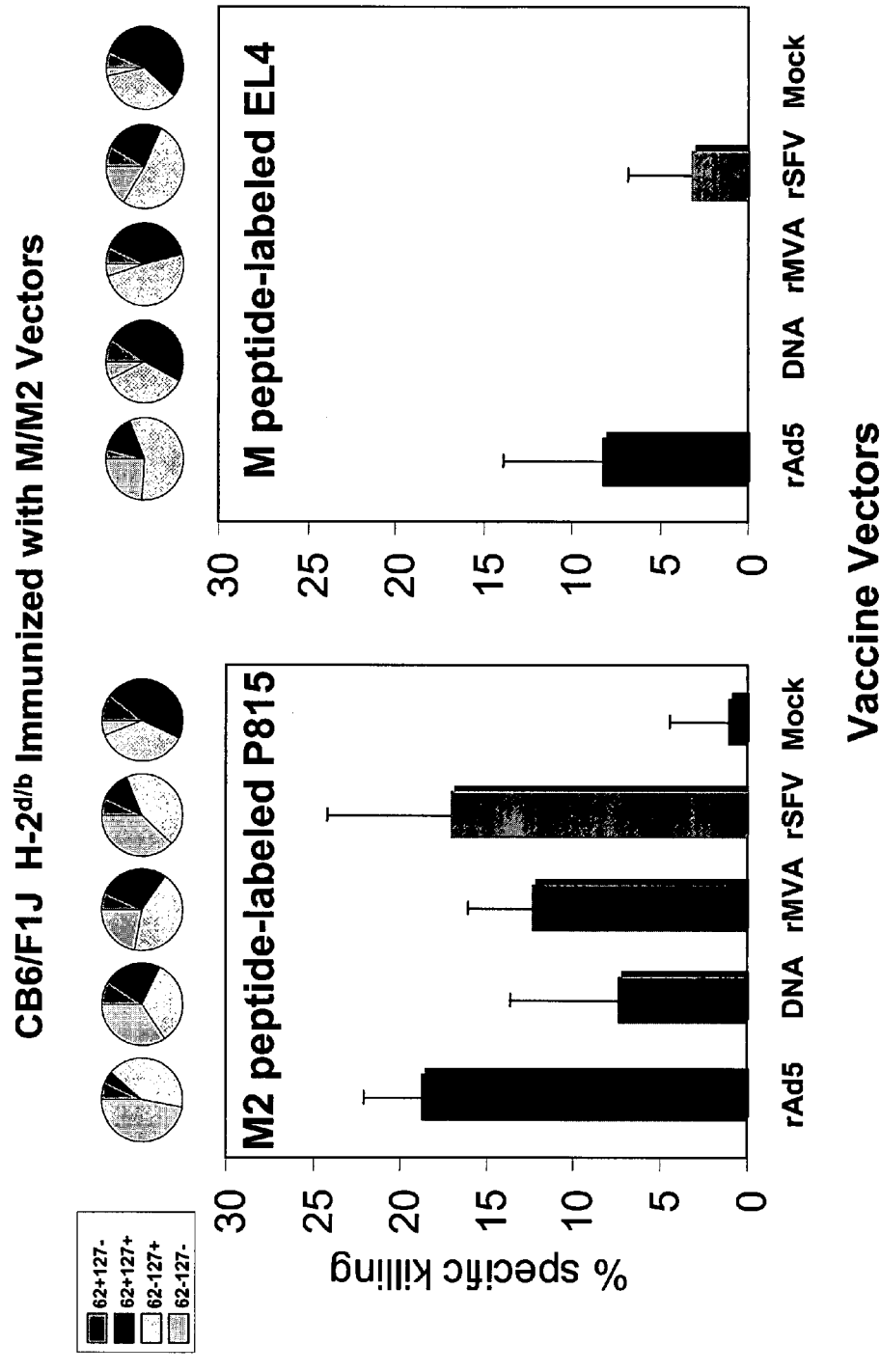
FIG. 12 (a and b) (a) is a schematic describing the experimental method used to determine cytotoxic T-cell activity in the lung. (b) is two graphs that show vaccine induced cytolytic activity. CB6/F1J H-$2^{d/b}$ mice were immunized with M/M2 vectors. The graph on the left shows results after incubation of isolated mouse lymphocytes with M2 peptide-labeled P815. The graph on the right shows results after incubation of isolated mouse lymphocytes with M peptide-labeled EL4. rAd5, DNA, rMVA, rSFV, and Mock vaccine vectors were used.
Figure 13:
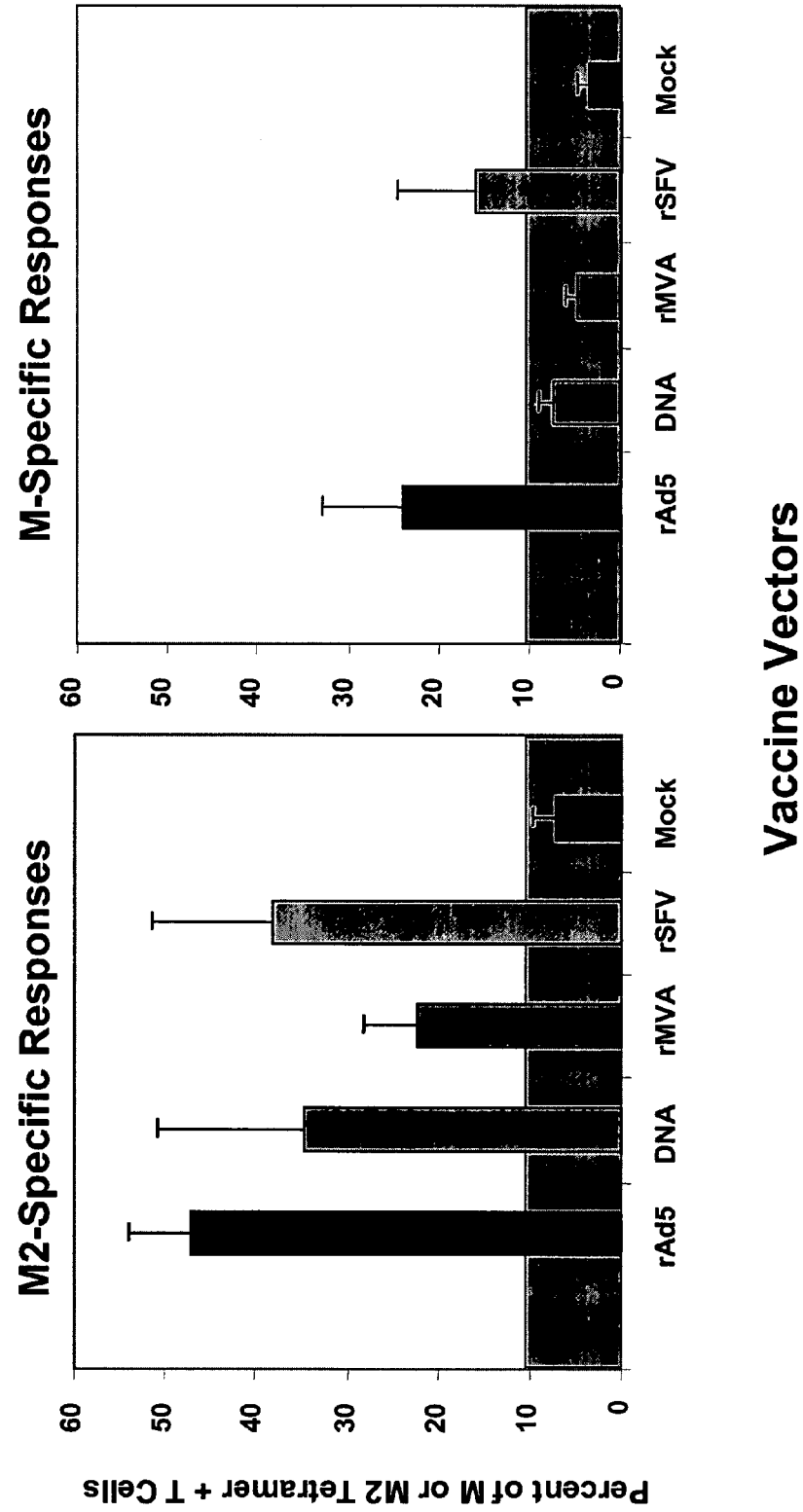
Figure 14:
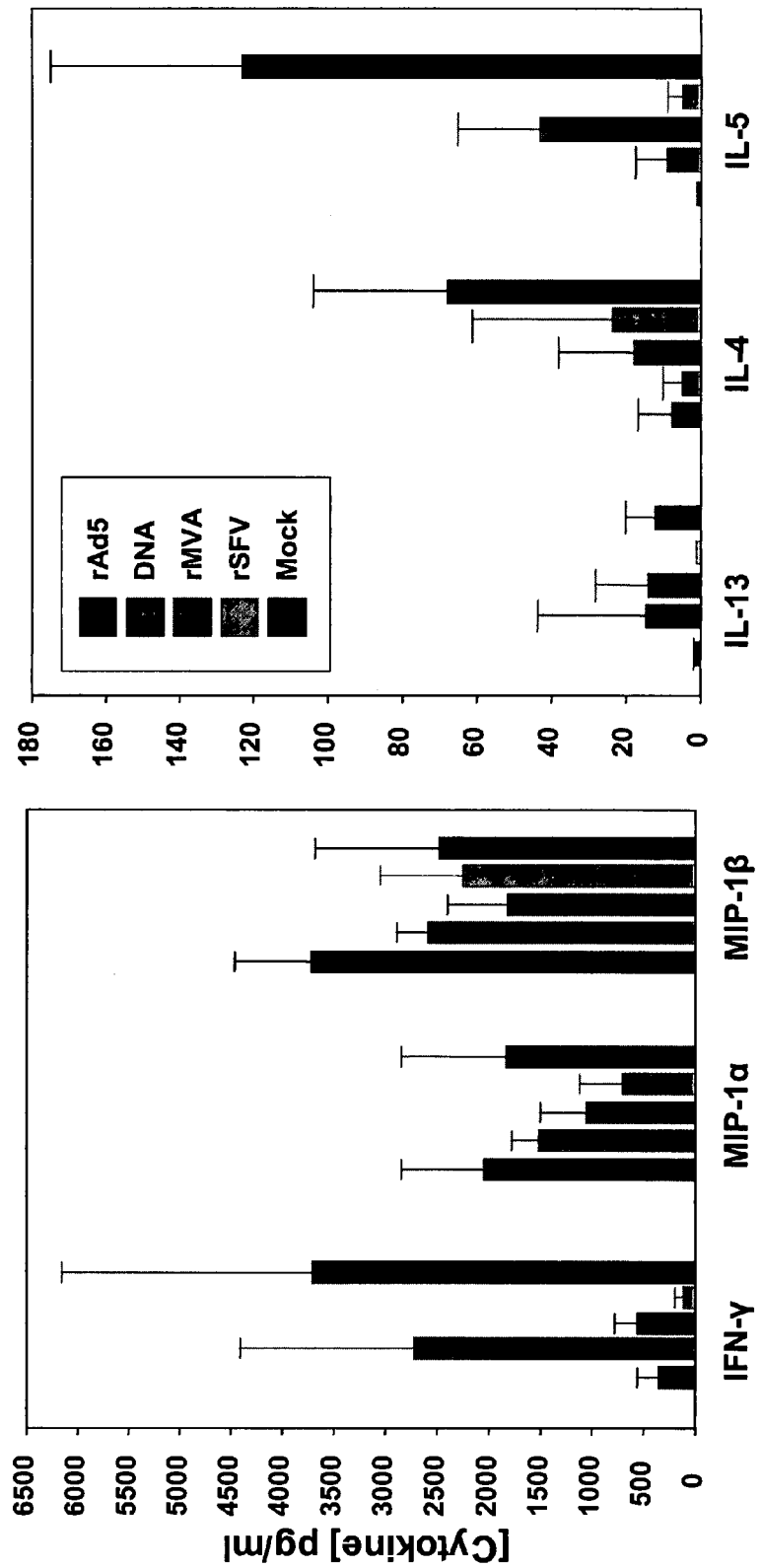

FIG. 13 is two graphs showing CD3+8+62-127 terminal effectors. CB6/F1J H-2 d/b mice were immunized with M/M2 vectors. The graph on the left shows M2-specific responses. The graph on the right shows M-specific Responses. rAd5, DNA, rMVA, rSFV, and Mock vaccine vectors were used. The frequency of terminal effectors corresponds to the cytolytic activity measured in FIG. 12b FIG. 14 is two graphs that show cytokine production in lung day 5-post RSV challenge. CB6/F1J H-2 d/b mice were immunized with M/M2 vectors. The graph on the left shows measurement of IFN-γ, MIP-1α and MIP-1β. The graph on the right shows measurement of IL-13, IL-14 and IL-5. The graph inset shows the rAd5, DNA, rMVA, rSFV, and Mock vaccine vectors used.

FIG. 15 (a and b). (a) is a schematic detailing the protocol schema. (b) is two graphs that show weight loss and virus replication after RSV challenge. BALB/c H-2d mice were immunized with M2 vectors. The graph on the left shows weight loss as percent of initial weight in the days after infection. The inset panel shows the vaccine vectors that were used. The graph on the right shows virus replication as $Log_{10}$ pfu/gram in the lung after RSV challenge. rAd5, DNA, rMVA, rSFV, and Mock vaccine vectors were used.

Figure 16B:
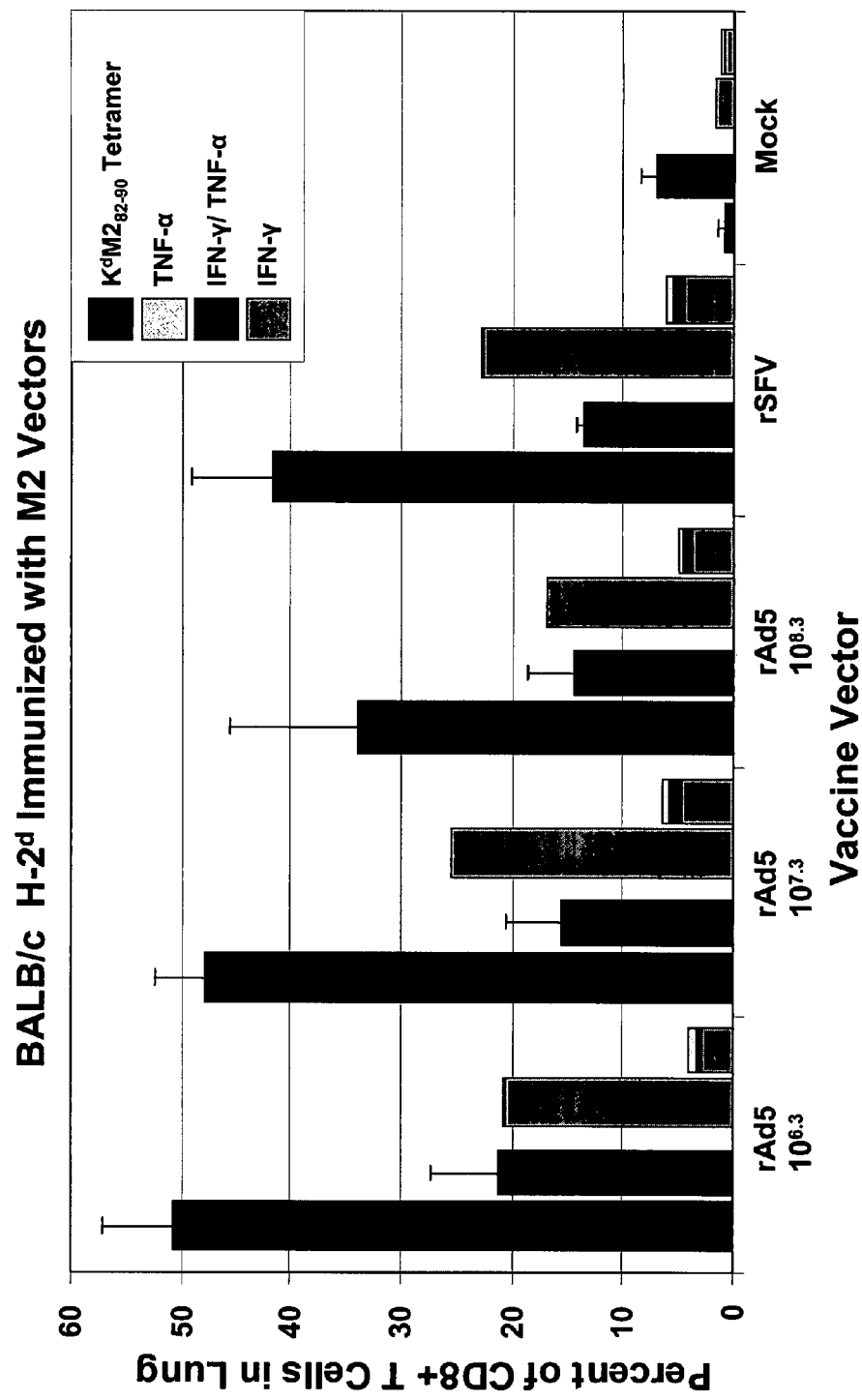
Figure 17A:
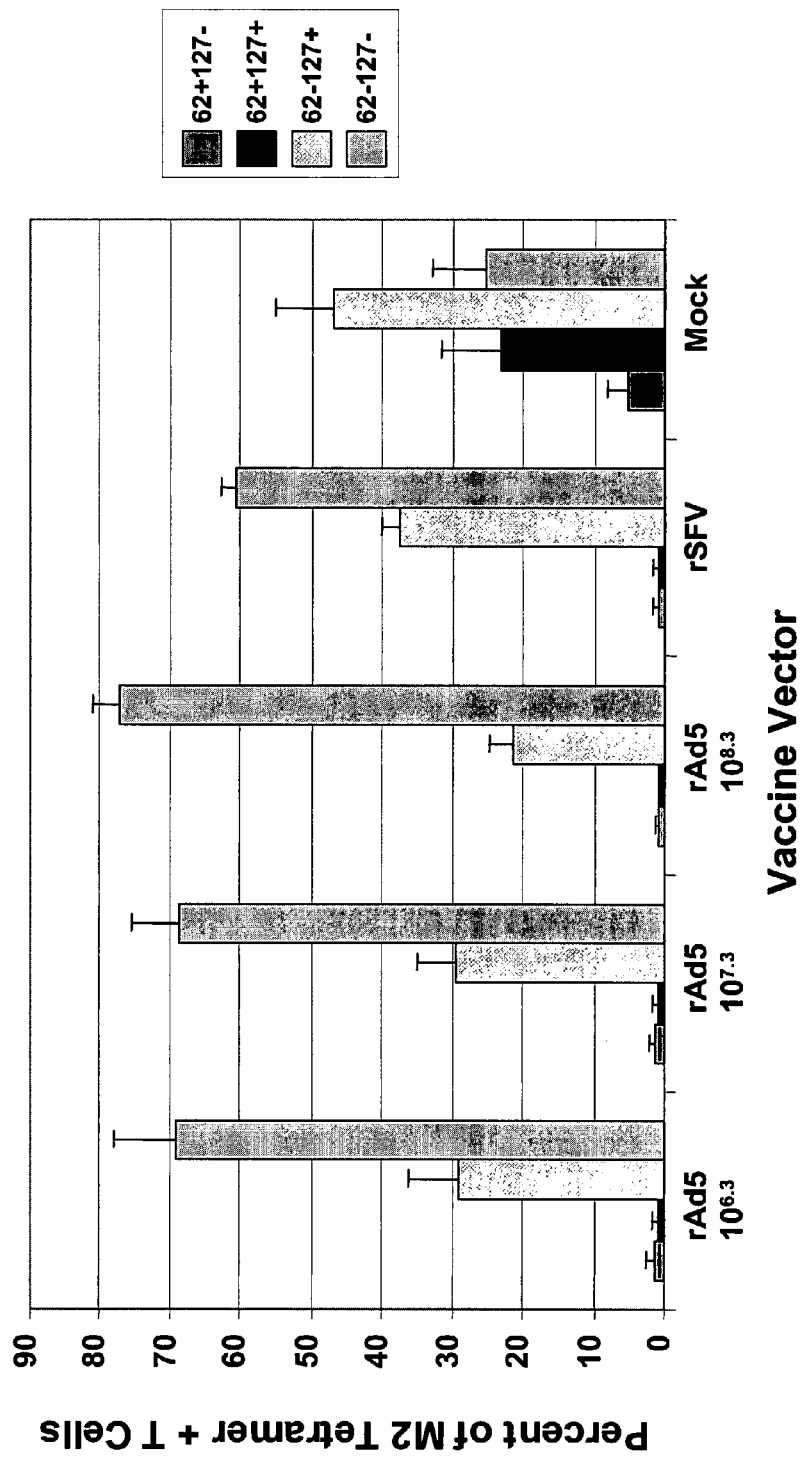
Figure 17B:
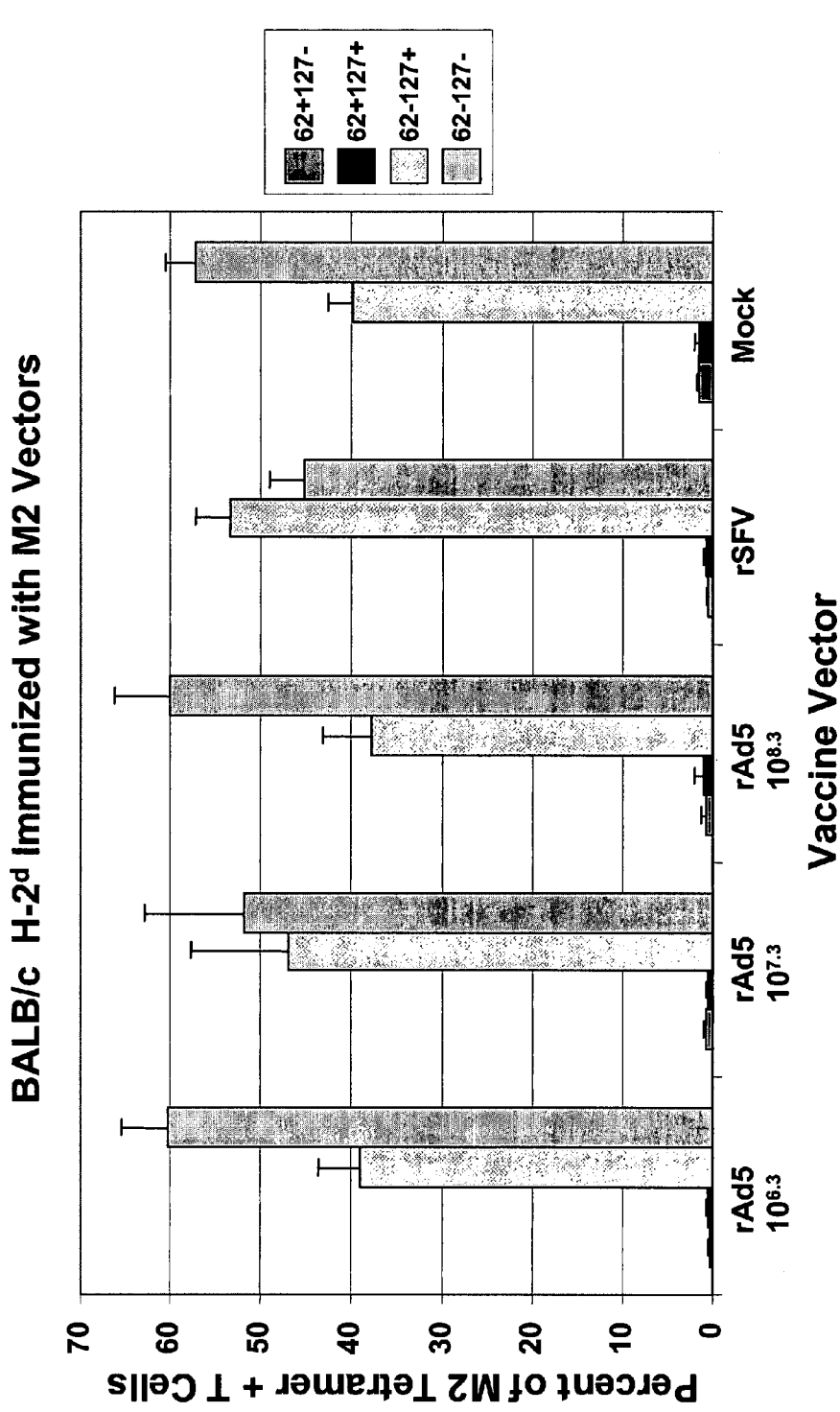

FIG. 16 (a and b). (a) is a graph showing M/M2-specific antibody Response by Kinetic ELISA. The graph shows a dose response effect of the rAd vector on the IgG2a isotype response. The pattern of IgG2a relative to IgG1 responses suggest an IFN-γ dominant response, FIG. 17 (a and b) is a graph showing the effector and memory phenotype of CD8+M2-specific T cells days 5 (a) and 10 (b) after RSV challenge of BALB/c mice immunized with Mock, rSFV, or various doses of rAd5 encoding M2.

Figure 18:
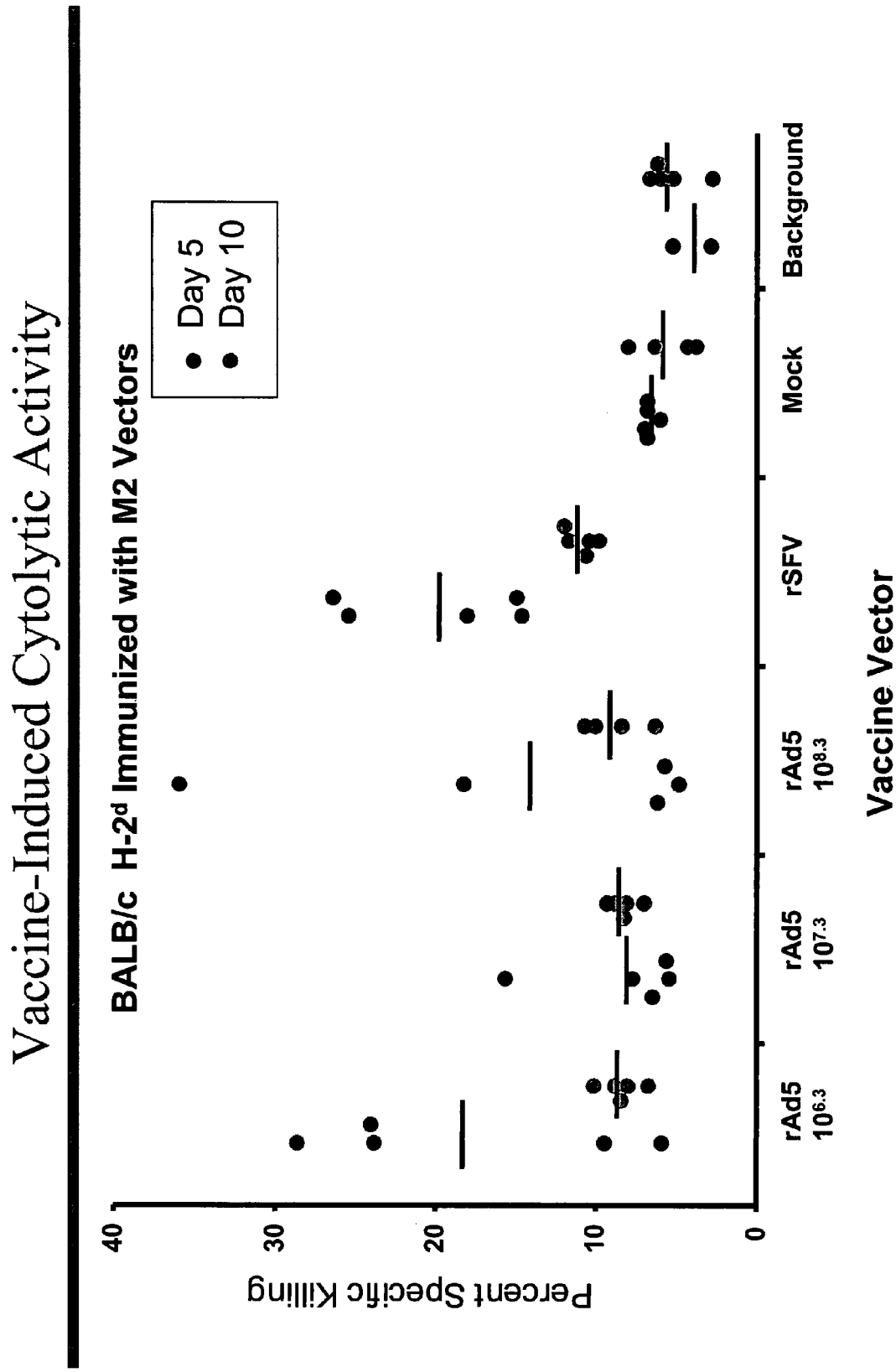

FIG. 18 is a graph that shows vaccine-induced cytolytic activity. BALB/c H-2d mice were immunized Mock, rSFV, or various doses of rAd5 ($10^{6.3}$ $10^{7.3}$ and $10^{8.3}$ PFU) encoding M2, and the percent specific killing was determined at day 5 and day 10 post RSV challenge were used.

Figure 19:
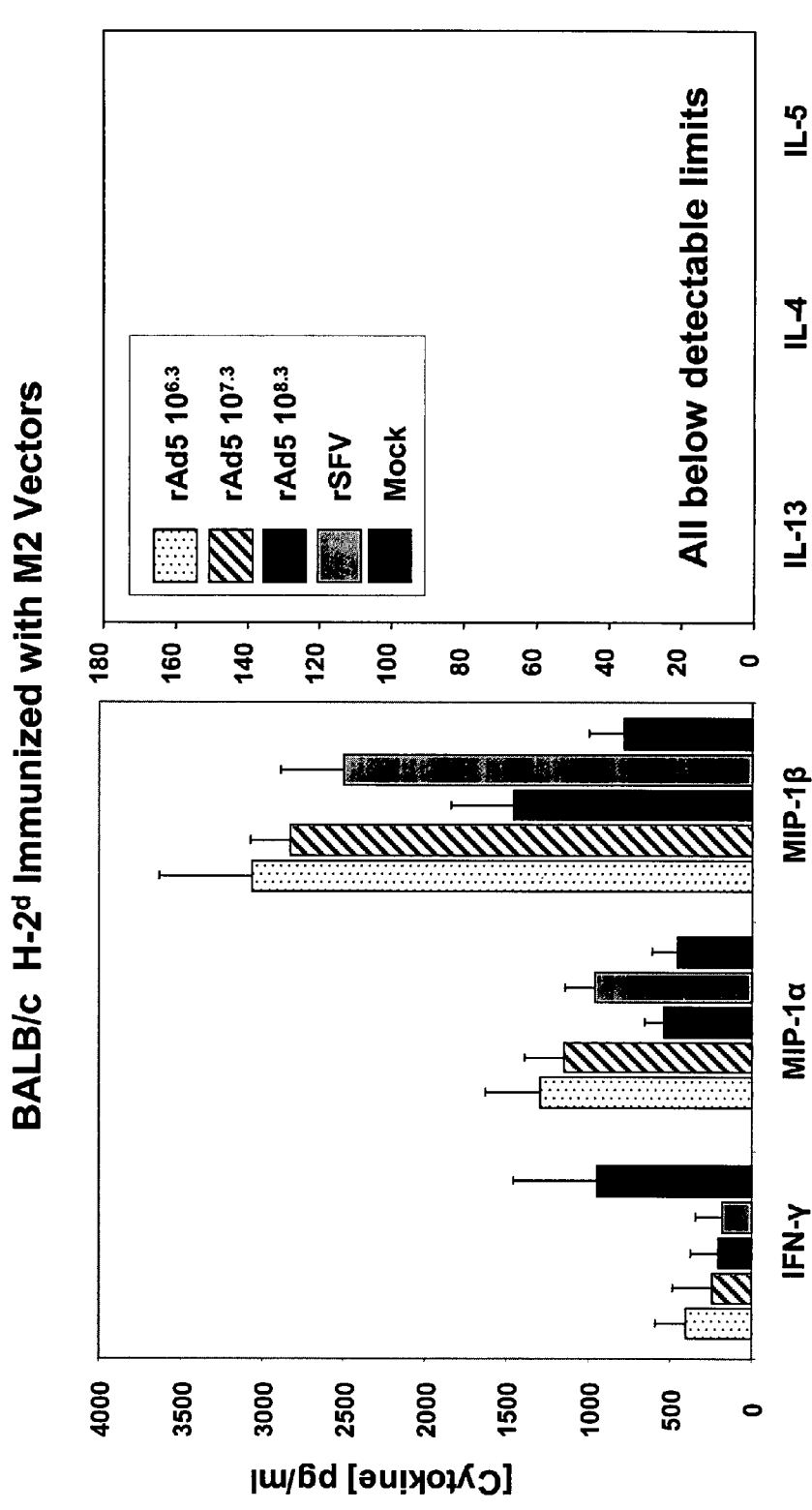

FIG. 19 shows two graphs demonstrating cytokine production in the lung day 5 post RSV challenge. BALB/c H-2d mice were immunized with M2 vectors. The graph on the left shows measurement of IFN-γ, MIP-1α and MIP-1β. The graph on the right shows measurement of IL-13, IL-14 and IL-5.

Figure 20A:
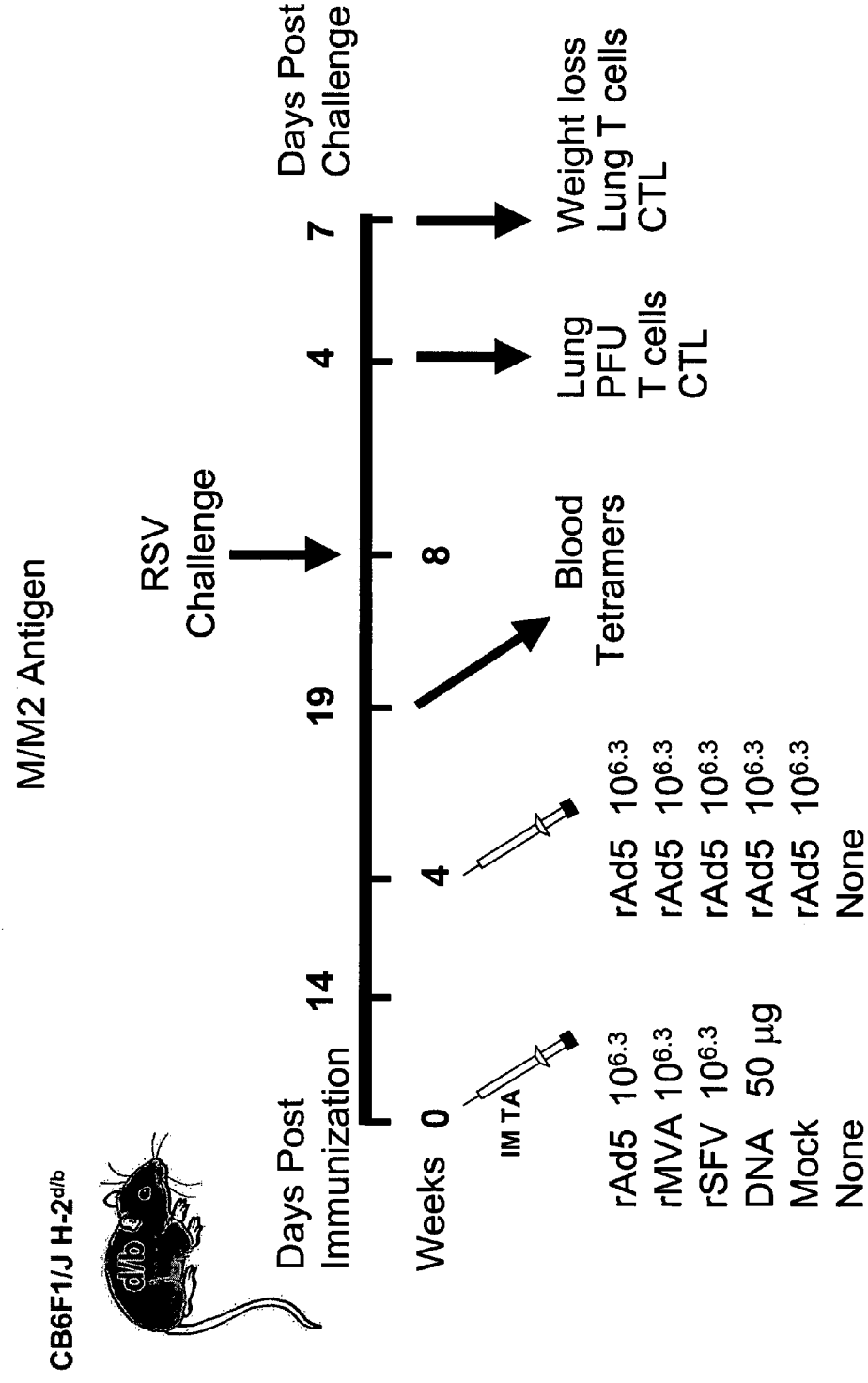
Figure 20B:
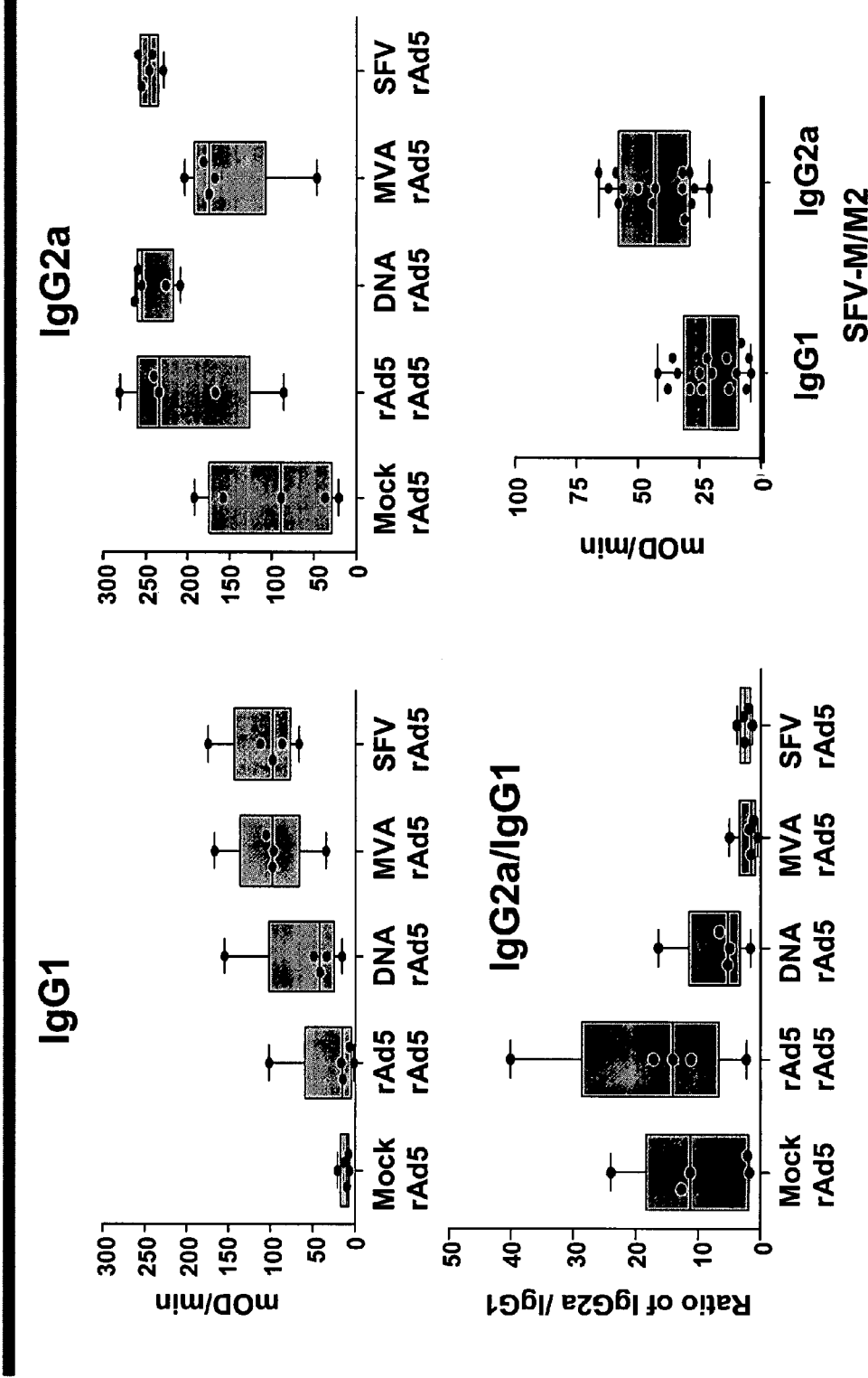

FIG. 20 (a and b). (a) is a schematic detailing the protocol schema. (b) is a panel of four graphs showing antibody response to vector immunization. CB6/F1J H-2 d/b mice were immunized with the indicated vectors all expressing the M/M2 gene. rAd5, DNA, rMVA, rSFV, and Mock vaccine vectors were compared in either homologous or heterologous prime-boost combinations. rAd5 given once or twice was compared to DNA, rMVA, or rSFV priming followed by rAd5 boosting. As shown in panel (b) while rAd5 only regimens induced antibody with the highest IgG2a/IgG1 ratio, the total antibody response was highest in the heterologous prime-boost groups.

Figure 21B:
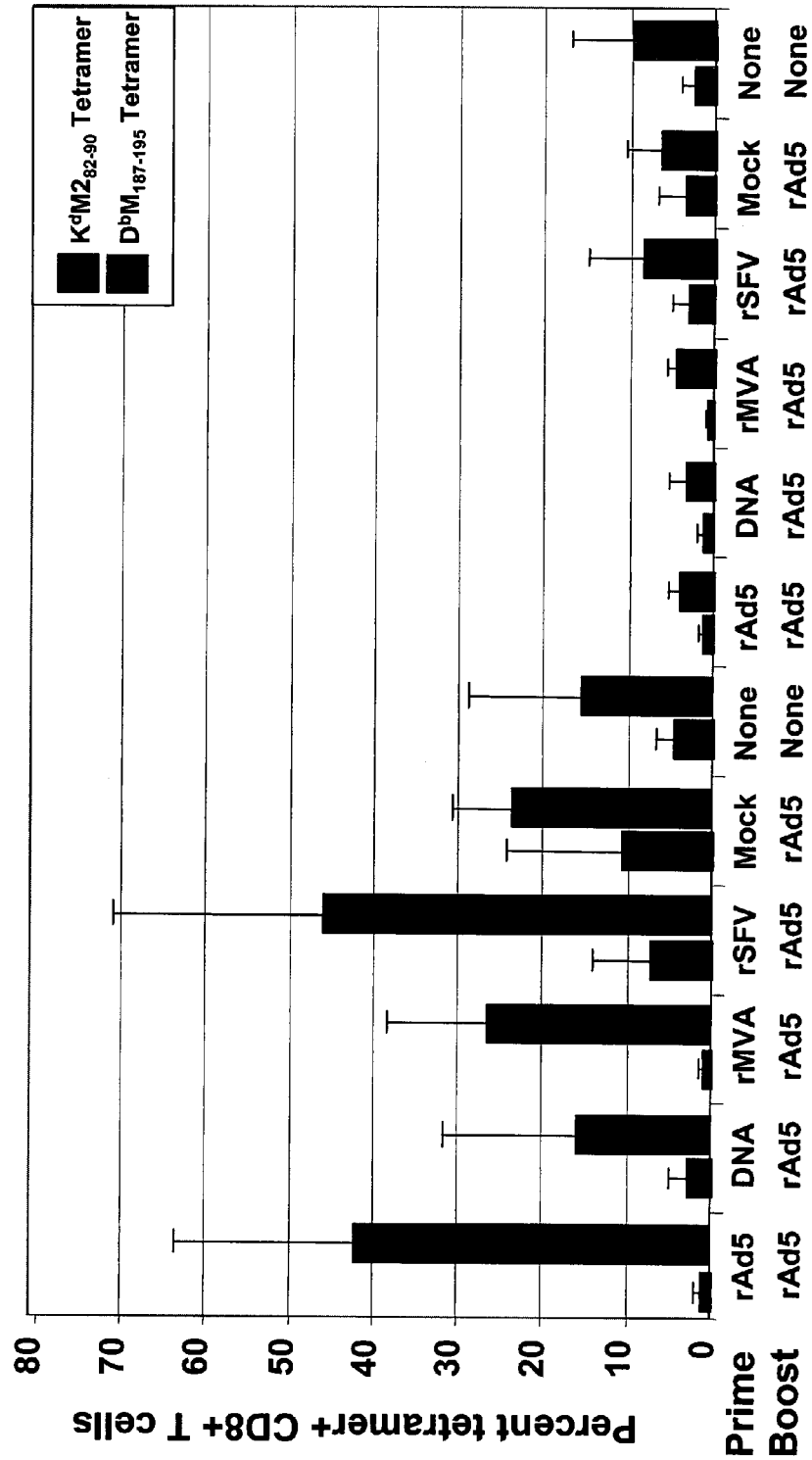
Figure 21C:
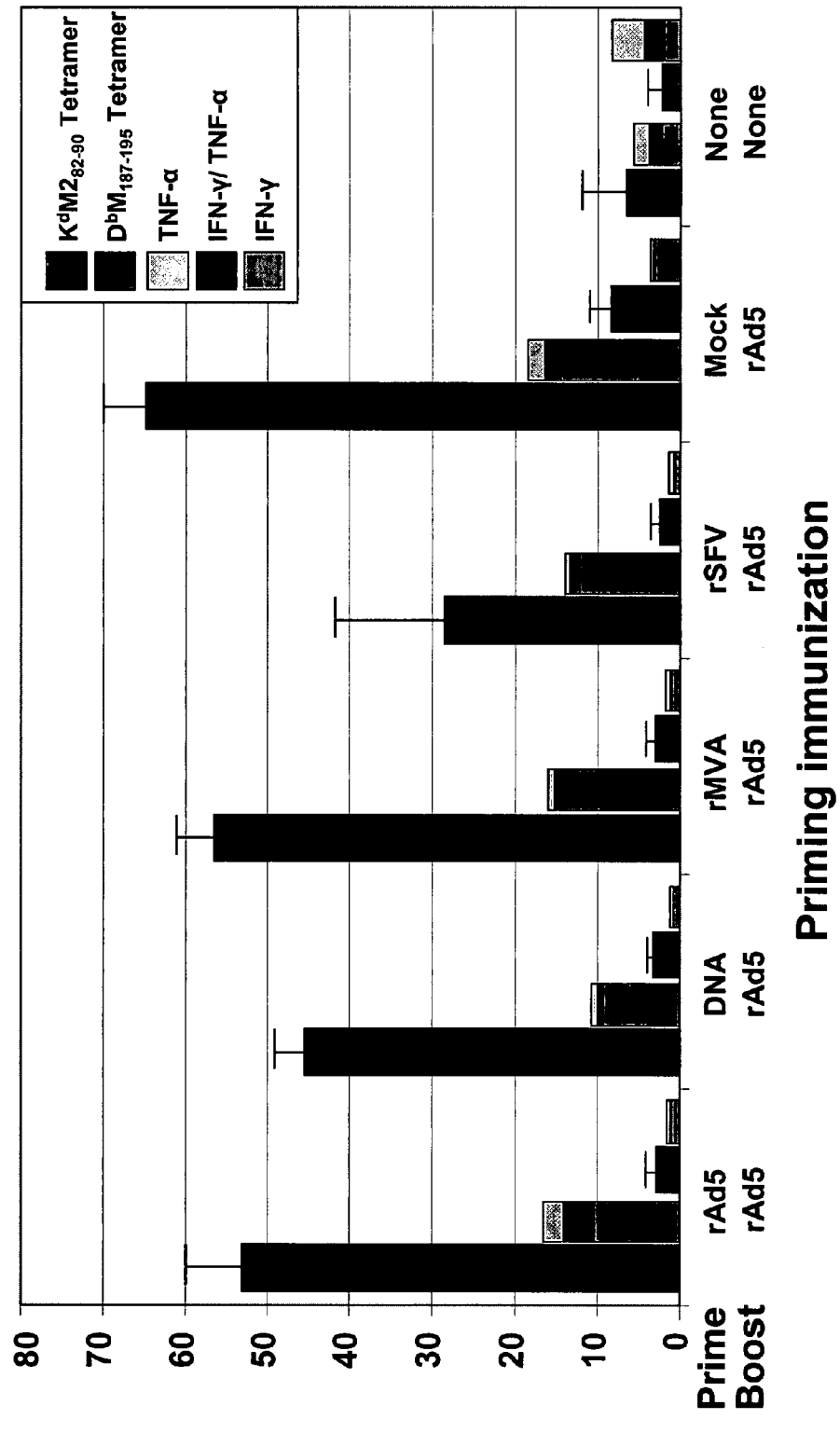

FIG. 21 (a-c). (a) is a graph showing virus replication in mice immunized with heterologous vectors indicating that heterologous prime-boost groups had the greatest reduction in RSV replication in lung after challenge. (b) is a graph showing tetramer+CD8+ T Cells in LN on Days 4 & 7 post challenge. (c) is a graph showing tetramer+CD8+ T Cells and ICS in lung on Day 7 post challenge. rAd5, DNA, rMVA, rSFV, and Mock vaccine vectors were used.

Figure 22:
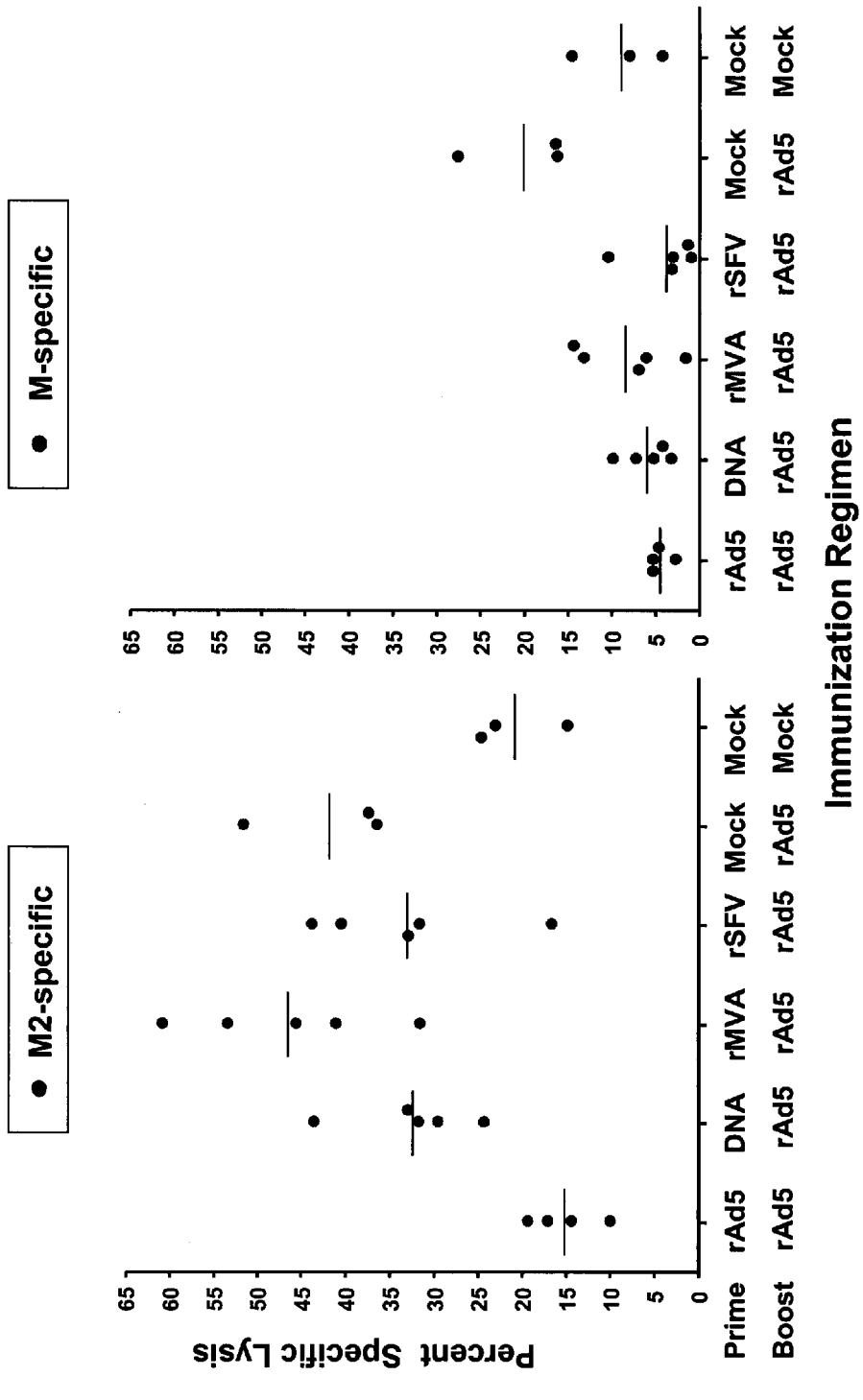

FIG. 22 is a graph showing cytolytic activity of vaccine vectors in Day 7 lung lymphocytes.

FIG. 23 is a graph showing correlation of CTL efficiency with reduced illness. The graph shows that heterologous vector prime-boost groups had higher relative cytolytic activity per individual tetramer+CD8+ T cell, and that this corresponded to reduced illness following RSV challenge.

Figure 24A:
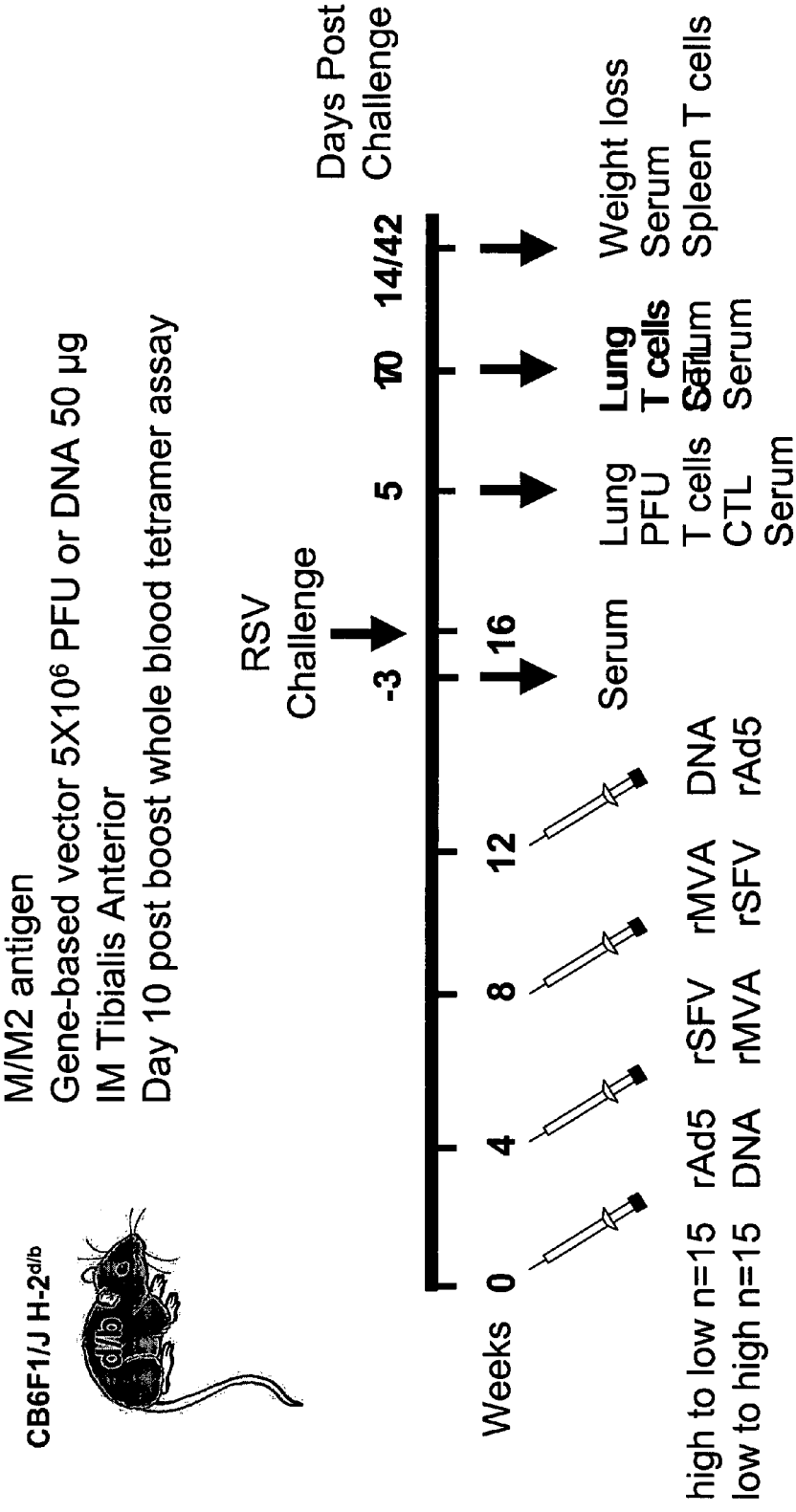

FIG. 24 (a and b). (a) is a schematic detailing the protocol schema. (b) is a graph showing weight loss after challenge with heterologous vectors. Weight loss is shown as percent of initial weight in days after infection.

FIG. 25 (a-d). (a) is four charts showing phenotype of tetramer-positive CD8+ T Cells after heterologous boosting. (b) is a graph showing tetramer+CD8+ T Cells on Days 5 & 7. (c) is two graphs showing cytolytic activity in Day 5 lung lymphocytes. (d) is a graph showing T regulatory cells in lung post challenge Days 5 & 7. The data suggests that repeated heterologous vector boosting results in a population of highly cytolytic CD8+ effector T cells that are associated with a significant reduction in T regulatory cells.

Figure 26A:
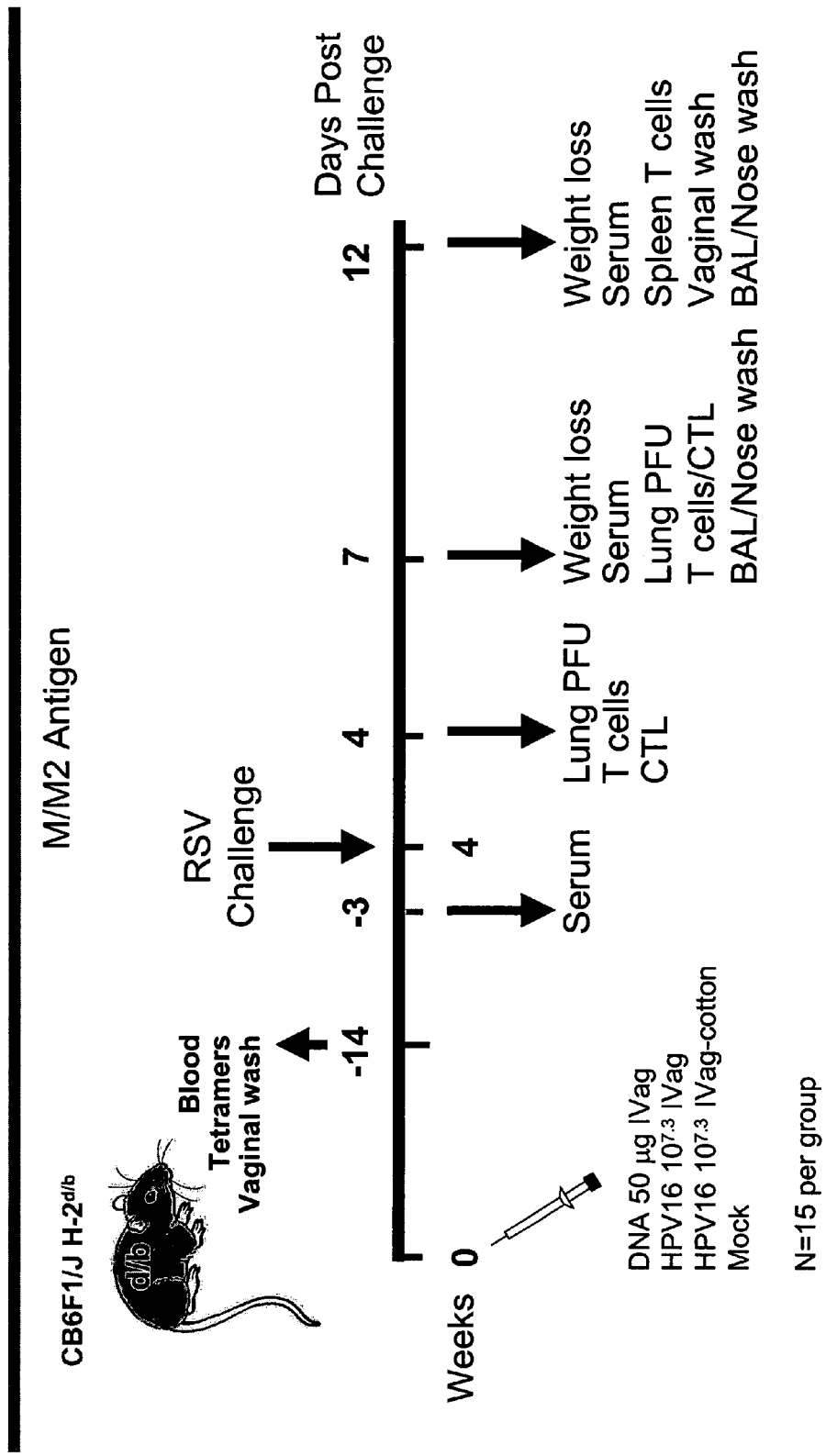
Figure 26B:
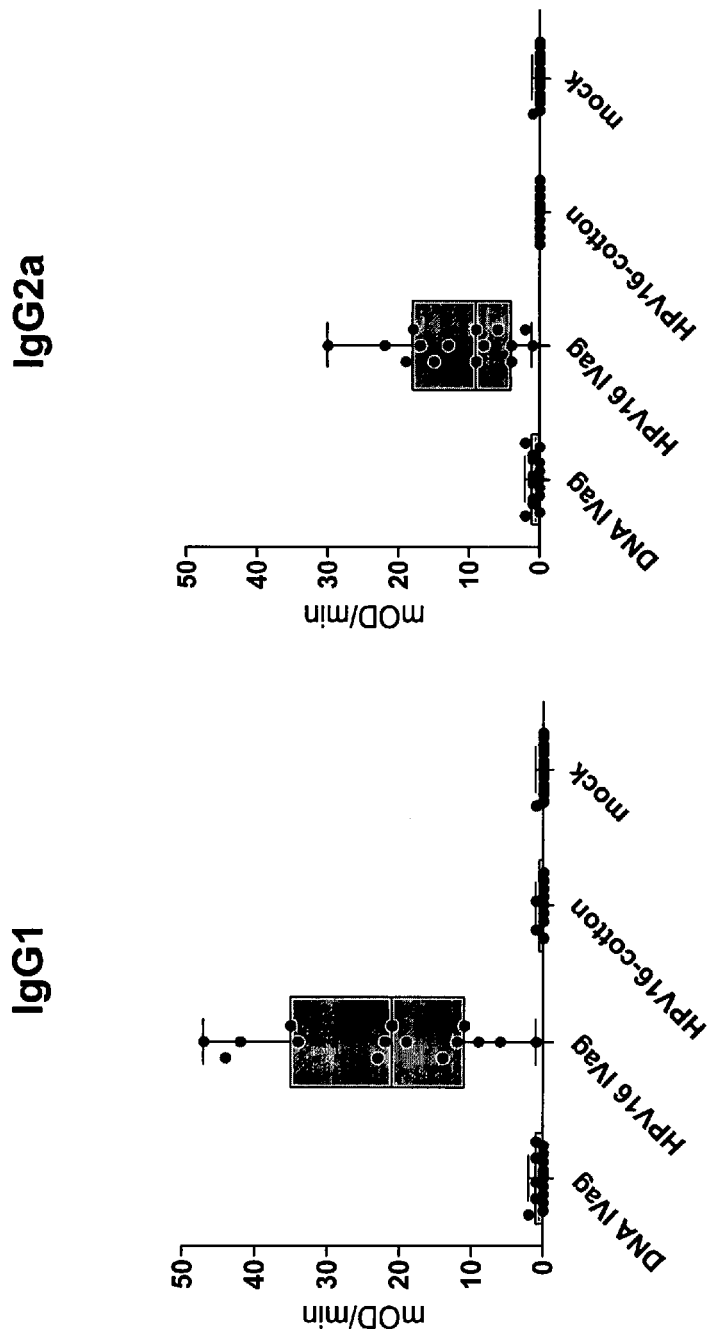

FIG. 26 (a and b). (a) is a schematic detailing the protocol schema. (b) are two graphs showing pre challenge serum levels of IgG1 and IgG2a. The graph on the left shows measurement of IgG1. The graph on the right shows measurement of IgG2a.

FIG. 27 (a and b). (a) is a graph showing weight loss as percent of baseline in the days after challenge. (b) is a graph showing tetramer+CD8+ T Cells in Lung Days 4, 7, & 12 Post Challenge. These data indicate that a single dose of naked DNA or DNA packaged in a HPV particle can induce both antibody and T cell responses to the RSV M/M2 antigen expressed by the DNA plasmid.

FIG. 28 shows the amino acid sequence of the original (SEQ ID NO: 1) and the nucleotide sequence of the codon modified RSV membrane anchored attachment glycoprotein (Gr) gene (SEQ ID NO: 2).

FIG. 29 shows the amino acid sequence of the original (SEQ ID NO: 3) and the nucleotide sequence of the codon modified RSV matrix glycoprotein (M) gene (SEQ ID NO: 4).

FIG. 30 shows the amino acid sequence of the original (SEQ ID NO: 5) and the nucleotide sequence of the codon modified RSV matrix glycoprotein (M2) gene (SEQ ID NO: 6).

FIG. 31A and FIG. 31B show the amino acid sequence of the nucleotide sequence of the retained codon modified attachment glycoprotein (G) (SEQ ID NO: 7); and the nucleotide sequence of the codon modified RSV matrix glycoprotein fusion (M/M2) gene (SEQ ID NO: 8).

FIG. 32 shows the amino acid sequence of the original (SEQ ID NO: 9) and the nucleotide sequence of the codon modified RSV envelope nucleoprotein (N) gene (SEQ ID NO: 10).

FIG. 33 shows the amino acid sequence of the original (SEQ ID NO: 11) and the nucleotide sequence of the codon modified RSV envelope glycoprotein (SH) gene (SEQ ID NO: 12).

FIG. 34A, FIG. 34B, FIG. 34C, and FIG. 34D show the amino acid sequence of the original (SEQ ID NO: 13), a modified (SEQ ID NO: 16) and the corresponding nucleotide sequences of the codon-modified RSV fusion glycoprotein (F) genes (SEQ ID NOs: 14, 16 and 17, respectively).

FIG. 35 shows amino acid sequence of the retained membrane attachment glycoprotein (G) (SEQ ID NO: 15).

DETAILED DESCRIPTION OF THE INVENTION

The invention generally features immunogenic compositions comprising codon modified viral genes or fragments. More specifically, the codon modified genes or fragments encode viral glycoproteins or fragments. The codon modified genes or fragments, as described herein, are useful in methods of eliciting an immune response to prevent viral infection in a subject. The methods are useful in treating a subject having a viral infection, and in preventing a viral infection. In particular examples, the methods are useful for preventing or treating, for example, Paramyxoviral infection.

Definitions

In this disclosure, "comprises," "comprising," "containing" and "having" and the like can have the meaning ascribed to them in U.S. Patent law and can mean "includes," "including," and the like; "consisting essentially" of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "cytokine" is meant to refer to a generic term for extracellular proteins or peptides that mediate cell-cell communication, often with the effect of altering the activation state of cells.

The term "codon" refers to a sequence of three adjacent nucleotides that constitute the genetic code that determines the insertion of a specific amino acid in a polypeptide chain during protein synthesis or the signal to stop protein synthesis.

The term "codon-modification" or "a codon modified sequence" is meant to refer to a molecular biology strategy wherein specific coding sequences are re-designed for maximal gene expression in a specific organism (e.g. human, mouse, bacteria, etc.). Codon modification may be used to overcome poor gene expression, for example to increase expression and optimization of immunostimulatory signals or to remove cryptic splice sites.

The term "fragment" is meant to refer to a portion of a protein or nucleic acid that is substantially identical to a reference protein or nucleic acid. In some embodiments the fragment is a fragment of a codon-modified gene. In some embodiments the portion can retain at least 50%, 75%, or 80%, or more preferably 90%, 95%, or even 99% of the biological activity of the reference protein or nucleic acid described herein. In other embodiments, the fragment comprises at least 5, 10, 11, 12, 13, 14, 15, 16, 17, 18, 19, or 20 amino acids of a reference protein or is a nucleic acid molecule encoding such a fragment.

The term "analog" as used herein is meant to refer to a polypeptide that possesses a similar or identical function as a RSV polypeptide, a fragment of a RSV polypeptide, or an anti-RSV antibody but does not necessarily comprise a similar or identical amino acid sequence of a RSV polypeptide, a fragment of a RSV polypeptide, or an anti-RSV antibody, or possess a similar or identical structure of a RSV polypeptide, a fragment of a RSV polypeptide, or an antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a RSV polypeptide, a fragment of a RSV polypeptide, or an antibody described herein; (b) a polypeptide encoded by a nucleotide sequence that hybridizes under stringent conditions to a nucleotide sequence encoding a RSV polypeptide, a fragment of a RSV polypeptide, or an antibody described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues (see, e.g., Maniatis et al. (1982) Molecular Cloning: A Laboratory Manual, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a RSV polypeptide, a fragment of a RSV polypeptide, or an antibody described herein. A polypeptide with similar structure to a RSV polypeptide, a fragment of a RSV polypeptide, or an antibody described herein refers to a polypeptide that has a similar secondary, tertiary or quaternary structure of a RSV polypeptide, a fragment of a RSV, or an antibody described herein. The structure of a polypeptide can be determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih-.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The term "elderly" as used herein is meant to refer to a human subject who is age 65 or older.

The term "host" as used herein refers to an animal, preferably a mammal, and most preferably a human.

The term "host cell" means a cell which contains a heterologous nucleic acid, such as a vector, and supports the replication and/or expression of the nucleic acid. Host cells can be prokaryotic cells such as E. coli, or eukaryotic cells such as yeast, insect, amphibian, avian or mammalian cells, including human cells. Exemplary host cells in the context of the invention include 293ORF6, PERC.6, CHO, HEp-2, HeLa, BSC40, Vero, BHK-21, 293, C12 immortalized cell lines and primary mouse or human dendritic cells. In particular examples, 293ORF6 and PERC.6 are the two cell lines used to produce recombinant adenovirus vectors.

The term "human infant" as used herein refers to a human less than 24 months, preferably less than 16 months, less than 12 months, less than 6 months, less than 3 months, less than 2 months, or less than 1 month of age.

The term "immune response" refers to the process whereby inflammatory cells are recruited from the blood to lymphoid as well as non-lymphoid tissues via a multifactorial process that involves distinct adhesive and activation steps. Inflammatory conditions cause the release of chemokines and other factors that, by upregulating and activating adhesion molecules on inflammatory cells, promote adhesion, morphological changes, and extravasation concurrent with chemotaxis through the tissues.

The term "immunogenic composition" and variations thereof, as used herein is meant to refer to a composition that modulates a host's immune system. In certain embodiments, an immunogenic composition is an immunosuppressant composition. In certain other embodiments, an immunogenic composition is an immunostimulatory composition. Immunogenic compositions include, but are not limited to, viruses, small molecules, peptides, polypeptides, proteins, fusion proteins, antibodies, inorganic molecules, mimetic agents, and organic molecules. Not included in immunogenic compositions are live, attenuated viruses.

The term "in combination" in the context of the administration of other therapies is meant to refer to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a Paramyxoviral infection, or a condition related thereto. Any additional therapy can be administered in any order with the other additional therapies. In certain embodiments, the antibodies of the invention can be administered in combination with one or more therapies (e.g., therapies that are not the antibodies of the invention) that are currently administered to prevent, treat, manage, and/or ameliorate a Paramyxoviral infection (e.g., acute RSV disease or a RSV or other symptom related thereto). Non-limiting examples of therapies that can be administered in combination with an antibody of the invention include analgesic agents, anesthetic agents, antibiotics, or immunomodulatory agents or any other agent listed in the U.S. Pharmacopoeia and/or Physician's Desk Reference.

As used herein, the terms "infection" and "RSV infection" refer to all stages of RSV's life cycle in a host (including, but not limited to the invasion by and replication of RSV in a cell or body tissue), as well as the pathological state resulting from the invasion by and replication of a RSV. The invasion by and multiplication of RSV includes, but is not limited to, the following steps: the docking of the RSV particle to a cell, fusion of a virus with a cell membrane, the introduction of viral genetic information into a cell, the expression of RSV proteins, the production of new RSV particles and the release of RSV particles from a cell. An RSV infection may be an upper respiratory tract RSV infection (URI), a lower respiratory tract RSV infection (LRI), or a combination thereof. In specific embodiments, the pathological state resulting from the invasion by and replication of RSV is an acute RSV disease. The term "acute RSV disease" as used herein refers to clinically significant disease in the lungs or lower respiratory tract as a result of an RSV infection, which can manifest as pneumonia and/or bronchiolitis, where such symptoms may include hypoxia, apnea, respiratory distress, rapid breathing, wheezing, cyanosis, etc. Acute RSV disease requires an affected individual to obtain medical intervention, such as hospitalization, administration of oxygen, intubation and/or ventilation.

The term "pharmaceutically acceptable" as used herein means being approved by a regulatory agency of the Federal or a state government, or listed in the U.S. Pharmacopia, European Pharmacopia or other generally recognized pharmacopia for use in animals, and more particularly in humans.

The term "promoter" refers to a DNA sequence that is recognized by RNA polymerase and initiates transcription.

By "subject" is meant a mammal, such as a human patient or an animal (e.g., a rodent, bovine, equine, porcine, ovine, canine, feline, ferret, or other domestic mammal).

The term "vector" is meant to refer to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are replication defective viral vectors such as recombinant adenovirus, but replication-competent viral vectors, mycobacterial vectors, bacterial vectors, or others including DNA plasmids or RNA could be used.

The term "vector priming" is meant to refer to the delivery of a gene encoding a vaccine antigen by way of an expression vector. In certain embodiments, it means that the vector-based gene delivery will be a first exposure to the vaccine antigen, followed by one or more subsequent "booster" dose or doses of vaccine.

The term "expression vector" is meant to refer to a vector, such as a plasmid or viral particle, which is capable of promoting expression as well as replication of a foreign or heterologous nucleic acid incorporated therein. Typically, the nucleic acid to be expressed is "operably linked" to a promoter and/or enhancer, and is subject to transcription regulatory control by the promoter and/or enhancer.

Viral Pathogens
Family Paramyxoviridae

Virus families containing enveloped single-stranded RNA of the negative-sense genome are classified into groups having non-segmented genomes (e.g., Paramyxoviridae, Rhabdoviridae) or those having segmented genomes (e.g., Orthomyxoviridea, Bunyaviridae, Arenaviridae). Viruses of family Paramyxoviridae have been classified into two subfamilies and several genera (e.g., as described in the Universal Virus Database of the International Committee of Taxonomy of Viruses, found on the world wide wed at ncbi.nlm.nih.gov/ICTV-db). Subfamily Paramyxovirinae includes the Respirovirus genus (e.g., Sendai virus, bovine parainfluenza virus 3, human parainfluenza viruses 1 and 3, simian virus 10), the Rubulavirus genus (e.g., mumps virus, human parainfluenza viruses 2 and 4, Mapuera virus, porcine rubulavirus, La-Piedad-Michoacan-Mexico virus, simian parainfluenza virus 5), the Morbillivirus genus (e.g., measles virus, canine distemper virus, cetacean morbillivirus, Edmonston virus, Peste-des-petits-ruminants virus, Rinderpest virus), the Henipavirus genus (e.g., Hendra virus, Nipah virus), the Avulavirus genus (Newcastle disease virus, avian parainfluenza viruses 1-9), and the "TPMV-like viruses" genus (e.g., Tupaia virus). Subfamily Pneumovirinae includes the Pneumovirus genus (e.g., murine pneumonia virus, bovine RSV, human RSV (e.g., subgroups A2, B1, S2)) and the Metapneumovirus genus (e.g., Turkey rhinotracheitis virus). The family also includes Fer-de-Lance virus and Nariva virus.

Negative strand RNA viruses can be genetically engineered and recovered using a recombinant reverse genetics approach (U.S. Pat. No. 5,166,057 to Palese et al.). Although this method was originally applied to engineer influenza viral genomes (Luytjes et al. 1989, Cell 59:1107-1113; Enami et al., 1990, Proc. Natl. Acad. Sci. USA 92:11563-11567), it has been successfully applied to a wide variety of segmented and nonsegmented negative strand RNA viruses, e.g., rabies (Schnell et al. 1994, EMBO J. 13:4195-4203); VSV (Lawson et al. 1995, Proc. Natl. Acad. Sci. USA 92:4477-4481); measles virus (Radecke et al. 1995, EMBO J. 14:5773-5784); rinderpest virus (Baron & Barrett, 1997, J. Virol. 71:1265-1271); human parainfluenza virus (Hoffman & Banerjee, 1997, J. Virol. 71:3272-3277; Dubin et al., 1997, Virology 235:323-332); SV5 (He et al., 1997, Virology 237:249-260); canine distemper virus (Gassen et al., 2000, J. Virol. 74:10737-44); and Sendai virus (Park et al., 1991, Proc. Natl. Acad. Sci. USA 88:5537-5541; Kato et al., 1996, Genes to Cells 1:569-579). Rescue of RSV has been described e.g., in Collins et al., U.S. Pat. Nos. 6,264,957 and 6,790,449, and WO 97/12032; Jin et al. (1998) Virology 251:206-214; and WO 02/44334 by Jin et al., entitled "Recombinant RSV virus expression systems and vaccines," and is briefly described herein. (See also e.g., Jin et al. (2000) J. Virol. 74:74-82; Jin et al. (2000) Virology 273:210-218; Cheng et al. (2001) Virology 283:59-68; and Tang et al. (2001) J. Virol. 75: 11328-11335.) Methods for propagation, separation from host cell cellular components, and/or further purification of viruses of family Paramyxoviridae are well known to those skilled in the art.

In general, the major human viruses of the Paramyxoviridae family are: measles virus, mumps virus, the parainfluenza viruses (types 1, 2, 3, 4a, and 4b), and respiratory syncytial virus (RSV).

All of the viruses of the Paramyxoviridae family are spread through the respiratory route and are highly contagious.

Disease caused by the measles virus is typically marked by a prodrome of fever, conjunctivitis, coryza, and cough which is followed by the development of a rash of flat macules which first appear on the head and then move to the chest, trunk, and limbs. These macules typically fuse resulting in large blotches that can be slow to fade. Two serious complications of measles infection are acute postinfectious encephalitis, which occurs in about 1 in every 1,000 cases, and subacute sclerosing panencephalitis (SSPE), which occurs in about 1 in every 300,000 cases. Postinfectious encephalitis usually develops during the first week following development of the rash, has a mortality rate of 15%, and survivors typically have neurologic sequelae. SSPE, on the other hand, develops years (typically 7-10) following infection with the measles virus and is always fatal.

Infection with mumps virus typically results in a minor illness characterized by parotitis, or inflammation of the salivary glands. However, mumps in postpubertal males can result in orchitis, or inflammation of the testes, a painful condition which can result in destruction of the testicular tissue. Furthermore, mumps is the most common cause of meningitis. One serious, yet rare, complication of mumps infection is mumps encephalitis which can result in unilateral nerve deafness.

Parainfluenza viruses are common respiratory pathogens of humans that typically produce minor upper respiratory tract infections which are characterized by coryza, pharyngitis, low fever, and bronchitis. Parainfluenza viruses are also the most common cause of croup, or laryngotracheobronchitis, in children aged 6 months to 5 years. Croup is marked by fever, cough, respiratory distress, and stridor. In extreme cases, laryngeal obstruction can occur. Finally, parainfluenza viruses are also capable of causing bronchiolitis and/or pneumonia in children under the age of 6 months. It should be noted that croup and pneumonia occur in only 2-3% of cases.
Respiratory Syncytial Virus (RSV)

Respiratory infections are common infections of the upper respiratory tract (e.g., nose, ears, sinuses, and throat) and lower respiratory tract (e.g., trachea, bronchial tubes, and lungs). Symptoms of upper respiratory infection include runny or stuffy nose, irritability, restlessness, poor appetite, decreased activity level, coughing, and fever. Viral upper respiratory infections cause and/or are associated with sore throats, colds, croup, and the flu. Clinical manifestations of a lower respiratory infection include shallow coughing that produces sputum in the lungs, fever, and difficulty breathing.

Among the challenges for RSV vaccine development is the young age of onset of serious disease. Human RSV is the leading cause of hospitalization for viral respiratory tract disease in infants and young children worldwide, as well as a significant source of morbidity and mortality in immunocompromised adults and in the elderly. Natural immunity does not protect against reinfection with RSV, thus presenting another challenge in vaccine design. To date, no vaccines have been approved which are able to prevent the diseases associated with RSV infection. The legacy of vaccine enhanced disease presents another challenge to RSV vaccine development. RSV may be linked to epidemics of asthma and has been identified as an exacerbating factor in nephrotic disease, cystic fibrosis, and opportunistic infections in the immunocompromised. RSV is a major cause of bronchiolitis, pneumonia, mechanical ventilation, and respiratory failure in infants in the United States. By the age of two, almost all children have been infected with RSV, and most have been infected twice. Further, children who have been hospitalized in infancy with RSV bronchiolitis are at significantly increased risk of childhood asthma and allergy (Sigurs N et al. Am J Respir Crit. Care Med 171: 137-142. 2005) until the time they reach the age of 13 years (Stein R T et al. Lancet 354:541-545, 1999). RSV is a major cause of respiratory illness in the elderly and high-risk adults. RSV infection in the elderly population causes up to 14% of community-acquired pneumonia, especially in those with underlying cardiopulmonary disease. Bone marrow transplant patients develop lower respiratory tract disease with RSV, which carries a mortality of up to 50%.

While a vaccine or commercially available effective treatment are not yet available, some success has been achieved in the area of prevention for infants at high risk of serious lower respiratory tract disease caused by RSV, as well as a reduction of lower respiratory infection (LRI). In particular, there are two immunoglobulin-based therapies approved to protect high-risk infants from serious LRI: RSV-IGIV (RSV-immunoglobulin intravenous) and palivizumab. However, neither RSV-IGIV nor palivizumab has been approved for use other than as a prophylactic agent for serious lower respiratory tract acute RSV disease. Although RSV-IVIG and palivizumab represent significant advances in the prevention of lower respiratory tract acute RSV disease and mitigation of lower respiratory tract infection, neither has demonstrated efficacy at permissible doses against the virus in the upper respiratory tract and therefore the possible prevention of progression of RSV infection to the lower respiratory tract. In fact, RSV-IVIG failed to clear nasal RSV when administered as a nasal spray in amounts that were effective to clear pulmonary RSV in every animal of the treatment group (Prince et al., U.S. Pat. No. 4,800,078, issued Jan. 24, 1989). The intraperitoneal route of administration also failed to clear RSV from the upper respiratory tract with the same efficacy as the lower respiratory tract. It has recently been noted that the immune response elicited by upper respiratory tract infections differs from that induced by lower respiratory infections (van Benten I. J. et al., J. Med. Virol. 2003 October; 71(2):290-7). Thus, a need exists for the prevention of acute RSV disease in the lungs via treatment of RSV URI and/or prevention and/or reduction of the progression of the virus to the lower respiratory tract.

The structure and composition of RSV has been elucidated and can be found described in detail in the textbook "Fields Virology", Fields, B. N. et al. Raven Press, N.Y. (1996), in particular, Chapter 44, pp 1313-1351 "Respiratory Syncytial Virus" by Collins, P., McIntosh, K., and Chanock, R. M. (Collins, P., McIntosh, K., and Chanock, R. M. in "Fields Virology" ed. by Fields, B. N., Knipe, D. M., and Howley, P. M., Lippincott-Raven Press, New York, (1996) pp. 1313-1351), both of which are incorporated by reference herein in their entireties.

RSV is classified in the Pneumovirus genus of the Paramyxoviridae family (Collins et al. (2001) Respiratory syncytial virus. pp. 1443-1485. In; Knipe & Howley (eds.) Fields Virology vol. 1. Lippincott, Williams & Wilkins, Philadelphia; Lamb & Kolakofsky (2001) Paramyxoviridae: the viruses and their replication. pp. 1305-1340. In; Knipe & Howley (eds.) Fields Virology vol. 1. Lippincott, Williams & Wilkins, Philadelphia). A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in Mink et al., Virology 185: 615-624 (1991), Stec et al., Virology 183: 273-287 (1991), and Connors et al., Virol. 208:478-484 (1995), incorporated herein by reference.

The nucleocapsid protein (N), phosphoprotein (P), and large polymerase protein (L) constitute the minimal components for viral RNA replication and transcription in vitro (Grosfield et al. (1995) J. Virol. 69: 5677-5686; Yu et al. (1995) J. Virol. 69: 2412-2419; and Collins et al., U.S. Pat. Nos. 6,264,957 and 6,790,449, and WO 97/12032). The N protein associates with the genomic RNA to form the nucleocapsid, which serves as the template for RNA synthesis. The L protein is a multifunctional protein that contains RNA-dependent RNA polymerase catalytic motifs and is also probably responsible for capping and polyadenylation of viral mRNAs. However, the L protein alone is not sufficient for the polymerase function; the P protein is also required. Transcription and replication of RSV RNA are also modulated by the M2-1, M2-2, NS1, and NS2 proteins that are unique to the pneumoviruses. M2-1 is a transcription antitermination factor required for processive RNA synthesis and transcription read-through at gene junctions (Collins et al. (2001) in D. M. Knipe et al. (eds.), Fields Virology, 4.sup.th ed. Lippincott, Philadelphia; Hardy et al. (1999) J. Virol. 73:170-176; Hardy & Wertz (1998) J. Virol. 72:520-526). M2 (ORF1) is also known as RNA polymerase elongation factor and is also needed for the recovery of infectious RSV. M2-2 is involved in the switch between viral RNA transcription and replication (Bermingham & Collins (1999) Proc. Natl. Acad. Sci. USA 96:11259-11264; Jin et al. (2000) J. Virol. 74:74-82). NS1 and NS2 have been shown to inhibit minigenome synthesis in vitro (Atreya et al. (1998) J. Virol. 72:1452-1461).

The G and F proteins are the two major surface antigens that elicit anti-RSV neutralizing antibodies to provide protective immunity against RSV infection and reinfection. High levels of circulating antibodies correlate with protection against RSV infections or reduction of disease severity (Crowe (1999) Microbiol. Immunol. 236:191-214). Two antigenic RSV subgroups have been recognized based on virus antigenic and sequence divergence (Anderson et al. (1985) J. Infect. Dis. 151:626-633; Mufson et al. (1985) J. Gen. Virol. 66:2111-2124). This antigenic diversity may be partly responsible for repeated RSV infection.

The two major protective antigens of RSV are the envelope fusion (F) and attachment (G, also referred to as Gr) glycoproteins (Walsh, E. E., Hall, C. B., Briselli, M., Brandiss, M. W. and Schlesinger, J. J. (1987) J. Infect. Dis. 155, 1198-1204). The F protein is synthesized as an about 68 kDa precursor molecule ($F_0$) which is proteolytically cleaved into disulfide-linked $F_1$ (about 48 kDa) and $F_2$ (about 20 kDa) polypeptide fragments (Walsh, E. E., Hruska, J. (1983) J. Virol. 47, 171-177). The G protein (about 33 kDa) is heavily O-glycosylated giving rise to a glycoprotein of apparent molecular weight of about 90 kDa (Levine, S., Kleiber-France, R., and Paradiso, P. R. (1987) J. Gen. Virol. 69, 2521-2524). Two broad subtypes of RSV have been defined A and B (ref. 15). The major antigenic differences between these subtypes are found in the G glycoprotein while the F glycoprotein is more conserved (Wertz, G. W., Sullender, W. M. (1992) Biotech. 20, 151-176; Johnson, P. R., Olmsted, R. A., Prince, G. A., Murphy, B. R., Alling, D. W., Walsh, E. E. and Collins, P. L. (1987) J. Virol. 61 (10), 3163-3166).

In addition to the antibody response generated by the F and G glycoproteins, human cytotoxic T cells produced by RSV infection have been shown to recognize the RSV F protein, matrix protein M, nucleoprotein N, small hydrophobic protein SH, and the nonstructural protein 1b (ref. 17).

A safe and effective RSV vaccine is not available and is urgently needed. Approaches to the development of RS virus vaccines have included inactivation of the virus with formalin (Kim, H. W., Canchola, J. G., Brandt, C. D., Pyles, G., Chanock, R. M. Jensen, K., and Parrott, R. H. (1969) Amer. J. Epidemiology 89, 422-434), isolation of cold-adapted and/or temperature-sensitive mutant viruses (Firedewald, W. T., Forsyth, B. R., Smith, C. B., Gharpure, M. S., and Chanock, R. M. (1968) JAMA 204, 690-694) and purified F or G glycoproteins (Walsh, E. E., Brandriss, M. W., Schlesinger, J. J. (1985) J. Gen. Virol. 66, 409-415; Walsh, E. E., Schlesinger, J. J. and Brandriss, M. W. (1984) J. Gen. Virol. 65, 761-766; Routledge, E. G., Willcocks, M. M., Samson, A. C. R., Morgan, L., Scott, R., Anderson, J. J., and Toms, G. L). Clinical trial results have shown that both live attenuated and formalin-inactivated vaccines failed to adequately protect vaccines against RS virus infection (Fulginiti, V. A., Eller, J. J., Sieber, O. F., Joyner, I. W., Minamitani, M. and Meiklejohn, G. (1969) Am J. Epidemiol. 89 (4), 435-448; Chin, J., Magoffin, R. L., Shearer, L. A., Schieble, J. H. and Lennette, E. H. (1969) Am. J. Epidemiol. 89 (4), 449-463; Kapikian, A. Z., Mitchell, R. H., Chanock, R. M., Shvedoff, R. A. and Stewart, C. E. (1969) Am. J. Epidemiol. 89 (4), 405-421). Problems encountered with attenuated cold-adapted and/or temperature-sensitive RS virus mutants administered intranasally included clinical morbidity, genetic instability and overattenuation (Kim, H. W., Arrobio, J. O., Pyles, G., Brandt, C. D. Camargo, E., Chanock, R. M. and Parrott, R. H. (1971) Pediatrics 48, 745-755; Wright, P. F., Belshe, R. B., Kim, H. W., Van Voris, L. P. and Chanock, r. M. (1982) Infect. Immun. 37 (1), 397-400; Wright, P. F., Chinozaki, T. and Fleet, W. (1976) J. Pediatr. 88, 931-936). A live RS virus vaccine administered subcutaneously also was not efficacious (Belshe, R. B., Van Voris, P. and Mufson, M. A. (1982) J. Infect. Dis. 145, 311-319). Inactivated RS viral vaccines have typically been prepared using formaldehyde as the inactivating agent. Murphy et al. (Murphy, B. R., Prince, G. A., Walsh, E. E., Kim, H. W., Parrott, R. H., Hemming V. G., Rodriguez, W. J., and Chanock, R. M. J. Clin. Microbiol. (1986), 24(2), 197-202) have reported data on the immune response in infants and children immunized with formalin-inactivated RS virus. Infants (2 to 6 months of age) developed a high titre of antibodies to the F glycoprotein but had a poor response to the G protein. Older individuals (7 to 40 months of age) developed titres of F and G antibodies comparable to those in children who were infected with RS virus. However, both infants and children developed a lower level of neutralizing antibodies than did individuals of comparable age with natural RS virus infections. The unbalanced immune response, with high titres of antibodies to the main immunogenic RS virus proteins F (fusion) and G (attachment) proteins but a low neutralizing antibody titre, may be in part due to alterations of important epitopes in the F and G glycoproteins by the formalin treatment. Furthermore, some infants who received the formalin-inactivated RS virus vaccine developed a more serious lower respiratory tract disease following subsequent exposure to natural RS virus than did non-immunized individuals (Chin, J., Magoffin, R. L., Shearer, L. A., Schieble, J. H. and Lennette, E. H. (1969) Am. J. Epidemiol. 89 (4), 449-463; Kapikian, A. Z., Mitchell, R. H., Chanock, R. M., Shvedoff, R. A. and Stewart, C. E. (1969) Am. J. Epidemiol. 89 (4), 405-421). The formalin-inactivated RS virus vaccines, therefore, have been deemed unacceptable for human use.

Systems for producing recombinant and chimeric viruses suitable for producing attenuated virus suitable for vaccine production has been described by Collins et al. in U.S. Pat. Nos. 6,264,957 and 6,790,449, as well as in WO9802530 to Murphy et al., as well as in Jin et al. in WO 02/44334. Further, Jin et al. describe in US Patent Application Publication 20050176130 additional species of attenuated and/or temperature sensitive RSV for the production of live attenuated vaccines. All references are incorporated herein in their entireties.

As described above, there is currently no effective antiviral therapy to treat RSV. While traditional vaccine development has been based on induction of antibody responses, an alternative approach is the design of vaccines based on eliciting both humoral and cellular immune responses. One such example includes design of vaccines based on CD8+ T cell mediated efficacy, such as with current candidate HIV vaccines. As such, defining the phenotypes and functional properties of vaccine-induced CD8+ T-cells that are associated with efficient target cell killing and minimal immunopathology will greatly improve vaccine design.

A vector-based gene delivery for RSV is described herein that provides benefits over the methods previously described. Vector-based gene delivery can be performed with replication-competent or replication-defective vectors. Replication-competent vectors have potential to induce mucosal immunity and immunize with a single dose; however they may also be associated with more side effects than replication-defective vectors. Among replication-defective vectors, codon modification is less important for those with cytoplasmic transcription programs such as poxvirus or alphavirus vectors. For those vectors such as DNA or adenovirus that utilize nuclear transcription programs, codon-modification for RSV genes will be essential. Replication-defective vectors such as adenoviral vectors or alphavirus vectors or others that can be used in immunization protocols with a single parenteral dose are preferred because of the early age at which immunity is required for protection against severe RSV disease. Heterologous vector combinations that have immunological advantages as described are also preferred, particularly those in which the priming immunization alone can provide partial immunity.

A rationale exists for the design of gene-based replication-defective vaccine vectors, including the following: the control of antigenic content, avoidance of immune suppression, avoidance of rare adverse events associated with live virus in neonatal airways, avoidance of maternal immunity, and control of immune response patterns. In particular embodiments, adenoviral vectors are potentially useful in the methods of the invention. Adenoviral vectors are potentially useful for the following reasons: a single parenteral dose of rAd5 vectors can induce antibody and CD8+ T cell responses in the majority of subjects and is Th1-biased, rAd5 directly induces innate immune responses including maturation of primary dendritic cells, replication-defective adenovirus production is robust, infants between 6 months and 2 years of age have very low prevalence of Ad5 seropositivity, multiple adenovirus serotypes and chimeras are available. In certain cases, heterologous vector boosting induces greater humoral and cell-mediated immunity than homologous boosting. For example, vector priming with rAd35 and boosting with rAd5 may provide partial protection during the neonatal period and complete protection in the infant.

Codon Modification

The DNA code has 4 letters (A, T, C and G) and uses these to spell three letter "codons" which represent the amino acids the proteins encode in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. The use of synonymous codons at unequal frequencies, the codon usage bias, is characteristic of all biological systems. The strength and direction of codon usage bias are related to the genomic G+C content and the relative abundance of different isoaccepting tRNAs. Codon usage can affect the efficiency of gene expression.

Codon usage bias in human RNA viruses generally appears to be low, and differences in codon usage are most strongly correlated with the genomic G+C content, which ranges from 35% in rotavirus to 70% in rubella virus. Codon usage in vertebrate genomic DNAs and most eukaryotic RNA viruses is also shaped by the suppression of CG dinucleotides.

Where more than one codon is available to code for a given amino acid, it has been observed that the codon usage patterns of organisms are highly non-random. Different species show a different bias in their codon selection and, furthermore, utilization of codons may be markedly different in a single species between genes which are expressed at high and low levels. This bias is different in viruses, plants, bacteria and mammalian cells, and some species show a stronger bias away from a random codon selection than others. For example, humans and other mammals are less strongly biased than certain bacteria or viruses. For these reasons, there is a significant probability that a mammalian gene expressed in *E. coli* or a viral gene expressed in mammalian cells will have an inappropriate distribution of codons for efficient expression. It is believed that the presence in a heterologous DNA sequence of clusters of codons which are rarely observed in the host in which expression is to occur, is predictive of low heterologous expression levels in that host.

In consequence, codons preferred by a particular prokaryotic (for example *E. coli* or yeast) or eukaryotic host can be modified so as to encode the same protein, but to differ from a wild type sequence. The process of codon modification may include any sequence, generated either manually or by computer software, where some or all of the codons of the native sequence are modified. Several methods have been published (Nakamura et. al., Nucleic Acids Research 1996, 24:214-215; WO98/34640). One example is the Syngene method, a modification of the Calcgene method (R. S. Hale and G Thompson (Protein Expression and Purification Vol. 12 pp. 185-188 (1998)).

This process of codon modification may have some or all of the following benefits: 1) to improve expression of the gene product by replacing rare or infrequently used codons with more frequently used codons, 2) to remove or include restriction enzyme sites to facilitate downstream cloning and 3) to reduce the potential for homologous recombination between the insert sequence in the DNA vector and genomic sequences and 4) to improve the immune response in humans. The sequences of the present invention advantageously have reduced recombination potential, but express to at least the same level as the wild type sequences. Due to the nature of the algorithms used by the SynGene program to generate a codon modified sequence, it is possible to generate an extremely large number of different codon modified sequences which will perform a similar function. In brief, the codons are assigned using a statistical method to give synthetic gene having a codon frequency closer to that found naturally in highly expressed human genes such as beta-Actin.

In particular preferred embodiments of the invention, in order to generate the codon modified viral genes or fragments, a proprietary, patent-pending development called GENE OPTIMIZER from GeneArt Inc. (on the world wide web at geneart.com) is employed. GENE OPTIMIZER software implements multi-parameter optimization in one single operation, and taking into account the most important parameters in parallel, the software generates a total of up to 500,000 optimized variants of the desired target sequence in an evolutionary approach, and then selects the one that best suits the needed requirements. WO2004059556A3 describes methods and devices for optimizing a nucleotide sequence for the purpose of expression of a protein, incorporated by reference in its entirety herein. WO2006015789A3 describes methods for modulating gene expression by modifying the CpG content, and is incorporated by reference in its entirety herein. Gene Optimizer has advantages of use in database cloning, removal of introns, knockout of cryptic splice sites and RNA destabilizing sequence elements, increased RNA stability, adaptation of codon usage, providing extensive mutagenesis, flexible combination of functional domains, introduction of restriction sites, epitope shuffling and consideration of immune modulatory CpG motifs. In addition, the F sequence was evaluated and modified manually based on consensus amino acid sequence derived from multiple sequences present in the GenBank database, and additional nucleotide sequence modifications were made based on published algorithms to reduce the possibility of splicing events altering the protein sequence.

According to certain embodiments of the invention, it is possible to make further alterations to the F sequence. The original F sequence was based on a single isolate. Certain embodiments feature a new F protein sequence that is based on a comparison of many RSV F sequences and represents a consensus. In certain preferred embodiments, the new F protein sequence has better expression (e.g. shows better protein expression levels) than the original F protein sequence. The modified F sequence is a new nucleotide sequence to encode the F consensus protein and is designed to reduce the chance of internal splicing events that would lead to a truncated protein or altered reading frame. Thus, any alteration that will get rid of cryptic splice sites present within the F sequence (e.g. SEQ ID NO: 13) is possible.

Other tools for generating codon modified viral genes or fragments are described in the art and available for use within the scope and methods of the invention. UpGene is a web-based DNA codon optimization algorithm that is amenable to optimization of any gene of interest. The UpGene tool can be found on the world wide web at vectorcore.pitt.edu/upgene-.html.

DyNAVacS is a web-based tool created for rapid and easy design of DNA vaccines. It follows a step-wise design flow, which guides the user through the various sequential steps in the design of the vaccine. Further, it allows restriction enzyme mapping, design of primers spanning user specified sequences and provides information regarding the vectors currently used for generation of DNA vaccines. The web version uses Apache HTTP server. The interface was written in HTML and utilizes the Common Gateway Interface scripts written in PERL for functionality. DyNAVacS is an integrated tool consisting of user-friendly programs, which require minimal information from the user. The software is available free of cost, as a web based application found on the world wide web at miracle.igib.res.in/dynavac/.

One aspect of the present invention provides an immunogenic composition comprising one or more codon modified viral genes or fragments thereof. In a particular embodiment of the invention, the codon-modified genes or fragments thereof encode viral surface proteins. The codon-modified genes or fragments thereof can encode viral glycoproteins or fragments thereof. The viral glycoproteins or fragments thereof can, but are not limited to encoding, one or more of the fusion (F), membrane anchored attachment (Gr), matrix (M) or (M2), small hydrophobic (SH), nucleoprotein (N), surface (SH) glycoproteins, or fragments thereof.

In one embodiment, the nucleotide sequence of the codon-modified membrane anchored attachment (G) glycoprotein comprises SEQ ID NO: 2, shown below:

SEQ ID NO: 2
ATGAGCAAGAACAAGGACCAGCGGACCGCCAAGACCCTGGAGAGAACCTG

GGACACCCTGAACCACCTGCTGTTCATCAGCAGCTGCCTGTACAAGCTGA

ACCTGAAGAGCGTGGCCCAGATCACCCTGTCTATCCTGGCCATGATCATC

AGCACCAGCCTGATCATCGCCGCCATCATCTTCATCGCCAGCGCCAACCA

CAAAGTGACCCCCACCACAGCCATCATCCAGGACGCCACCTCCCAGATCA

AGAACACCACCCCCACCTACCTGACCCAGAACCCTCAGCTGGGCATCAGC

CCTAGCAACCCCAGCGAGATCACCTCTCAGATCACCACCATCCTGGCCTC

TACCACCCCTGGCGTGAAGTCTACCCTGCAGAGCACCACCGTCAAGACCA

AGAACACGACCACCACACAGACCCAGCCTAGCAAGCCTACCACCAAGCAG

AGGCAGAACAAGCCTCCCAGCAAGCCCAACAACGACTTCCACTTTGAAGT

GTTCAACTTCGTGCCCTGCAGCATCTGCAGCAACAACCCTACCTGCTGGG

CCATCTGCAAGCGCATCCCCAACAAGAAGCCCGGCAAGAAAACCACCACC

AAGCCCACCAAGAAGCCTACCCTCAAGACCACCAAGAAGGACCCCAAGCC

CCAGACCACAAAGAGCAAGGAAGTGCCCACAACCAAGCCTACCGAGGAGC

CCACCATCAACACGACCAAGACCAACATCATCACCACCCTGCTGACCTCT

AACACCACCGGCAACCCTGAGCTGACCAGCCAGATGGAGACCTTCCACAG

CACCTCTAGCGAGGGCAACCCTAGCCCTAGCCAAGTGAGCACCACCTCTG

AGTACCCTAGCCAGCCCAGCTCTCCTCCTAATACCCCTCGGCAGTG

The amino acid sequence of the unmodified membrane anchored attachment (G) glycoprotein is shown in SEQ ID NO: 1, below:

SEQ ID NO: 1
MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVPCSICSNNPTCWAICKRIPNKKPGKKTTT

KPTKKPTLKTTKKDPKPQTTKSKEVPTTKPTEEPTINTTKTNIITTLLTS

NTTGNPELTSQMETFHSTSSEGNPSPSQVSTTSEYPSQPSSPPNTPRQ

In another embodiment, the nucleotide sequence of the codon-modified matrix (M) gene comprises SEQ ID NO: 4, shown below:

SEQ ID NO: 4
ATGGAGACCTACGTGAATAAGCTGCACGAGGGAAGC

ACCTACACCGCCGCTGTGCAGTACAATGTGCTGGAGAAGGA

CGATGATCCTGCTTCCCTGACCATCTGGGTGCCCATGTTTCA

GTCTAGCATGCCCGCCGATCTGCTGATTAAGGAGCTGGCCA

ACGTGAACATCCTGGTGAAGCAGATCAGCACCCCAAAGGGA

CCTTCCCTGAGAGTGATGATTAACTCCAGAAGCGCCGTGCTG

GCCCAGATGCCCTCTAAGTTCACAATCTGCGCTAATGTGTCC

CTGGACGAGAGATCCAAGCTGGCTTACGATGTGACCACCCC

ATGCGAGATCAAGGCTTGTTCTCTGACCTGTCTGAAGTCCAA

GAATATGCTGACCACCGTGAAGGACCTGACAATGAAAACAC

TGAATCCCACCCACGATATCATCGCCCTGTGTGAGTTTGAGA

ATATCGTGACAAGCAAGAAGGTCATCATCCCAACATACCTG

AGATCTATCTCTGTGAGGAATAAGGATCTGAACACACTGGA

GAATATCACAACCACCGAGTTTAAGAACGCTATCACAAACG

CCAAGATCATCCCTTACAGCGGACTGCTGCTGGTCATCACAG

TGACCGATAACAAGGGCGCCTTCAAGTACATCAAGCCACAG

TCCCAGTTCATCGTGGATCTGGGCGCTTACCTGGAGAAGGA

GAGCATCTACTACGTGACCACCAACTGGAAGCACACAGCTA

CAAGATTCGCCATCAAGCCCATGGAGGAC

The amino acid sequence of the unmodified matrix (M) gene is shown in SEQ ID NO: 3, below:

SEQ ID NO: 3
METYVNKLHEGSTYTAAVQYNVLEKDDDPASLTIWVPMFQSSMPAD

LLIKELANVNILVKQISTPKGPSLRVMINSRSAVLAQMPSKFTICA

NVSLDERSKLAYDVTTPCEIKACSLTCLKSKNMLTTVKDLTMKTLN

PTHDIIALCEFENIVTSKKVIIPTYLRSISVRNKDLNTLENITTTE

FKNAITNAKIIPYSGLLLVITVTDNKGAFKYIKPQSQFIVDLGAYL

EKESIYYVTTNWKHTATRFAIKPMED

In another embodiment, the nucleotide sequence of the codon-modified matrix (M2) gene comprises SEQ ID NO: 6, shown below:

SEQ ID NO: 6
ATGAGCCGGCGGAATCCATGTAAGTTCGAGATCAGAG

GCCACTGCCTGAATGGAAAGAGATGCCACTTCAGCCACAAC

TACTTCGAGTGGCCCCCACACGCTCTGCTGGTGAGACAGAAT

TTCATGCTGAACCGCATCCTGAAGAGCATGGATAAGAGCAT

CGACACACTGAGCGAGATCTCTGGCGCTGCCGAGCTGGATC

GGACAGAGGAGTACGCCCTGGGAGTGGTGGGAGTGCTGGAG

AGCTACATCGGCTCCATCAATAACATCACCAAGCAGAGCGC

CTGCGTGGCTATGAGCAAGCTGCTGACCGAGCTGAATAGCG

ATGACATCAAGAAGCTGAGAGACAACGAGGAGCTGAACAG

CCCAAAGATCAGAGTGTACAATACAGTGATCTCTTACATCG

AGAGCAATAGGAAGAACAACAAGCAGACCATCCACCTGCTG

AAGAGACTGCCCGCTGATGTGCTGAAGAAAACCATCAAGAA

TACACTGGACATCCACAAGTCTATCACAATCAACAATCCTAA

GGAGAGCACAGTGAGCGATACAAACGACCACGCTAAGAAT

AATGATAC

The amino acid sequence of the unmodified matrix (M2) gene is shown in SEQ ID NO: 5, below:

SEQ ID NO: 5
MSRRNPCKFEIRGHCLNGKRCHFSHNYFEWPPHALLVRQNFML

NRILKSMDKSIDTLSEISGAAELDRTEEYALGVVGVLESYIGSIN

NITKQSACVAMSKLLTELNSDDIKKLRDNEELNSPKIRVYNTVI

SYIESNRKNNKQTIHLLKRLPADVLKKTIKNTLDIHKSITINNPK

ESTVSDTNDHAKNNDTT

In another embodiment, the nucleotide sequence of the codon-modified matrix fusion (M/M2) gene comprises SEQ ID NO: 8, shown below:

SEQ ID NO: 8
ATGGAGACCTACGTGAATAAGCTGCACGAGGGAAGC

ACCTACACCGCCGCTGTGCAGTACAATGTGCTGGAGAAGGA

CGATGATCCTGCTTCCCTGACCATCTGGGTGCCCATGTTTCA

GTCTAGCATGCCCGCCGATCTGCTGATTAAGGAGCTGGCCA

ACGTGAACATCCTGGTGAAGCAGATCAGCACCCCAAAGGGA

CCTTCCCTGAGAGTGATGATTAACTCCAGAAGCGCCGTGCTG

GCCCAGATGCCCTCTAAGTTCACAATCTGCGCTAATGTGTCC

CTGGACGAGAGATCCAAGCTGGCTTACGATGTGACCACCCC

ATGCGAGATCAAGGCTTGTTCTCTGACCTGTCTGAAGTCCAA

GAATATGCTGACCACCGTGAAGGACCTGACAATGAAAACAC

TGAATCCCACCCACGATATCATCGCCCTGTGTGAGTTTGAGA

ATATCGTGACAAGCAAGAAGGTCATCATCCCAACATACCTG

AGATCTATCTCTGTGAGGAATAAGGATCTGAACACACTGGA

GAATATCACAACCACCGAGTTTAAGAACGCTATCACAAACG

CCAAGATCATCCCTTACAGCGGACTGCTGCTGGTCATCACAG

TGACCGATAACAAGGGCGCCTTCAAGTACATCAAGCCACAG

TCCCAGTTCATCGTGGATCTGGGCGCTTACCTGGAGAAGGA

GAGCATCTACTACGTGACCACCAACTGGAAGCACACAGCTA

CAAGATTCGCCATCAAGCCCATGGAGGACCCTGATCAGGCT

ATGTCTAGGCGCAACCCTTGCAAGTTTGAGATCCGGGGACA

CTGTCTGAACGGCAAGCGGTGTCACTTTTCTCACAATTACTT

TGAGTGGCCTCCTCACGCCCTGCTGGTGCGGCAGAACTTTAT

GCTGAATAGAATCCTGAAGTCTATGGACAAGTCTATCGATA

CCCTGTCCGAGATCTCCGGAGCCGCTGAGCTGGACAGAACC

GAGGAGTACGCTCTGGGCGTGGTGGGCGTGCTGGAGTCTTA

CATCGGCAGCATCAACAATATCACAAAGCAGTCCGCTTGTG

TGGCCATGTCTAAGCTGCTGACAGAGCTGAACTCTGACGAT

ATCAAGAAGCTGCGGGATAACGAGGAGCTGAATTCCCCTAA

GATCCGCGTGTACAACACCGTGATCTCCTACATCGAGTCCAA

CCGCAAGAATAATAAGCAGACAATCCACCTGCTGAAGCGGC

TGCCTGCCGACGTGCTGAAGAAAACAATCAAGAACACCCTG

GATATCCACAAGAGCATCACCATCAATAACCCCAAGGAGTC

TACCGTGTCCGACACAAACGATCACGCCAAGAACAACGACA

CAA

In another embodiment, the nucleotide sequence of the codon-modified nucleoprotein (N) gene comprises SEQ ID NO: 10, shown below:

SEQ ID NO: 10
ATGGCCCTGAGCAAGGTCAAGCTGAACGACACCCTGA

ACAAGGACCAGCTGCTGTCCAGCAGCAAGTACACCATCCAG

AGAAGCACCGGCGACAGCATCGACACCCCCAACTACGACGT

GCAGAAGCACATCAACAAGCTGTGCGGCATGCTGCTGATCA

CCGAGGACGCCAACCACAAGTTCACCGGCCTGATCGGCATG

CTGTACGCCATGAGCAGGCTGGGCAGAGAGGACACCATCAA

GATCCTGAGGGACGCCGGCTACCACGTGAAGGCCAACGGCG

TGGACGTGACCACCCACAGGCAGGACATCAACGGCAAGGAG

AACAAGTTCGAGGTCCTGACCCTGGCCAGCCTGACCACCGA

GATCCAGATCAACATCGAGATCGAGTCTAGGAAGAGCTACA

AGAAGATGCTGAAGGAGATGGGCGAGGTCGCCCCCGAGTAC

AGGCACGACAGCCCCGACTGCGGCATGATCATCCTGTGCAT

CGCCGCCCTGGTCATCACCAAGCTGGCTGCCGGCGACAGAA

GCGGCCTGACCGCCGTCATCAGACGGGCCAACAACGTGCTG

AAGAACGAGATGAAGAGGTACAAGGGCCTGCTGCCCAAGG

ACATCGCCAACAGCTTCTACGAGGTGTTCGAGAAGCACCCC

CACTTCATCGACGTGTTCGTGCACTTCGGCATCGCCCAGAGC

AGCACCAGGGGCGGCAGCAGGGTGGAGGGCATCTTCGCCGG

CCTGTTCATGAACGCCTACGGAGCCGGCCAGGTCATGCTGA

GATGGGGCGTGCTGGCCAAGAGCGTGAAGAACATCATGCTG

GGCCACGCCAGCGTGCAGGCCGAGATGGAACAGGTGGTGGA

GGTGTACGAGTACGCCCAGAAGCTGGGCGGCGAGGCCGGCA

GATACCACATCCTGAACAACCCCAAGGCCTCCCTGCTGTCCC

TGACCCAGTTCCCCCACTTCTCCAGCGTGGTGCTGGGCAATG

CCGCCGGACTGGGCATCATGGGCGAGTACAGAGGCACCCCC

AGGAACCAGGACCTGTACGACGCCGCCAAGGCCTACGCCGA

GCAGCTGAAGGAGAACGGCGTCATCAACTACAGCGTGCTGG

ATCTGACCGCCGAGGAACTGGAAGCCATCAAGCACCAGCTG

AACCCCAAGGACAACGACGTGGAGCTGTGATGAGGATCCGA

GCTC

The amino acid sequence of the unmodified nucleoprotein (N) gene is shown in SEQ ID NO: 9, below:

SEQ ID NO: 9
MALSKVKLNDTLNKDQLLSSSKYTIQRSTGDSIDTPNYDVQKHI

NKLCGMLLITEDANHKFTGLIGMLYAMSRLGREDTIKILRDAG

YHVKANGVDVTTHRQDINGKEMKFEVLTLASLTTEIQINIEIES

RKSYKKMLKEMGEVAPEYRHDSPDCGMIILCIAALVITKLAAG

DRSGLTAVIRRANNVLKNEMKRYKGLLPKDIANSFYEVFEKHP

HFIDVFVHFGIAQSSTRGGSRVEGIFAGLFMNAYGAGQVMLRW

GVLAKSVKNIMLGHASVQAEMEQVVEVYEYAQKLGGEAGFY

HILNNPKASLLSLTQFPHFSSVVLGNAAGLGIMGEYRGTPRNQD

LYDAAKAYAEQLKENGVINYSVLDLTAEELEAIKHQLNPKDND

VEL

In another embodiment, the nucleotide sequence of the codon-modified SH envelope glycoprotein comprises SEQ ID NO: 12, shown below:

SEQ ID NO: 12
ATGGAAAACACCAGCATCACCATCGAGTTCAGCAGCA

AGTTCTGGCCCTACTTCACCCTGATCCACATGATCACCACCA

TCATCAGCCTGCTGATCATCATCAGCATCATGATCGCCATCC

TGAACAAGCTGTGCGAGTACAACGTGTTCCACAACAAGACC

TTCGAGCTGCCCAGGGCCAGGGTGAACACCT

The amino acid sequence of the unmodified SH envelope glycoprotein is shown in SEQ ID NO: 11, below:

SEQ ID NO: 11
MENTSITIEFSSKFWPYFTLIHMITTIISLLIIISIMIAILNK

LCEYNVFHNKTFELPRARVNT

In another embodiment, the nucleotide sequence of the codon-modified fusion (F) glycoprotein comprises SEQ ID NO: 14, shown below:

SEQ ID NO: 14
ATGGAGCTGCTGATCCTGAAGGCCAACGCCATCACCA

CCATCCTGACCGCCGTGACCTTCTGCTTCGCCAGCGGCCAGA

ATATCACCGAGGAGTTCTACCAGAGCACCTGTAGCGCCGTG

TCCAAGGGCTACCTGAGCGCCCTGAGAACCGGCTGGTACAC

-continued

```
CAGCGTGATCACCATCGAGCTGTCCAACATCAAGGAAAACA

AGTGTAACGGCACCGACGCCAAGGTGAAGCTGATCAAGCAG

GAGCTGGACAAGTACAAGAACGCCGTGACCGAGCTGCAGCT

GCTGATGCAGAGCACCCCCCCCACCAACAACAGAGCCAGGC

GCGAGCTGCCCCGGTTCATGAACTACACCCTGAACAACGCC

AAGAAAACCAACGTGACCCTGAGCAAGAAGCGGAAGCGGA

GATTCCTGGGCTTCCTGCTGGGAGTGGGCAGCGCCATCGCCA

GCGGAGTGGCCGTGTCTAAGGTGCTGCACCTGGAGGGCGAG

GTGAACAAGATCAAGAGCGCCCTGCTGTCCACCAACAAGGC

CGTGGTGTCCCTGAGCAACGGCGTGTCCGTGCTGACCAGCA

AGGTGCTGGATCTGAAGAACTACATCGACAAGCAGCTGCTG

CCCATCGTGAACAAGCAGAGCTGCTCCATCAGCAACATCGA

GACCGTGATCGAGTTCCAGCAGAAGAACAACCGGCTGCTGG

AGATCACCAGGGAGTTCAGCGTGAACGCCGGCGTGACCACC

CCTGTGAGCACCTACATGCTGACCAACAGCGAGCTGCTGTCC

CTGATCAATGACATGCCCATCACCAACGACCAGAAAAAGCT

GATGAGCAACAACGTGCAGATTGTGAGGCAGCAGAGCTACA

GCATCATGAGCATCATCAAGGAAGAGGTGCTGGCCTACGTG

GTGCAGCTGCCCCGTGACGGCGTGATCGATACCCCTTGCTGG

AAGCTGCACACCAGCCCTCTGTGTACCACCAACACCAAGGA

GGGCAGCAACATCTGCCTGACCAGGACCGATAGAGGCTGGT

ACTGTGACAATGCCGGCAGCGTGTCCTTCTTCCCCCAGGCCG

AGACCTGTAAGGTGCAGAGCAACCGGGTGTTCTGTGACACC

ATGAACAGCCTGACCCTGCCCAGCGAGATCAACCTGTGTAA

CGTGGACATCTTCAACCCCAAGTACGACTGTAAGATCATGA

CCTCCAAGACCGACGTGTCCAGCAGCGTGATTACCAGCCTG

GGCGCCATCGTGTCCTGCTACGGCAAGACCAAGTGTACCGC

CAGCAACAAGAACCGGGGGATCATCAAGACCTTCAGCAACG

GCTGTGACTACGTGTCAACAAGGGCATGGACACCGTGTCTG

TGGGCAACACACTGTACTACGTGAATAAGCAGGAGGGCAAG

AGCCTGTACGTGAAGGGCGAGCCCATCATCAACTTCTACGA

CCCCCTGGTGTTCCCTAGCGACGAGTTCGATGCCAGCATCAG

CCAGGTGAACGAGAAGATCAACCAGAGCCTGGCCTTCATCA

GGAAGAGCGACGAGCTGCTGCACAATGTGAATGCCGGCAAG

AGCACCACCAACATCATGATCACCACAATCATCATCGTGATC

ATTGTGATCCTGCTGTCTCTGATTGCTGTGGGCCTGCTGCTGT

ACTGTAAGGCCAGATCCACCCCCGTGACCCTGTCCAAGGAC

CAGCTGTCCGGCATCAACAACATCGCCTTCTCCAACTGATGA

GGATCCAG
```

The amino acid sequence of the unmodified fusion (F) glycoprotein is shown in SEQ ID NO: 13, below:

SEQ ID NO: 13

MELLILKANAITTILTAVTFCFASGQNITEEFYQSTCSAVSKGYL

SALRTGWYTSVITIELSNIKENKCNGTDAKVKLIKQELDKYKNA

VTELQLLMQSTPPTNNRARRELPRFMNYTLNNAKKTNVTLSKK

RKRRFLGFLLGVGSAIASGVAVSKVLHLEGEVNKIKSALLSTNK

AVVSLSNGVSVLTSKVLDLKNYIDKQLLPIVNKQSCSISNIETVI

EFQQKNNRLLEITREFSVNAGVTTPVSTYMLTNSELLSLINDMPI

TNDQKKLMSNNVQIVRQQSYSIMSIIKEEVLAYVVQLPLYGVID

TPCWKLHTSPLCTTNTKEGSNICLTRTDRGWYCDNAGSVSFFP

QAETCKVQSNRVFCDTMNSLTLPSEINLCNVDIFNPKYDCKIMT

SKTDVSSSVITSLGAIVSCYGKTKCTASNKNRGIIKTFSNGCDYV

SNKGMDTVSVGNTLYYVNKQEGKSLYVKGEPIINFYDPLVFPS

DEFDASISQVNEKINQSLAFIRKSDELLHNVNAGKSTTNIMITTII

IVIIVILLSLIAVGLLLYCKARSTPVTLSKDQLSGINNIAFSN

In another embodiment, the nucleotide sequence of the codon-modified fusion (F) glycoprotein comprises SEQ ID NO: 17, shown below:

GGTACCGTCGACGCCACCATGGAGCTGCTGATCCTGAAGGC

CAACGCCATCACCACCATCCTGACCGCCGTGACCTTCTGCTT

CGCCAGCGGCCAGAATATCACCGAGGAGTTCTACCAGAGCA

CCTGTAGCGCCGTGTCCAAGGGCTACCTGAGCGCCCTGAGA

ACCGGCTGGTACACCAGCGTGATCACCATCGAGCTGTCCAA

CATCAAGGAAAACAAGTGTAACGGCACCGACGCCAAGGTGA

AGCTGATCAAGCAGGAGCTGGACAAGTACAAGAACGCCGTG

ACCGAGCTGCAGCTGCTGATGCAGAGCACCCCCGCCACCAA

CAACAGAGCCAGGCGCGAGCTGCCCCGGTTCATGAACTACA

CCCTGAACAACGCCAAGAAAACCAACGTGACCCTGAGCAAG

AAGCGGAAGCGGAGATTCCTGGGCTTCCTGCTGGGAGTGGG

CAGCGCCATCGCCAGCGGAGTGGCCGTGTCTAAGGTGCTGC

ACCTGGAGGGCGAGGTGAACAAGATCAAGAGCGCCCTGCTG

TCCACCAACAAGGCCGTGGTGTCCCTGAGCAACGGCGTGTC

CGTGCTGACCAGCAAGGTGCTGGATCTGAAGAACTACATCG

ACAAGCAGCTGCTGCCCATCGTGAACAAGCAGAGCTGCTCC

ATCAGCAACATCGAGACCGTGATCGAGTTCCAGCAGAAGAA

CAACCGGCTGCTGGAGATCACCAGGGAGTTCAGCGTGAACG

CCGGCGTGACCACCCCTGTGAGCACCTACATGCTGACCAAC

AGCGAGCTGCTGTCCCTGATCAATGACATGCCCATCACCAAC

GACCAGAAAAAGCTGATGAGCAACAACGTGCAGATTGTGAG

GCAGCAGAGCTACAGCATCATGAGCATCATCAAGGAAGAGG

```
-continued
TGCTGGCCTACGTGGTGCAGCTGCCCCTGTACGGCGTGATCG

ATACCCCTTGCTGGAAGCTGCACACCAGCCCTCTGTGTACCA

CCAACACCAAGGAGGGCAGCAACATCTGCCTGACCAGGACC

GATAGAGGCTGGTACTGTGACAATGCCGGCAGCGTGTCCTT

CTTCCCCCAGGCCGAGACCTGTAAGGTGCAGAGCAACCGGG

TGTTCTGTGACACCATGAACAGCCTGACCCTGCCCAGCGAG

GTGAACCTGTGTAACGTGGACATCTTCAACCCCAAGTACGA

CTGTAAGATCATGACCTCCAAGACCGACGTGTCCAGCAGCG

TGATTACCAGCCTGGGCGCCATCGTGTCCTGCTACGGCAAGA

CCAAGTGTACCGCCAGCAACAAGAACCGGGGGATCATCAAG

ACCTTCAGCAACGGCTGTGACTACGTGTCCAACAAGGGCGT

GGACACCGTGTCTGTGGGCAACACACTGTACTACGTGAATA

AGCAGGAGGGCAAGAGCCTGTACGTGAAGGGCGAGCCCATC

ATCAACTTCTACGACCCCCTGGTGTTCCCTAGCGACGAGTTC

GATGCCAGCATCAGCCAGGTGAACGAGAAGATCAACCAGAG

CCTGGCCTTCATCAGGAAGAGCGACGAGCTGCTGCACAATG

TGAATGCCGGCAAGAGCACCACCAACATCATGATCACCACA

ATCATCATCGTGATCATTGTGATCCTGCTGTCTCTGATTGCTG

TGGGCCTGCTGCTGTACTGTAAGGCCAGATCCACCCCCGTGA

CCCTGTCCAAGGACCAGCTGTCCGGCATCAACAACATCGCCT

TCTCCAACTGATGAGGATCCGAGCTC
```

The amino acid sequence corresponding to the nucleotide sequence of the fusion (F) glycoprotein as shown in SEQ ID NO: 17 above is shown in SEQ ID NO: 16, below:

```
MELLILKANAITTILTAVTFCFASGQNITEEFYQSTCSAVSKGY

LSALRTGWYTSVITIELSNIKENKCNGTDAKVKLIKQELDKYK

NAVTELQLLMQSTPATNNRARRELPRFMNYTLNNAKKTNVT

LSKKRKRRFLGFLLGVGSAIASGVAVSKVLHLEGEVNKIKSA

LLSTNKAVVSLSNGVSVLTSKVLDLKNYIDKQLLPIVNKQSCS

ISNIETVIEFQQKNNRLLEITREFSVNAGVTTPVSTYMLTNSEL

LSLINDMPITNDQKKLMSNNVQIVRQQSYSIMSIIKEEVLAYV

VQLPLYGVIDTPCWKLHTSPLCTTNTKEGSNICLTRTDRGWY

CDNAGSVSFFPQAETCKVQSNRVFCDTMNSLTLPSEVNLCNV

DIFNPKYDCKIMTSKTDVSSSVITSLGAIVSCYGKTKCTASNK

NRGIIKTFSNGCDYVSNKGVDTVSVGNTLYYVNKQEGKSLY

VKGEPIINFYDPLVFPSDEFDASISQVNEKINQSLAFIRKSDELL

HNVNAGKSTTNIMITTIIIVIIVILLSLIAVGLLLYCKARSTPVTL

SKDQLSGINNIAFSN**
```

A modified nucleotide sequence of the codon-modified fusion (F) glycoprotein comprises SEQ ID NO: 18, shown below:

```
GGTACCGTCGACGCCACCATGGAGCTGCTGATCCTGAAGG

CCAACGCCATCACCACCATCCTGACCGCCGTGACCTTCTGC

TTCGCCAGCGGCCAGAATATCACCGAGGAGTTCTACCAGA

GCACCTGTAGCGCCGTGTCCAAGGGCTACCTGAGCGCCCT

GAGAACCGGCTGGTACACCAGCGTGATCACCATCGAGCTG

TCCAACATCAAGGAAAACAAGTGTAACGGCACCGACGCCA

AGGTGAAGCTGATCAAGCAGGAGCTGGACAAGTACAAGA

ACGCCGTGACCGAGCTGCAGCTGCTGATGCAGAGCACCCC

CGCCACCAACAACAGAGCCAGGCGCGAGCTGCCCCGGTTC

ATGAACTACACCCTGAACAACGCCAAGAAAACCAACGTGA

CCCTGAGCAAGAAGCGGAAGCGGAGATTCCTGGGCTTCCT

GCTGGGAGTGGGCAGCGCCATCGCCAGCGGAGTGGCCGTG

TCTAAGGTGCTGCACCTGGAGGGCGAGGTGAACAAGATCA

AGAGCGCCCTGCTGTCCACCAACAAGGCCGTGGTGTCCCT

GAGCAACGGCGTGTCCGTGCTGACCAGCAAGGTGCTGGAT

CTGAAGAACTACATCGACAAGCAGCTGCTGCCCATCGTGA

ACAAGCAGAGCTGCTCCATCAGCAACATCGAGACCGTGAT

CGAGTTCCAGCAGAAGAACAACCGGCTGCTGGAGATCACC

AGGGAGTTCAGCGTGAACGCCGGCGTGACCACCCCTGTGA

GCACCTACATGCTGACCAACAGCGAGCTGCTGTCCCTGAT

CAATGACATGCCCATCACCAACGACCAGAAAAAGCTGATG

AGCAACAACGTGCAGATTGTGAGGCAGCAGAGCTACAGCA

TCATGAGCATCATCAAGGAAGAGGTGCTGGCCTACGTGGT

GCAGCTGCCCCTGTACGGCGTGATCGATACCCCTTGCTGGA

AGCTGCACACCAGCCCTCTGTGTACCACCAACACCAAGGA

GGGCAGCAACATCTGCCTGACCAGGACCGATAGAGGCTGG

TACTGTGACAATGCCGGCAGCGTGTCCTTCTTTCCGCAAGC

CGAGACCTGTAAGGTGCAGAGCAACCGGGTGTTCTGTGAC

ACCATGAACAGCCTGACCCTGCCCAGCGAGGTGAACCTGT

GTAACGTGGACATCTTCAACCCCAAGTACGACTGTAAGAT

CATGACCTCCAAGACCGACGTGTCCAGCAGCGTGATTACC

AGCCTGGGCGCCATCGTGTCCTGCTACGGCAAGACCAAGT

GTACCGCCAGCAACAAGAACCGGGGGATCATCAAGACCTT

CAGCAACGGCTGTGACTACGTGTCCAACAAGGGCGTGGAC

ACCGTGTCTGTGGGCAACACACTGTACTACGTGAATAAGC

AGGAGGGCAAGAGCCTGTACGTGAAGGGCGAGCCCATCAT

CAACTTCTACGACCCCCTGGTGTTCCCTAGCGACGAGTTCG

ATGCCAGCATCAGCCAGGTGAACGAGAAGATCAACCAGA
```

```
GCCTGGCCTTCATCAGGAAGAGCGACGAGCTGCTGCACAA

TGTGAATGCCGGCAAGAGCACCACCAACATCATGATCACC

ACAATCATCATCGTGATCATTGTGATCCTGCTGTCTCTGAT

TGCTGTGGGCCTGCTGCTGTACTGTAAGGCCAGATCCACCC

CCGTGACCCTGTCCAAGGACCAGCTGTCCGGCATCAACAA

CATCGCCTTCTCCAACTGATGAGGATCCGAGCTC
```

The original F sequence was based on a single isolate. Certain embodiments feature a new F protein sequence that is based on a comparison of many RSV F sequences and represents a consensus. In certain preferred embodiments, the new F protein sequence has better expression (e.g. shows better protein expression levels) than the original F protein sequence. The modified F sequence is a new nucleotide sequence to encode the F consensus protein and is designed to reduce the chance of internal splicing events that would lead to a truncated protein or altered reading frame.

The amino acid sequence of the retained membrane attachment glycoprotein (G) is shown in SEQ ID NO: 15, below:

```
MSKNKDQRTAKTLERTWDTLNHLLFISSCLYKLNLKSVAQITL

SILAIIISTSLIIAAIIFIASANHKVTPTTAIIQDATSQIKNTTPTY

LTQNPQLGISPSNPSEITSQITTILASTTPGVKSTLQSTTVKTKNTT

TTQTQPSKPTTKQRQNKPPSKPNNDFHFEVFNEVPCSICSNNPTC

WAICKRIPNKKPGKKTTTKPTKKPTLKTTKKDPKPQTTKSKEVP

TTKPTEEPTINTTKTNIITTLLTSNTTGNPELTSQMETFHSTSSEG

NPSPSQVSTTSEYPSQPSSPPNTPRQ
```

Methods of the Invention

The methods of the invention are particularly useful for inducing an immune response in a subject.

In particular, the invention encompasses a method of eliciting an immune response capable of preventing viral infection in a subject. According to the method, the subject is administered an immunogenic composition comprising a vector comprising one or more viral codon modified genes or fragments wherein the codon modification induces an immune response, and a pharmaceutically acceptable carrier, thereby eliciting an immune response capable of preventing viral infection in a subject. In certain examples of the method the viral infection is a Paramyxoviral infection, and the vector comprises one or more Paramyxovirus codon modified genes or fragments.

The invention further encompasses a method of treating a subject having a viral infection comprising administering to the subject an immunogenic composition comprising: a vector with one or more viral codon modified genes or fragments and where the codon modification induces an immune response, and a pharmaceutically acceptable carrier, and thereby treating viral infection in a subject. In certain examples of the method the viral infection is a Paramyxoviral infection, and the vector comprises one or more Paramyxovirus codon modified genes or fragments.

Other exemplary methods of the invention are particularly useful for eliciting an immune response capable of preventing RSV infection in a subject, the method comprising administering to the subject an immunogenic composition comprising a vector comprising one or more RSV codon modified genes or fragments encoding one or more of any of the polypeptides of the invention as described herein, and where the codon modification induces an immune response, and a pharmaceutically acceptable carrier. The method elicits an immune response capable of preventing RSV infection in a subject.

In a related method, a subject having RSV infection is treated by a method comprising administering to the subject an immunogenic composition comprising: a vector comprising one or more RSV codon modified genes or fragments encoding one or more of any of the polypeptides as described herein, wherein the codon modification induces an immune response, and a pharmaceutically acceptable carrier, and thereby treating a subject having RSV infection.

In a specific example, the method is used for eliciting an immune stimulatory activity of an RSV glycoprotein, the method comprising introducing a codon modification in one or more RSV glycoprotein genes or fragments into one or more vectors for administration to a subject, and thereby eliciting an immune stimulatory activity of an RSV glycoprotein. In another step of the method, an alteration in the immune stimulatory activity of the RSV glycoprotein is detected. The alteration in immune stimulatory activity can be an antibody response, and can thus be detected by measurement of viral neutralization. The alteration in immune stimulatory activity can be a T cell response, and can thus be detected by CD8 T+ cell activity.

The invention described codon modification, and in certain examples, the codon modification enhances protein expression. Thus, methods of the invention are directed to enhancing protein production of a Paramyxovirus glycoprotein, the method comprising: introducing a codon modification in one or more Paramyxovirus glycoprotein genes or fragments into one or more vectors for administration to a subject, and thus enhancing protein production of a Paramyxovirus glycoprotein. Enhancement in protein production can be detected in any number of ways including, but not limited to, Western Blot, fluorimetry or colorimetry. The codon modification that causes the enhancement in protein expression, in certain exemplary embodiments, can occur in, but is not limited to occurring in, the coding region of the gene.

According to the method, the immune response or increase in protein production is generated by administration of the immunogenic composition. The immune response or increase in protein production can be generated by a single administration of the immunogenic composition. It is also possible that the immune response or increase in protein production is generated by more than one administration of the immunogenic composition.

In any of the methods of the invention, the subject to be treated can be a mammal, such as a human patient or an animal (e.g., a rodent, bovine, equine, porcine, ovine, canine, feline, or other domestic mammal). In certain specific examples, the subject is a human. Certain high risk populations are attractive targets for treatment using the methods of the invention. For example, the human subject can be, but is not limited to the groups of pregnant women, neonates, young infants, and organ transplantation patients. In particular, for example, the organ transplantation patient may be a lung transplantation patient prior to transplant or a bone marrow transplantation patient prior to transplant.

Paramyxoviral infection is by a virus selected from the group consisting of: Avulaviral infection, Henipaviral infection, Morbilliviral infection, Respiroviral infection, Rubulaviral infection, Pneumoviral infection, and Metapneumoviral infection. As described, the methods of the invention are particularly useful for inducing an immune response in a subject. The methods of the invention are suited for preventing or treating a viral infection, for example a Paramyxovirus infection. The Paramyxovirus can be selected from, but not limited to, the group consisting of: human, canine, feline, avian, murine, simian, bovine or ovine Paramyxovirus. Further, the Paramyxovirus can be selected from, but not limited to, Avulavirus, Henipavirus, Morbillivirus, Respirovirus, Rubulavirus, Pneumovirus, and Metapneumovirus. In certain preferred example, the Pneumovirus is Respiratory Syncytial Virus (RSV).

Nucleic Acids and Expression Vectors

In the present invention, expression vectors are provided which comprise a nucleic acid molecule encoding one or more codon modified genes, or fragments thereof, and are capable of directing the expression of one or more codon modified genes, or fragments thereof. The plasmids and vectors can be used to express a gene in a host cell.

The vectors can be a plurality of vectors, each comprising one or more of the codon-modified genes, or fragments thereof of the invention as described herein. Thus, there can be 1, 2, 3, 4, or more vectors, each comprising one or more of the codon-modified genes, or fragments thereof of the invention as described herein. In certain examples, two or more vectors each comprise one or more of the codon-modified genes, or fragments thereof, a polynucleotide sequence according to the invention. Any of the vectors as described herein may be suitable for driving expression of heterologous DNA in bacterial, insect, mammalian cells, and particularly human cells.

Various vectors can be employed in the methods of the invention. For example, the vector can be a replication-competent vector. Alternatively, the vector can be a replication-defective vector. Exemplary replication-competent vectors include, but are not limited to vaccinia, vescicular stomatitis virus, measles virus and other Paramyxovirus vectors, BCG, and adenovirus. Exemplary replication deficient vectors include, but are not limited to adenovirus vectors based on multiple serotypes and chimeras, alphavirus vectors such as Semliki Forest virus, Venezuelan equine encephalitis virus, or Sinbis virus, MVA or other attenuated poxvirus vectors, adeno-associated virus (AAV), vescicular stomatitis virus vectors, herpesvirus vectors, or DNA alone. For example, vectors used can be, but are not limited to, bacterial vectors, adenoviral vectors, adeno-associated viral vectors, herpes simplex virus, Venezuelan equine encephalitis, BCG, retroviral vectors, Herpesvirus vectors, alphavirus vectors, flavivirus vectors, vescicular stomatitis virus vectors, mycobacterial vectors, poxvirus vectors, and nucleic acid based vectors. The vector can be an adenoviral vector selected from, but not limited to, rAd5, rAd26, rAd 41, rAd6, rAd35, and adenoviruses from other species such as chimpanzee, and chimeric adenovirus constructs. Adenoviral vectors are very efficient at transducing target cells in vitro and in vivo, and can be produced at high titres. In general, transgene expression in vivo from progenitor vectors tends to be transient. Following intravenous injection, 90% of the administered vector is degraded in the liver by a non-immune mediated mechanism (Worgall et al, 1997). Further, the finding that inverted repeats present with Ad vector genomes can mediate precise genetic recombination has important implications for the development of new vectors for gene therapy approaches, including vectors with large inserts or toxic genes. The production of rep78 expressing Ad vectors represents a major step forward in development of site-specific integrating vectors. These new Ad vectors overcome a number of limitations associated with viral vector systems.

The present invention includes the use of gene-based replication-defective immunomodulatory vectors, including vaccine vectors. The rationale for the use of such vectors in the methods of the invention includes the control of antigenic content, the avoidance of immune suppression or rare adverse events, the avoidance of maternal immunity, the induction of both CD8+ T cell and antibody responses and the control of immune response patterns. Further, the use of this approach may allow for the protection of the lower airway by parenteral immunization that may protect against illness while allowing boosting thorough subclinical upper airway infection.

Semliki Forest virus (SFV) is a member of the Alphavirus genus in the Togaviridae family. The mature virus particle contains a single copy of a ssRNA genome with a positive polarity that is 5'-capped and 3'-polyadenylated. It functions as a naked RNA (nRNA), and naked RNA can start an infection when introduced into cells. Upon infection/transfection, the 5' two-thirds of the genome is translated into a polyprotein that is processed into the four nonstructural proteins (nsP1 to 4) by self-cleavage. Once the ns proteins have been synthesized they are responsible for replicating the plus-strand (42S) genome into full-length minus strands (Fualginiti, V. A., Eller, J. J., Siaber, O. F., Joyner, J. W., Minamitani, M. and Meiklejohn, G. (1969) Am. J. Epidemriol. 89 (4), 435-1448). These minus-stands then serve as templates for the synthesis of new plus-strand (42S) genomes and the 26S subgenomic mRNA. This subgenomic mRNA, which is colinear with the last one-third of the genome, encodes the SFV structural proteins.

In certain preferred embodiments of the invention, rAd5 and SFV provide the most potent gene-delivery vectors in a vaccination schedule.

Vectors of the invention may be chimeric vectors. For example, chimeric adenoviral and retroviral vectors have been described (Feng et al., Nature Biotechnology 15, 866-870 (1997)) that incorporate favorable aspects of both adenoviral and retroviral vectors. Here, adenoviral vectors induce target cells to function as transient retroviral producer cells in vivo, and the progeny retroviral vector particles are then able to stably transduce neighboring cells. In this system, the nonintegrative adenoviral vector is rendered functionally integrative via the intermediate generation of a retroviral producer cell.

Using any of the vectors described herein, the codon modified nucleic acid molecule or fragment is operably linked to a promoter. A promoter refers to a DNA sequence that is recognized by RNA polymerase and initiates transcription. The promoter is suitable for expression in a cell, in particular a mammalian cell, but also including yeast, bacteria, insect cells.

The host cell may be any prokaryotic or eukaryotic cell. Thus, a nucleotide sequence derived from any one of SEQ ID Nos. 1-18, or a sequence or fragment complementary thereto, encoding all or a selected portion of a protein, can be used to produce a recombinant form of an polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures well known in the art.

Vectors that allow expression of a nucleic acid in a cell are referred to as expression vectors. Typically, expression vectors contain a nucleic acid operably linked to at least one transcriptional regulatory sequence. Regulatory sequences are art-recognized and are selected to direct expression of the subject nucleic acids. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject polypeptide, or alternatively, encoding a peptide which is an antagonist form of a subject polypeptide.

The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The nucleic acid or full-length gene is inserted into a vector typically by means of DNA ligase attachment to a cleaved restriction enzyme site in the vector. Alternatively, the desired nucleotide sequence may be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence.

Nucleic acids or full-length genes are linked to regulatory sequences as appropriate to obtain the desired expression properties. These may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art may be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to the nucleic acid is identified, its expression can be regulated in the cell to which the gene is native. For example, an endogenous gene of a cell can be regulated by an exogenous regulatory sequence as disclosed in U.S. Pat. No. 5,641,670, "Protein Production and Protein Delivery."

A number of vectors exist for the expression of recombinant proteins in yeast (see, for example, Broach et al (1983) in Experimental Manipulation of Gene Expression, ed. M. Inouye, Academic Press, p. 83, incorporated by reference herein). In addition, drug resistance markers such as ampicillin can be used Preferred mammalian expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see Molecular Cloning: A Laboratory Manual, 2'Ed., ed. by Sambrook, Fritsch and Maniatis (Cold Spring Harbor Laboratory Press: 1989) Chapters 16 and 17.

When it is desirable to express only a portion of a gene, e.g., a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., (1987) J Bacteriol. 169:751-757) and *Salmonella typhimurium* and its in vitro activity has been demonstrated on recombinant proteins (Miller et al. (1987) PNAS 84:2718-1722). Therefore, removal of an N-terminal methionine, if desired, can be achieved either in vivo by expressing polypeptides in a host which produces MAP (e.g., *E. coli* or CM89 or *S. cerevisiae*), or in vitro by use of purified MAP (e.g., procedure of Miller et al., supra).

A nucleic acid sequence of the present invention may also be administered by means of specialized delivery vectors useful in gene therapy. Gene therapy approaches are discussed for example by Verme et al, Nature 1997, 389:239-242. Both viral and non-viral vector systems can be used. Viral based systems include retroviral, lentiviral, adenoviral, adeno-associated viral, herpes viral, Canarypox and vaccinia-viral based systems. Preferred adenoviral vectors are those derived from non-human primates.

In addition to viral transfer methods, non-viral methods can also be employed to introduce a subject nucleic acid, e.g., a sequence represented by one of SEQ ID Nos. 1-14, or a sequence or fragment complementary thereto, into the tissue of an animal. Most nonviral methods of gene transfer rely on normal mechanisms used by mammalian cells for the uptake and intracellular transport of macromolecules. Non-viral targeting means rely on endocytic pathways for the uptake of the subject nucleic acid by the targeted cell. Exemplary targeting means of this type include liposomal derived systems, polylysine conjugates, and artificial viral envelopes.

A nucleic acid of any of SEQ ID Nos. 1-18 or a fragment or sequence complementary thereto, the corresponding cDNA, or the full-length gene may be used to express the partial or complete gene product. Appropriate nucleic acid constructs are purified using standard recombinant DNA techniques as described in, for example, Sambrook et al., (1989) Molecular Cloning: A Laboratory Manual, 2nd ed. (Cold Spring Harbor Press, Cold Spring Harbor, N.Y.), and under current regulations described in United States Dept. of HHS, National Institute of Health (NIH) Guidelines for Recombinant DNA research. The polypeptides encoded by the nucleic acid may be expressed in any expression system, including, for example, bacterial, yeast, insect, amphibian and mammalian systems. Suitable vectors and host cells are described, for example, in U.S. Pat. No. 5,654,173.

Nucleic acid molecules and constructs providing genes under the control of highly cell-type specific promoters and amplification promoter elements, can be incorporated into a vector and administered to any mammal, including a human. Many such vectors are commercially available, and other suitable vectors can be readily prepared and obvious to the skilled artisan. The exact design of the vector depends on such factors as the choice of the host cell to be transformed and/or the type of protein desired to be expressed. Suitable vectors can be produced by ligating the desired construct into a plasmid or viral vector suitable for expression in eukaryotic cells (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook, et al. (Cold Spring Harbor Laboratory Press, 1989) Chapters 16 and 17, the entireties of which are incorporated by reference herein).

Examples of vectors that can be used include, but are not limited to, plasmids such as pBR322, pUC, or Co1E1; adenovirus; Sindbis virus; simian virus 40; cytomegalovirus; and retroviral vectors such as murine sarcoma virus, mouse mammary tumor virus, Moloney murine leukemia virus, and Rous sarcoma virus. Bacterial vectors can be used, such as *Salmonella* ssp., *Yersinia enterocolitica, Shigella* spp., *Vibrio cholerae, Mycobacterium* strain BCG, and *Listeria monocytogenes*. Mini chromosomes such as MC and MCI, bacteriophages, cosmids (plasmids into which phage lambda cos sites have been inserted) and replicons (genetic elements that are capable of independent extrachromosomal replication).

The vectors described above can additionally comprise sequences encoding one or more selectable markers, including, but not limited to, the gene that encodes dihydrofolate reductase and the genes that confer resistance to neomycin, tetracycline, ampicillin, chloramphenicol, kanamycin and streptomycin resistance. To improve incorporation into the genome of the target cell (if desired), a retroviral vector can be used, and long terminal repeat (LTR) sequences can be added on either side of the expression construct (see, e.g., Vile, et al., Virology 214: 307-313 (1995), the entirety of which is incorporated by reference herein).

Delivery of a nucleic acid construct comprising a nucleotide sequence of the present invention under the control of a highly cell-type specific promoter can be by any means known in the art, including oral or intranasal administration; intramuscular, intradermal, intraperitoneal, or subcutaneous injection, including injection using a biological ballistic gun ("gene gun"). A gene gun provides a method for delivery of the immunogenic composition intradermally. Gene gun (particularly particle bombardment) administration techniques which involve coating the vector on to a bead (e.g. gold) which are then administered under high pressure into the epidermis; are described in Haynes et al, J Biotechnology 44: 37-42 (1996). Gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide, are accelerated to high speed within a helium gas jet generated by a hand held device, propelling the particles into a target tissue of interest, typically the skin. The particles are preferably gold beads of a 0.4-4.0 .mu.m, more preferably 0.6-2.0 .mu.m diameter and the DNA conjugate coated onto these and then encased in a cartridge or cassette for placing into the "gene gun". Other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Suitable techniques for introducing the naked polynucleotide or vector into a patient also include topical application with an appropriate vehicle. The nucleic acid may be administered topically to the skin, or to mucosal surfaces for example by intranasal, oral, intravaginal or intrarectal administration. The naked polynucleotide or vector may be present together with a pharmaceutically acceptable excipient, such as phosphate buffered saline (PBS). DNA uptake may be further facilitated by use of facilitating agents such as bupivacaine, either separately or included in the DNA formulation. Other methods of administering the nucleic acid directly to a recipient include ultrasound, electrical stimulation, electroporation and microseeding, which is described in U.S. Pat. No. 5,697,901.

Administration of the nucleic acid for therapeutic purposes can be repeated at any desired interval as needed to achieve therapeutic efficacy. Additional components can be added to a vector to improve its selective delivery to target cells and to repress its delivery to non-target cells. Examples of approaches that can be used include host range extension, entry enhancement, and host range restriction, as described in Peng and Russell, Cur. Opin. Biotech. 10: 454-457 (1999), the entirety of which is incorporated herein by reference.

Prime Boosting

The prime-boost regimen according to the invention can be used in animals of any age, advantageously young animals (e.g., animals that have detectable maternal antibodies and/or are suckling or nursing or breast-feeding), pre-adult animals (animals that are older than being a young animal but have not yet reached maturity or adulthood or an age to mate or reproduce), adult animals (e.g., animals that are of an age to mate or reproduce or are beyond such a period in life), and it is advantageous to employ the prime-boost regimen in pregnant females or females prior to giving birth, laying, or insemination.

The term "vector priming" is meant to refer to the delivery of a gene encoding a vaccine antigen by way of an expression vector. In certain embodiments, it means that the vector-based gene delivery will be a first exposure to the vaccine antigen, followed by one or more subsequent "booster" dose or doses of vaccine. The priming administration (priming) is the administration of a immunogenic or immunological composition type and may comprise one, two or more administrations. The boost administration is the administration of a second immunogenic or immunological composition type and may comprise one, two or more administrations, and, for instance, may comprise or consist essentially of annual administrations. The "boost" may be administered anytime after the priming, for example in certain embodiments from about 2 weeks to about 12 months after the priming, such as from about 6 week to about 6 months, or from about 3 to about 6 weeks after the priming, or from about 4 weeks after the priming. In a certain preferred example, ad35 is given as a first "priming" dose at birth, and an ad5 "boost" is given a 6 months of age.

The prime-boost regimen is especially advantageous to practice in a young animal, as it allows vaccination or immunization at an early age, for instance, the first administration in the prime-boost regimen when practiced on a young animal can be at an age at which the young animal has maternal antibodies. Another advantage of this regimen is that it can provide a degree of safety for pregnant females present in the same location or in close proximity to the young or to each other. Thus, the invention provides a prime-boost immunization or vaccination method against, for example, an RSV infection, and the method may be practiced upon a young animal, wherein the priming is done at a time that the young animal has maternal antibodies against RSV, with the boost advantageously at a time when maternal antibodies may be waning or decreasing or normally not present, such as a period of time post-breastfeeding.

The amounts (doses) administered in the priming and the boost and the route of administration for the priming and boost can be as herein discussed, such that from this disclosure and the knowledge in the art, the prime-boost regimen can be practiced without undue experimentation. Furthermore, from the disclosure herein and the knowledge in the art, the skilled artisan can practice the methods, kits, etc. herein with respect to any of the herein-mentioned target species.

Immunogenic Compositions

The invention includes an immunogenic composition comprising one or more codon modified viral genes or fragments. For example, the immunogenic composition may comprise one or more codon modified viral genes or fragments, where the codon-modified genes or fragments encode Paramyxovirus gene products. The Paramyxovirus can be selected from the group Avulavirus, Henipavirus, Morbillivirus, Respirovirus, Rubulavirus, Pneumovirus, Parainfluenza virus and Metapneumovirus. In specific examples, the Paramyxovirus is a Pneumovirus, and in more specific examples the Pneumovirus is Respiratory Syncytial Virus (RSV).

The immunogenic compositions of the invention include codon-modified genes or fragments thereof encode viral surface proteins. The codon-modified genes or fragments thereof may encode viral glycoproteins or fragments. The viral glycoproteins or fragments, in specific example, can encode, but are not limited to one or more of the fusion (F), membrane anchored attachment (Gr), matrix (M) or (M2), small hydrophobic (SH), nucleoprotein (N), surface (HN) glycoproteins, or fragments.

The immunogenic compositions of the invention do not include live, attenuated virus, for example live attenuated Paramyxovirus, or live attenuated RSV.

In one example, the immunogenic compositions comprise the Paramyxovirus membrane anchored attachment (Gr) glycoprotein. In another more specific embodiment of the invention, the codon-modified gene, or fragments thereof, comprises the membrane anchored attachment (Gr) glycoprotein of RSV. In certain examples, the codon-modified membrane anchored attachment (Gr) glycoprotein comprises SEQ ID NO: 2

In another example, the immunogenic compositions comprise the Paramyxovirus matrix (M) glycoprotein. In another more specific embodiment of the invention, the codon-modified gene, or fragments thereof, comprises the matrix (M) glycoprotein glycoprotein of RSV. In certain examples, the codon-modified matrix (M) glycoprotein comprises SEQ ID NO: 4.

In another example, the immunogenic compositions comprise the Paramyxovirus matrix (M) glycoprotein. In another more specific embodiment of the invention, the codon-modified gene, or fragments thereof, comprises the matrix (M2) glycoprotein of RSV. In certain examples, the codon-modified matrix (M2) glycoprotein comprises SEQ ID NO: 6.

In another example, the immunogenic compositions comprise the Paramyxovirus matrix fusion (M/M2) glycoprotein. In another more specific embodiment of the invention, the codon-modified gene, or fragments thereof, comprises the matrix fusion (M/M2) glycoprotein of RSV. In certain examples, the codon-modified matrix fusion (M/M2) glycoprotein comprises SEQ ID NO: 8.

In another example, the immunogenic compositions comprise the Paramyxovirus nucleoprotein (N). In another more specific embodiment of the invention, the codon-modified gene, or fragments thereof, comprises the nucleoprotein (N) of RSV. In certain examples, the codon-modified nucleoprotein (N) comprises SEQ ID NO: 10.

In another example, the immunogenic compositions comprise the Paramyxovirus SH envelope glycoprotein. In another more specific embodiment of the invention, the codon-modified gene, or fragments thereof, comprises the SH envelope glycoprotein of RSV. In certain examples, the codon-modified SH envelope glycoprotein comprises SEQ ID NO: 12.

In another example, the immunogenic compositions comprise the Paramyxovirus fusion (F) glycoprotein. In another more specific embodiment of the invention, the codon-modified gene, or fragments thereof, comprises the fusion (F) glycoprotein of RSV. In certain examples, the codon-modified fusion (F) glycoprotein comprises SEQ ID NO: 14. In other certain example, the codon-modified fusion (F) glycoprotein comprises SEQ ID NO: 16 or 18.

According to certain embodiments of the invention, the immunogenic compositions that comprising the Paramyxovirus fusion (F) glycoprotein or the codon-modified gene, or fragments thereof comprising the fusion (F) glycoprotein of RSV, or the codon-modified fusion (F) glycoprotein comprising SEQ ID NO: 1, may further comprise the cytoplasmic tail plus one amino acid residue of the fusion (F) glycoprotein of RSV. More specifically, the fragment comprising the cytoplasmic tail plus one amino acid residue corresponds to residues [1-551] of SEQ ID NO 14.

In other embodiments of the invention, the codon-modified genes, or fragments thereof, further comprise one or more additional mutations. A mutation may be a single-base alteration, e.g. a deletion, transition or a transversion, or a multiple base alteration.

The codon-modified genes of the invention are suitable for insertion into vectors and expression in host cells. Accordingly, codon modified genes are inserted into any of the vectors as described herein. In certain examples, the additional codon-modified gene or fragment comprises the membrane anchored attachment (Gr) glycoprotein of RSV. In other examples, the additional codon-modified gene or fragment comprises the matrix fusion (M/M2) glycoprotein of RSV. In other examples, the additional codon-modified gene or fragment comprises the nucleoprotein (N) glycoprotein of RSV. In other examples, the additional codon-modified gene or fragment comprises the envelope (SH) glycoprotein of RSV. In other examples, the additional codon-modified gene or fragment comprises one or more of SEQ ID NOs: 2, 4, 6, 8, 10, 12 or 14. Thus, the codon-modified gene or fragment inserted into vectors can be any one or more of a combination of SEQ ID NOs: 2, 4, 6, 8, 10, 12 or 14, or fragments thereof. It is up to the individual making the vectors to determine what the optimal codon-modified gene or fragment is to insert in to the vector.

For example, RSV encodes ten mRNAs and eleven proteins. Three of these are transmembrane surface proteins, namely the attachment G protein, fusion F protein involved in penetration, and small hydrophobic SH protein. G and F are the major viral neutralization and protective antigens. Four additional proteins are associated with the viral nucleocapsid, namely the RNA binding protein (N), the phosphoprotein (P), the large polymerase protein (L), and the transcription elongation factor (M2) ORF1. The M2-2 (ORF2 of M2) may also be involved in regulation of protein transcription. The matrix (M) protein is part of the inner virion and probably mediates association between the nucleocapsid and the envelope. Finally, there are two nonstructural proteins, (NS1) and (NS2), of unknown function. These proteins can be selectively altered in terms of expression levels, or can be added deleted, substituted or rearranged, in whole or in part, alone or in combination, with other desired modifications, to produce an immunogenic composition with novel characteristics. Desired modifications of the codon-modified genes or fragments encoding Paramyxovirus virus glycoproteins of the immunogenic compositions are typically selected to specify a desired phenotypic change, e.g., a change in viral growth, temperature sensitivity, ability to elicit a host immune response, attenuation, etc. These changes can be brought about either in a donor or recipient genome or antigenome by, e.g., mutagenesis of a parent clone to ablate, introduce or rearrange a specific gene(s) or gene region(s) (e.g., a gene segment that encodes a protein structural domain, such as a cytoplasmic, transmembrane or extracellular domain, an immunogenic epitope, binding region, active site, etc.). Genes of interest in this regard include glycoprotein genes of Paramyxovirus virus genomes, for example of the all of the genes of the RSV genome: 3'-NS1-NS2-N-P-M-SH-G-F-M2-L-5', as well as heterologous genes from other RSV.

The immunogenic compositions of the invention can include chimeric immunogenic compositions, including vaccines. Chimeric respiratory syncytial virus (RSV) and vaccine compositions thereof are produced by introducing one or more heterologous gene(s) or gene segment(s) from one RSV subgroup or strain into a recipient RSV background of a different subgroup or strain. U.S. Pat. No. 6,689,367, incorporated by reference herein in its entirety, describes chimeric RSV that are recombinantly engineered to incorporate nucleotide sequences from more than one RSV strain or subgroup to produce an infectious, chimeric virus or subviral particle.

Accordingly, an exemplary chimeric immunogenic composition can include one or more codon modified genes or fragments thereof, wherein the codon-modified genes or fragments encode Paramyxovirus virus glycoproteins from one from strain or subgroup virus combined with one or more heterologous gene(s) or gene segment(s) of a different Paramyxovirus strain or subgroup virus. For example, a chimeric immunogenic composition may incorporate one or more codon modified genes or fragments thereof, wherein the codon-modified genes or fragments encode one or more of the fusion (F), membrane anchored attachment (Gr), matrix (M) or (M2), envelope (SH), nucleoprotein (N), or surface (HN) glycoproteins. Alternatively, the chimeric immunogenic composition may incorporate one or more codon modified genes or fragments thereof encoding a cytoplasmic domain, transmembrane domain, or ectodomain of the fusion (F), membrane anchored attachment (Gr), matrix (M) or (M2), envelope (SH), nucleoprotein (N), or surface (HN) glycoproteins. These immunogenic codon-modified genes or fragments are particularly useful within chimeric immunogenic compositions because they can generate novel immune responses in an immunized host. Chimeric immunogenic compositions can also include codon-modified genes, or fragments thereof, that further comprise one or more additional mutations.

In certain immunogenic compositions, chimeric immunogenic compositions may be provided wherein genes or gene segments within a human Paramyxovirus virus, for example, a human RSV, are replaced with counterpart heterologous genes or gene segments from a non-human Paramyxovirus virus, for example a non-human RSV, e.g., a bovine or murine virus. Alternatively, chimeric Paramyxovirus virus may incorporate genes or gene segments from a human virus in a non-human recipient. Substitutions, deletions, and additions of Paramyxovirus virus genes or gene segments in this context can include part or all of one or more of the NS1, NS2, N, P, M, SH, M2(ORF1), M2(ORF2) and L genes, or non-immunogenic parts of the G and F genes. Also, human and non-human Paramyxovirus virus cis-acting sequences, such as promoter or transcription signals, can be replaced with, respectively, non-human or human counterpart sequences. Thus, bovine immunogenic compositions can be provided by inserting human non-coding genes or fragments thereof into a bovine Paramyxovirus virus background.

Immunogenic compositions including vaccines may be prepared as injectables, as liquid solutions, suspensions or emulsions. The active immunogenic ingredients may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneous, intradermal or intramuscularly injection. Alternatively, the immunogenic compositions formulated according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient(s) in the range of about 0.5 to about 10%, preferably about 1 to 2%. Oral formulations may include normally employed carriers such as, pharmaceutical grades of saccharine, cellulose and magnesium carbonate. These compositions can take the form of solutions, suspensions, tablets, pills, capsules, sustained release formulations or powders and contain about 1 to 95% of the active ingredients, preferably about 20 to about 75%.

Vaccines are typically administered parenterally via injections. Traditional parenteral immunization regimes are known to have a number of drawbacks. For example, many individuals possess a natural fear of injections and may experience psychological discomfort as a result. Furthermore, many individuals find injections physically uncomfortable. Moreover, parenteral vaccination (e.g. intramuscular, subcutaneous etc.) is not an effective means of eliciting local antibody production if there has been no previous local exposure (e.g. by way of infection).

An effective local and/or topical administration regime is therefore desirable.

In the case of some diseases, it would be advantageous to stimulate the mucosal immune system. In order to do this, the vaccine must be applied topically to a mucosal surface. Thus, in certain cases (e.g. in the case of infections of the upper respiratory tract), it would be beneficial to obtain more effective stimulation of the local mucosal immune system of the respiratory tract.

Accordingly, a number of attempts have been made to develop mucosal vaccines. One drawback, however, is that inactivated vaccines are often poorly immunogenic when given mucosally. In order to overcome this problem, different approaches to improving the immunogenicity of vaccines given orally or intranasally have included the use of adjuvants (as described below), and encapsulation of the vaccine in a variety of microspheres.

The immunogenic preparations and vaccines are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and, if needed, to produce a cell-mediated immune response. Precise amounts of active ingredients required to be administered depend on the judgment of the practitioner. However, suitable dosage ranges are readily determinable by one skilled in the art and may be of the order of micrograms to milligrams of the active ingredient(s) per vaccination. Suitable regimes for initial administration and booster doses are also variable, but may include an initial administration followed by subsequent booster administrations. The dosage may also depend on the route of administration and will vary according to the size of the host.

The immunogenic preparations or vaccines are administered in one or more doses as required to achieve the desired effect. Thus, the immunogenic preparations or vaccines may be administered in 1, 2, 3, 4, 5, or more doses. Further, the doses may be separated by any period of time, for example hours, days, weeks, months, and years.

Immunogenicity can be significantly improved if an adjuvant is co-administered with the immunostimulatory composition. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Chemically, the adjuvants are a highly heterogeneous group of compounds with only one thing in common: their ability to enhance the immune response—their adjuvanticity. They are highly variable in terms of how they affect the immune system and how serious their adverse effects are due to the resultant hyperactivation of the immune system. In the instant invention, adjuvants are not considered in the setting with live attenuated vaccine compositions, but for use with the immunogenic compositions as described herein.

The mode of action of adjuvants was described by Chedid (Ann. immunol. Inst. Pasteur 136D:283.1985) as: the formation of a depot of antigen at the site of inoculation, with slow release; the presentation of antigen immunocompetent cells; and the production of various and different lymphokines (interleukins and tumor necrosis factor).

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) RIBI™ adjuvant system (RAS), (Ribi Immunochem, Hamilton, Mo.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as STIMULON™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59 are preferred.

Certain adjuvants have been shown, when co-administered with vaccine antigens, to further boost the effectiveness of vaccine compositions by stimulating the immune response (see e.g. Hibberd et al, Ann. Intern. Med., 110, 955 (1989)). Examples of adjuvants which have been shown to be effective include interferon alpha, *Klebsiella pneumoniae* glycoprotein and interleukin-2.

Chitosans are derivatives of chitin or poly-N-acetyl-D-glucosamine in which the greater proportion of the N-acetyl groups have been removed through hydrolysis. European Patent Application 460 020 discloses pharmaceutical formulations including chitosans as mucosal absorption enhancers.

The choice of any of these adjuvants reflects a compromise between a requirement for adjuvanticity and an acceptable low level of adverse reactions.

Also contemplated by the invention is chimeric RSV. Chimeric RSV and immunogenic compositions thereof are produced by combining one or more heterologous gene(s) or gene segment(s) from one RSV codon-modified subgroup or strain with another. Chimeric RSV of the invention can incorporate codon modified genes or fragments from more than one RSV strain or subgroup to produce a chimeric immunogenic particle. In this manner, for example, candidate vaccine viruses are recombinantly engineered to elicit an immune response against RSV in a mammalian host susceptible to RSV infection, including humans and non-human primates. Chimeric codon-modified RSV according to the invention may elicit an immune response to a specific RSV subgroup or strain, or a polyspecific response against multiple RSV subgroups or strains.

Dosage and Mode of Administration

In general, the immunogenic preparations and vaccines are administered in a manner compatible with the dosage formulation, and in such amount as will be therapeutically affective, protective and immunogenic. The quantity to be administered depends on the subject to be treated. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage may also depend on the route of administration and will vary according to the size of the host.

The intranasal compositions according to the invention can be formulated as liquids or dry powders, for administration as aerosols, drops or insufflations.

Preferably, the compositions according to the invention are formulated as dry powders or in the form of microspheres.

The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, or any of the adjuvants mentioned herein, which are materials well known in the art.

Compositions for administration as nasal drops may contain one or more excipients of the type usually included in such compositions, for example preservatives, viscosity adjusting agents, tonicity adjusting agents, buffering agents and the like.

Alternatively, the immunogenic compositions can be delivered as cochleate formulations. Cochleates are a novel lipid-based delivery system that have the potential for oral administration of hydrophobic drugs. Cochleates are stable phospholipid-cation crystalline structures consisting of a spiral lipid bilayer sheet with no internal aqueous space, and are comprised mainly of phosphatidylserine. They have a defined multilayered structure consisting of a continuous, solid, lipid bilayer sheet rolled up in a spiral, with no internal aqueous space. Papahadjopoulos et al. first described cochleates in 1975 as an intermediate in the preparation of large unilamellar vesicles (Papahadjopoulos, D., W. J. Vail, K. Jacobson, and G. Poste. 1975. Cochleate lipid cylinders: formation by fusion of unilamellar lipid vesicles. Biochim. Biophys. Acta 394:483-491). Cochleates have been used to deliver protein, peptide, and DNA for vaccine and gene therapy applications (Mannino, R. J., and S. Gould-Fogerite. 1997. Antigen cochleate formulations for oral and systemic vaccination in new generation vaccines, p. 1-9. In M. M. Levine (ed.), New generation vaccines. Marcel Dekker, New York, N.Y.) and have been used recently as a drug delivery system (L. Zarif, I. Segarra, T. Jin, D. Hyra, and R. J. Mannino, Proceedings of the 26th International Symposium on Controlled Release of Bioactive Materials, abstr. p. 964-965, 1999).

In another embodiment, the immunogenic compositions can be delivered in an exosomal delivery system. Exosomes are small membrane vesicles that are released into the extracellular environment during fusion of multivesicular bodies with plasma membrane. Exosomes are secreted by various cell types including hematopoietic cells, normal epithelial cells and even some tumor cells. Exosomes are known to carry MHC class I, various costimulatory molecules and some tetraspanins. Recent studies have shown the potential of using native exosomes as immunologic stimulants.

Also contemplated by the invention is delivery of the immunogenic composition using nanoparticles. For example, the immunogenic compositions provided herein can contain nanoparticles having at least one or more immunogenic compositions linked thereto, e.g., linked to the surface of the nanoparticle. A composition typically includes many nanoparticles with each nanoparticle having at least one or more immunogenic compositions linked thereto. Nanoparticles can be colloidal metals. A colloidal metal includes any water-insoluble metal particle or metallic compound dispersed in liquid water. Typically, a colloid metal is a suspension of metal particles in aqueous solution. Any metal that can be made in colloidal form can be used, including gold, silver, copper, nickel, aluminum, zinc, calcium, platinum, palladium, and iron. In some cases, gold nanoparticles are used, e.g., prepared from $HAuCl_4$. Nanoparticles can be any shape and can range in size from about 1 nm to about 10 nm in size, e.g., about 2 nm to about 8 nm, about 4 to about 6 nm, or about 5 nm in size. Methods for making colloidal metal nanoparticles, including gold colloidal nanoparticles from $HAuCl_4$, are known to those having ordinary skill in the art. For example, the methods described herein as well as those described elsewhere (e.g., US 2001/005581; 2003/0118657; and 2003/0053983) are useful guidance to make nanoparticles.

In certain cases, a nanoparticle can have two, three, four, five, six, or more immunogenic compositions linked to its surface. Typically, many molecules of an immunogenic composition are linked to the surface of the nanoparticle at many locations. Accordingly, when a nanoparticle is described as having, for example, two immunogenic compositions linked to it, the nanoparticle has two distinct immunogenic compositions, each having its own unique molecular structure, linked to its surface. In some cases, one molecule of an immunogenic composition can be linked to the nanoparticle via a single attachment site or via multiple attachment sites.

An immunogenic composition can be linked directly or indirectly to a nanoparticle surface. For example, linked directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In cases where the nanoparticle includes gold, a linker can be any thiol-containing molecule. Reaction of a thiol group with the gold results in a covalent sulfide (—S—) bond. Linker design and synthesis are well known in the art.

Any type of immunogenic composition or any type of additional agent can be linked to a nanoparticle. For example, an additional agent can be a therapeutic agent that has a therapeutic effect in the body. Examples of therapeutic agents include, without limitation, anti-angiogenic agents, anti-inflammatory agents, anti-bacterial agents, anti-fungal agents, growth factors, immunostimulatory agents. A therapeutic agent can be in any physical or chemical form, including an antibody, an antibody fragment, a receptor, a receptor fragment, a small-molecule, a peptide, a nucleic acid, and a peptide-nucleic acid.

A therapeutic agent can function as a targeting agent in addition to functioning as a therapeutic agent. A targeting functionality can allow nanoparticles to accumulate at the target at higher concentrations than in other tissues. In general, a targeting molecule can be one member of a binding pair that exhibits affinity and specificity for a second member of a binding pair. For example, an antibody or antibody fragment therapeutic agent can target a nanoparticle to a particular region or molecule of the body (e.g., the region or molecule for which the antibody is specific) while also performing a therapeutic function. In some cases, a receptor or receptor fragment can target a nanoparticle to a particular region of the body, e.g., the location of its binding pair member. Other therapeutic agents such as small molecules can similarly target a nanoparticle to a receptor, protein, or other binding site having affinity for the therapeutic agent.

A nanoparticle can have a diagnostic agent linked thereto. In some cases, a diagnostic agent and a therapeutic agent can both be linked to a nanoparticle. A diagnostic agent can allow the imaging of a nanoparticle in vivo. For example, a patient administered a nanoparticle having a diagnostic agent and a therapeutic agent linked thereto can be imaged once, e.g., to locate and/or stage a tumor, or at multiple time points, e.g., to monitor the efficacy of the therapeutic agent.

Aerosol delivery of the immunogenic compositions as described herein is possible, and methods have been described in the art. For example, the immunogenic compositions can also be formulated for aerosol administration. For administration by inhalation, the compositions are delivered in the form of an aerosol spray from a pressurized container or dispenser which contains a suitable propellant, e.g., a gas such as carbon dioxide, or a nebulizer.

Formulations suitable for use with a nebulizer, either jet or ultrasonic, will typically comprise the immunogenic composition, dissolved in solution at an appropriate dosage as determined by a healthcare professional, and may also include a buffer and a simple sugar (e.g., for stabilization and/or regulation of osmotic pressure).

Formulations for use with a metered-dose inhaler device will generally comprise a finely divided powder containing the immunogenic composition suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant, if necessary.

The liquid aerosol formulations contain immunogenic compositions and a dispersing agent in a physiologically acceptable diluent. The dry powder aerosol formulations of the present invention consist of a finely divided solid form of immunogenic compositions and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects are well known in the art, and manipulation of formulations, aerosolization means and construction of a delivery device require at most routine experimentation by one of ordinary skill in the art.

Systems of aerosol delivery, such as the pressurized metered dose inhaler and the dry powder inhaler are disclosed in Newman, S. P., Aerosols and the Lung, Clarke, S. W. and Davia, D. editors, pp. 197 22.

In a further embodiment, an aerosol formulation of the present invention can include other therapeutically or pharmacologically active ingredients in addition to immunogenic compositions, such as but not limited to an antibiotic, an antifungal, a steroid, a non-steroidal anti-inflammatory drug, etc.

Liquid aerosol formulations are also contemplated methods of delivery. In general such dosage forms contain immunogenic compositions in a pharmaceutically acceptable diluent. Pharmaceutically acceptable diluents include but are not limited to sterile water, saline, buffered saline, dextrose solution, and the like. For example, a diluent that may be used in the present invention or the pharmaceutical formulation of the present invention is phosphate buffered saline, or a buffered saline solution generally between the pH 7.0 8.0 range, or water.

The liquid aerosol formulation of the present invention may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising immunogenic compositions and another therapeutically effective drug, such as an antibiotic, a steroid, a non-steroidal anti-inflammatory drug, etc.

Aerosol dry powder formulations are also contemplated by the present invention. The present aerosol formulation can be prepared as a dry powder formulation comprising a finely divided powder form of immunogenic compositions and a dispersant.

Formulations for dispensing from a powder inhaler device will comprise a finely divided dry powder containing immunogenic compositions and may also include a bulking agent, such as lactose, sorbitol, sucrose, or mannitol in amounts which facilitate dispersal of the powder from the device, e.g., 50 to 90% by weight of the formulation. The immunogenic compositions should most advantageously be prepared in particulate form. Bulking agents are useful in conjunction with the present formulation, and include such agents as lactose, sorbitol, sucrose, or mannitol, in amounts that facilitate the dispersal of the powder from the device.

The immunogenic composition should be administered to the patient in an amount effective to stimulate a protective immune response in the patient. For example, the immunogenic composition may be administered to humans in one or more doses, each dose containing is $10^3$ to $10^{11}$ PFU, for example $10^2$ or $10^3$ or $10^4$ or $10^5$ or $10^6$, more preferably $10^3$ to $10^9$ or $10^{10}$ or $10^{11}$ PFU.

The immunogenic compositions or vaccines as discussed herein can also be combined with at least one conventional vaccine (e.g., inactivated, live attenuated, or subunit) directed against the same pathogen or at least one other pathogen of the species to which the composition or vaccine is directed.

Certain subjects can be identified as suited for administration of the immunogenic compositions of the invention. In certain preferred embodiments, the subjects would receive an immunogenic composition comprising a vector prime.

For example, infants are suited to receive immunogenic compositions consisting of a vector prime boost of, for example, a first dose at birth and a second dose at, for example, 1 mo of age or any period of time thereafter. The elderly or immunocompromised are another population that can be identified as subjects that can be administered an immunogenic composition consisting of a vector prime boost.

Kits or Pharmaceutical Systems

The present compositions may be assembled into kits or pharmaceutical systems for use in eliciting an immune response in a subject. In particular embodiments, the kits of the invention can be used for eliciting an immune response capable of preventing a viral infection in a subject. The kits can comprise one or more vectors comprising one or more codon modified viral genes or fragments, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use in eliciting an immune response capable of preventing a viral infection in a subject.

The present compositions may be assembled into kits or pharmaceutical systems for use in eliciting an immune response capable of preventing Paramyxoviral infection in a subject. The kits can comprise one or more vectors comprising one or more codon modified Paramyxovirus genes or fragments, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use in eliciting an immune response capable of preventing Paramyxoviral infection in a subject.

The present compositions may also be assembled into kits or pharmaceutical systems for use in treating a subject having a viral infection. The kits can comprise one or more vectors comprising one or more codon modified genes or fragments, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use in treating a subject having a viral infection.

The present compositions may also be assembled into kits or pharmaceutical systems for use in treating a subject having a having Paramyxoviral infection. The kits can comprise one or more vectors comprising one or more codon modified genes or fragments, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use in treating a subject having Paramyxoviral infection.

The present compositions may also be assembled into kits or pharmaceutical systems for use in eliciting an immune response capable of preventing a viral infection, for example a Paramyxovirus infection, in a subject. The kits can comprise one or more vectors comprising one or more codon modified viral genes or fragments thereof encoding one or more polypeptides of any of the aspects of the invention described herein, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use in eliciting an immune response capable of preventing viral infection, for example a Paramyxovirus infection in a subject.

The present compositions may also be assembled into kits or pharmaceutical systems for use in enhancing protein production of a viral glycoprotein, for example in specific embodiments a Paramyxovirus glycoprotein, in a subject. The kits can comprise one or more vectors comprising one or more codon modified viral genes or fragments thereof encoding one or more polypeptides of any of the aspects of the invention described herein, and a pharmaceutically acceptable carrier. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for use enhancing protein production of a viral glycoprotein, for example in specific embodiments, Paramyxovirus glycoprotein, in a subject.

The kits or pharmaceutical systems are used to treat viral infection. Viral infection can be Paramyxovirus infection. The Paramyxovirus can be any of, but limited to Avulaviral infection, Henipaviral infection, Morbilliviral infection, Respiroviral infection, Rubulaviral infection, Pneumoviral infection, and Metapneumoviral infection. Further, it is within the scope of the invention that the Paramyxovirus is selected from the group consisting of: human, avian, murine, simian, bovine or ovine Paramyxovirus. In specific embodiments of the invention the Pnuemovirus is Respiratory Syncytial Virus (RSV).

The kits of the invention can contain one or more vectors. For example, the kits might contain a plurality of vectors comprising one or more Paramyxovirus codon modified genes or fragments. Accordingly, the kits may contain 1, 2, 3, 4, 5, 6, or more vectors, each comprising one or more Paramyxovirus codon modified gene or fragment thereof.

Kits or pharmaceutical systems according to the invention described herein may further contain an adjuvant. Adjuvants can be selected from, but are not limited to, oil emulsions, mineral compounds, bacterial products, liposomes, and immunostimulating complexes. Examples of adjuvants contained in the kits include, but are not limited to, aluminum salts, oil-in-water emulsion formulations (with or without other specific immunostimulating agents such as muramyl peptides or bacterial cell wall components, such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) RIBI™ adjuvant system (RAS), (Ribi Immunochem, Hamilton, Mo.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as STIMULON™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Examples include Alum, and MF59, interferon alpha, *Klebsiella pneumoniae* glycoprotein and interleukin-2, and chitosans.

Having now generally described the invention, the same will be more readily understood through reference to the following Examples, which are provided by way of illustration, and are not intended to be limiting of the present invention, unless specified.

EXAMPLES

Example 1

Figure 1:
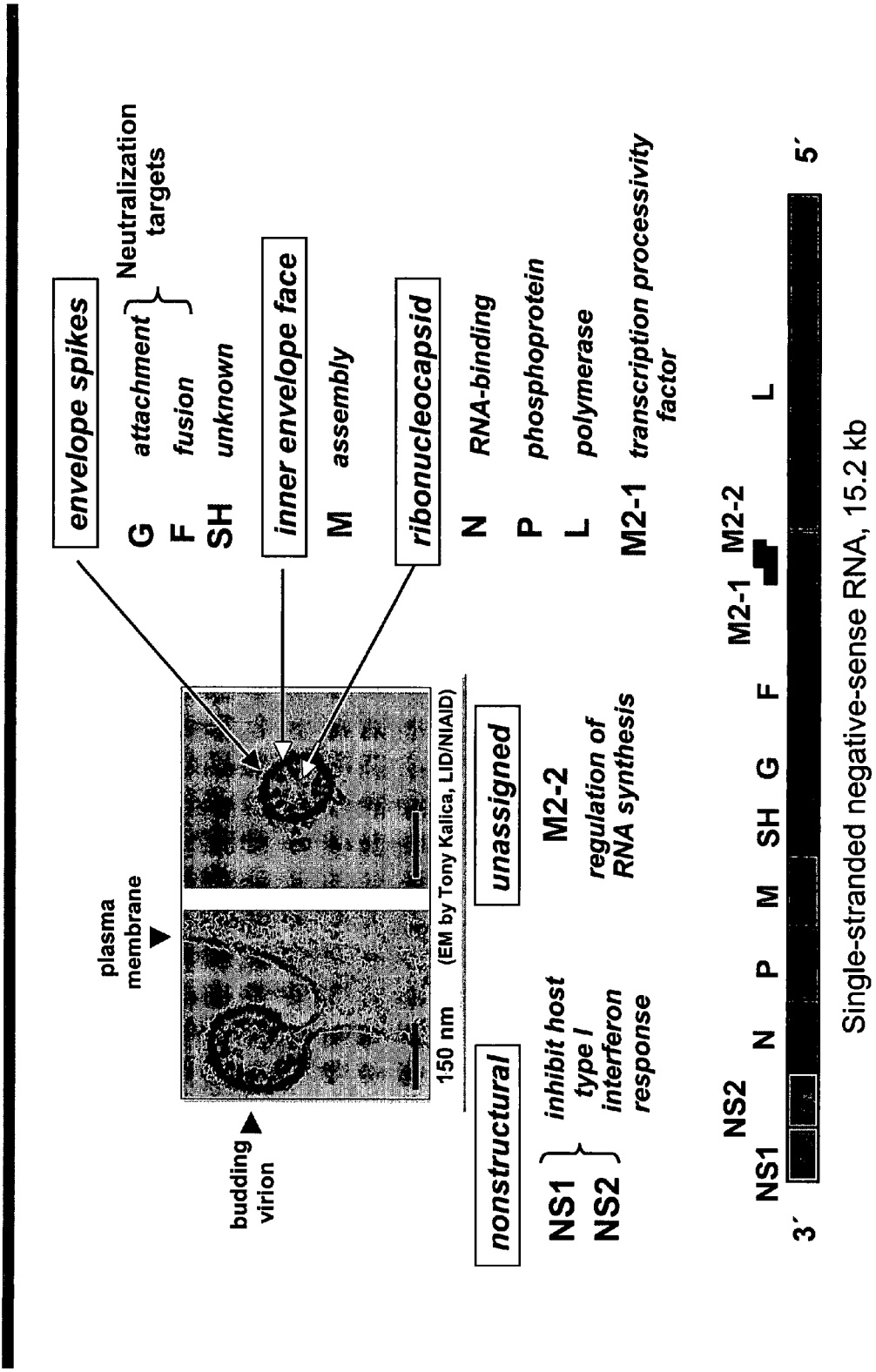
FIG. 1 shows the Respiratory Syncytial virus (RSV) virion, genome and proteins.
Figure 2A:
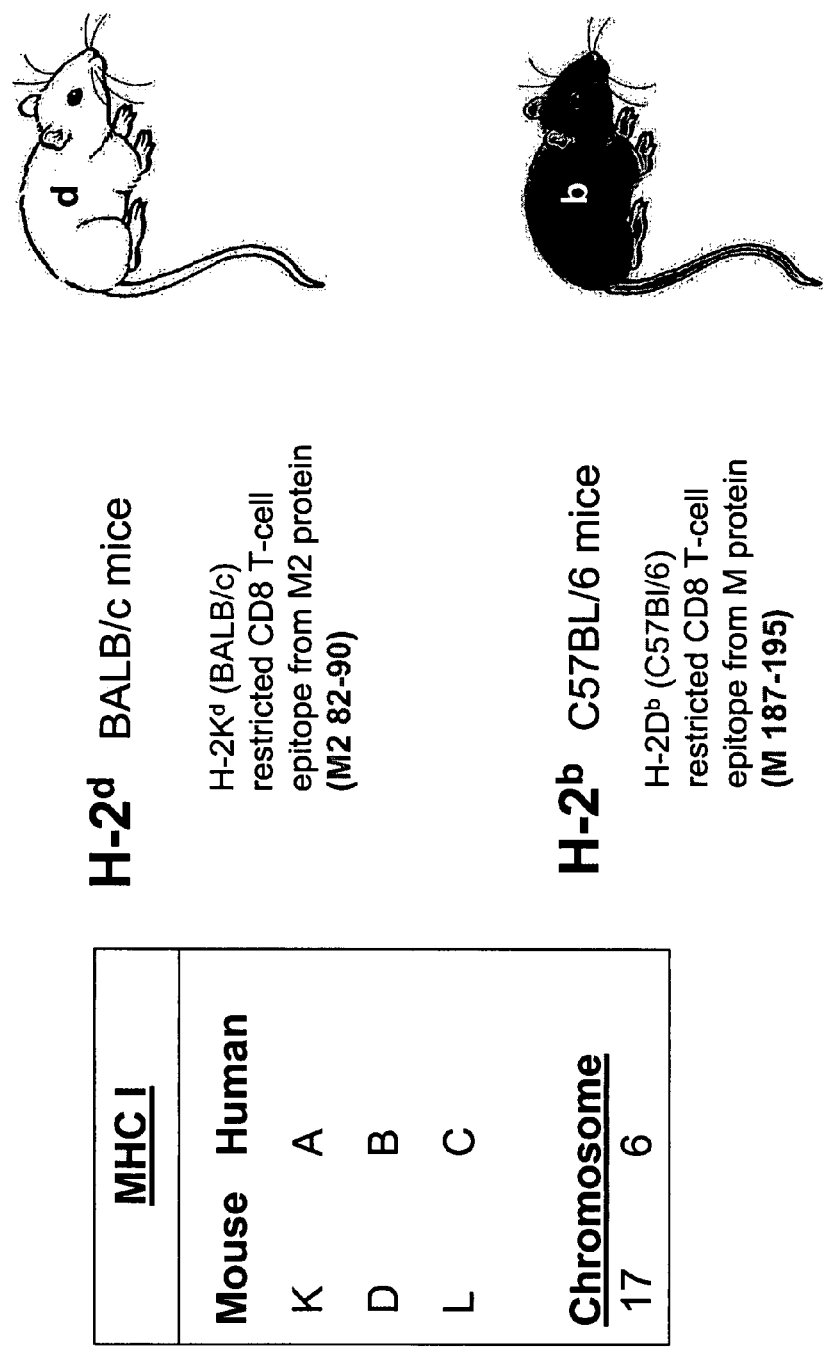
FIG. 2 (a-c) (a) is a schematic showing mouse MHC class I genetics. (b) is a schematic depicting generation of the CB6F1/J Hybrid mouse (SYIGSINNI peptide disclosed as SEQ ID NO: 19 and NAITNAKII peptide disclosed as SEQ ID NO: 20). (c) is a panel of four graphs that show epitope- and mouse strain-specific CD8+ T cell responses. The data represents flow cytometry data for surface markers and intracellular cytokine production after vitro peptide stimulation.
Figure 2B:
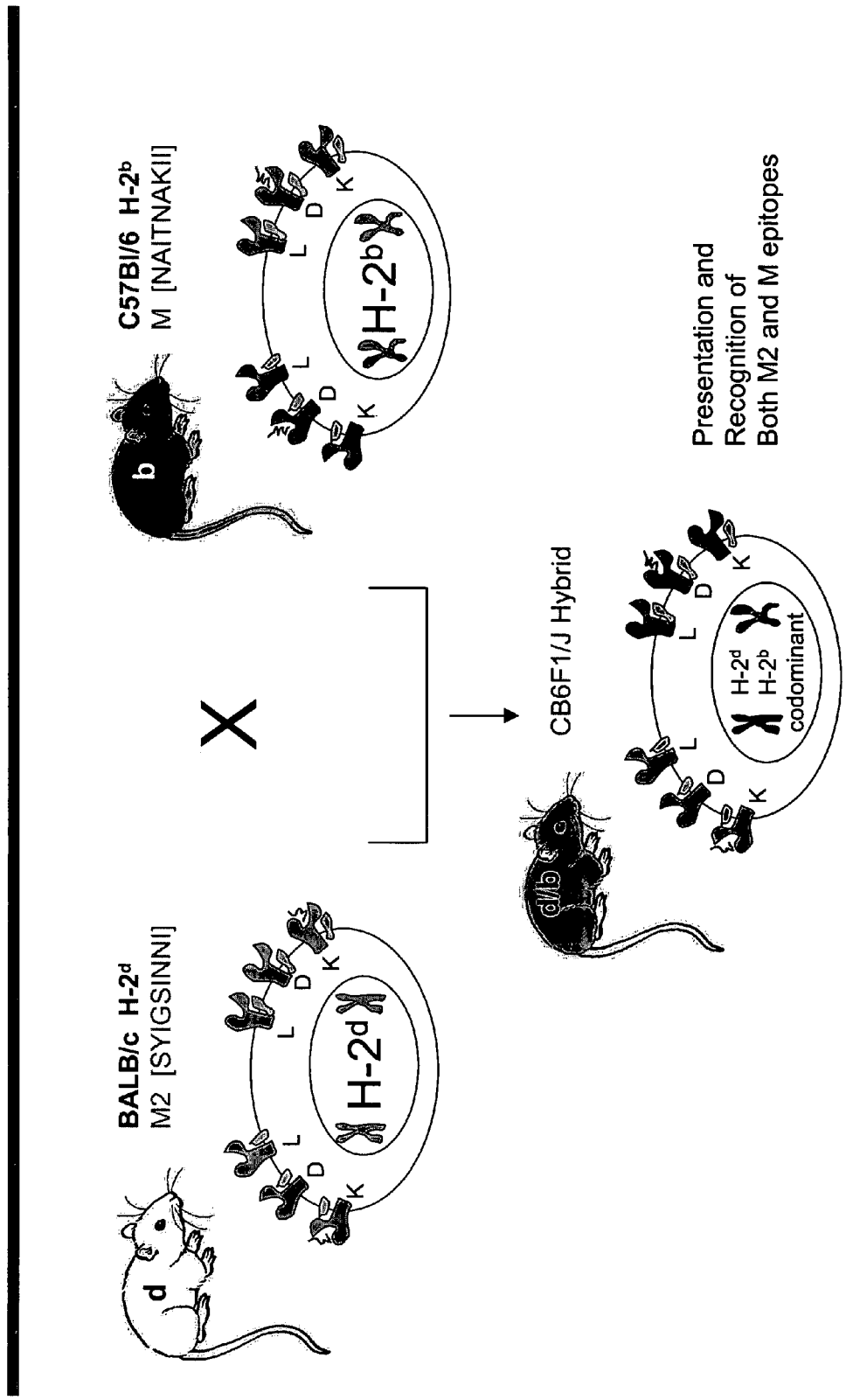
Figure 2C:
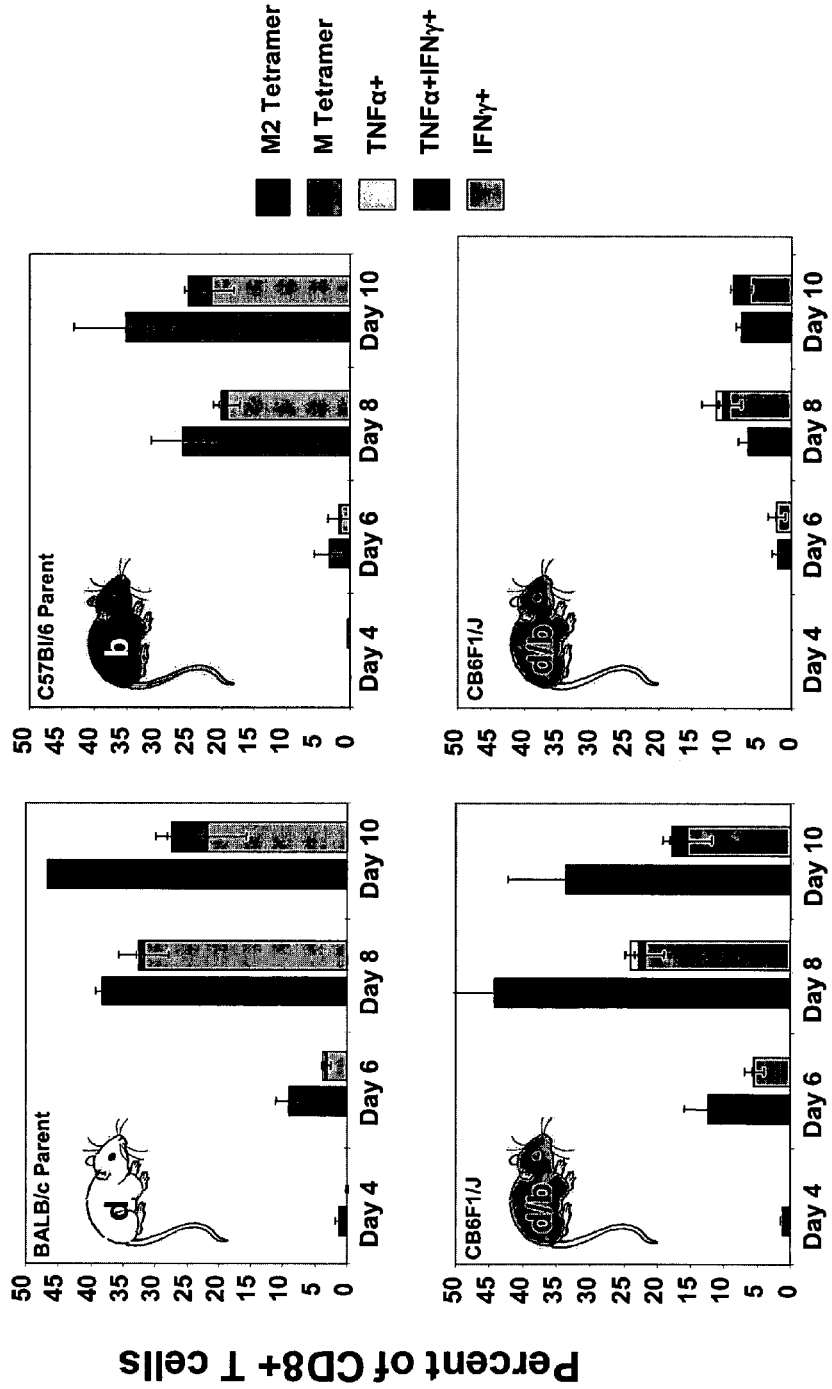
Figure 3:
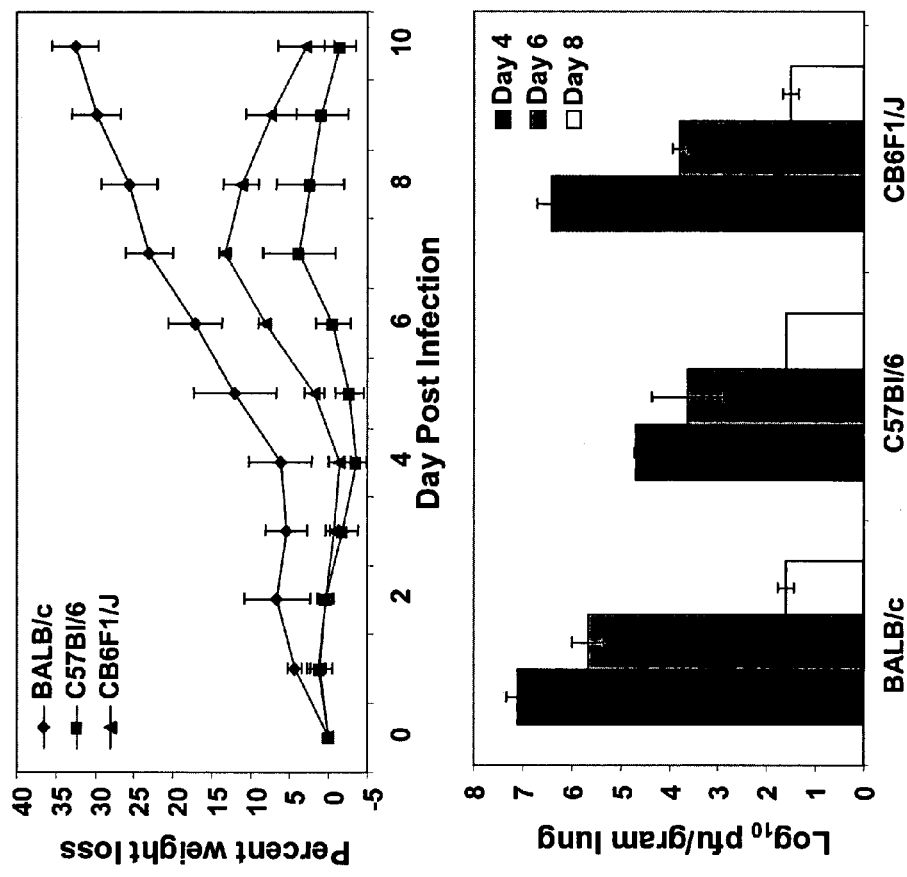
FIG. 3 is two graphs showing RSV infection of BALB/c, C57B1/6, and CB6F1/J mice. The top panel shows percent weight loss up to 10 days post-infection. The bottom panel shows the kinetics of viral clearance following RSV infection.

Prior efforts to immunize mice with gene-based vectors in the early 1990's were unsuccessful. The definition of CD8+ T cell epitopes in the matrix (M) protein and the M2 protein of RSV (FIG. 1) provided the opportunity to accurately measure the immune response induced by gene-based vectors using gene inserts codon-modified for improved expression in mammalian cells. The M2 epitope (aa82-90) is restricted to H-2Kd (BALB/c mice), and the M epitope (aa187-195) is restricted to H-2 Db (C57Bl/6 mice) (FIG. 2a). Therefore, both epitopes can be recognized by the F1 hybrid mouse (CB6F1/J) (FIG. 2b) and epitope-specific T cell responses can be measured with TCR-specific tetramers or by peptide stimulation (FIG. 2c). Either the parent strains or hybrid mice can be used to evaluate not only the individual immune responses, but the impact of immunization on protection from illness or virus replication in lung (FIG. 3).

Figure 5A:
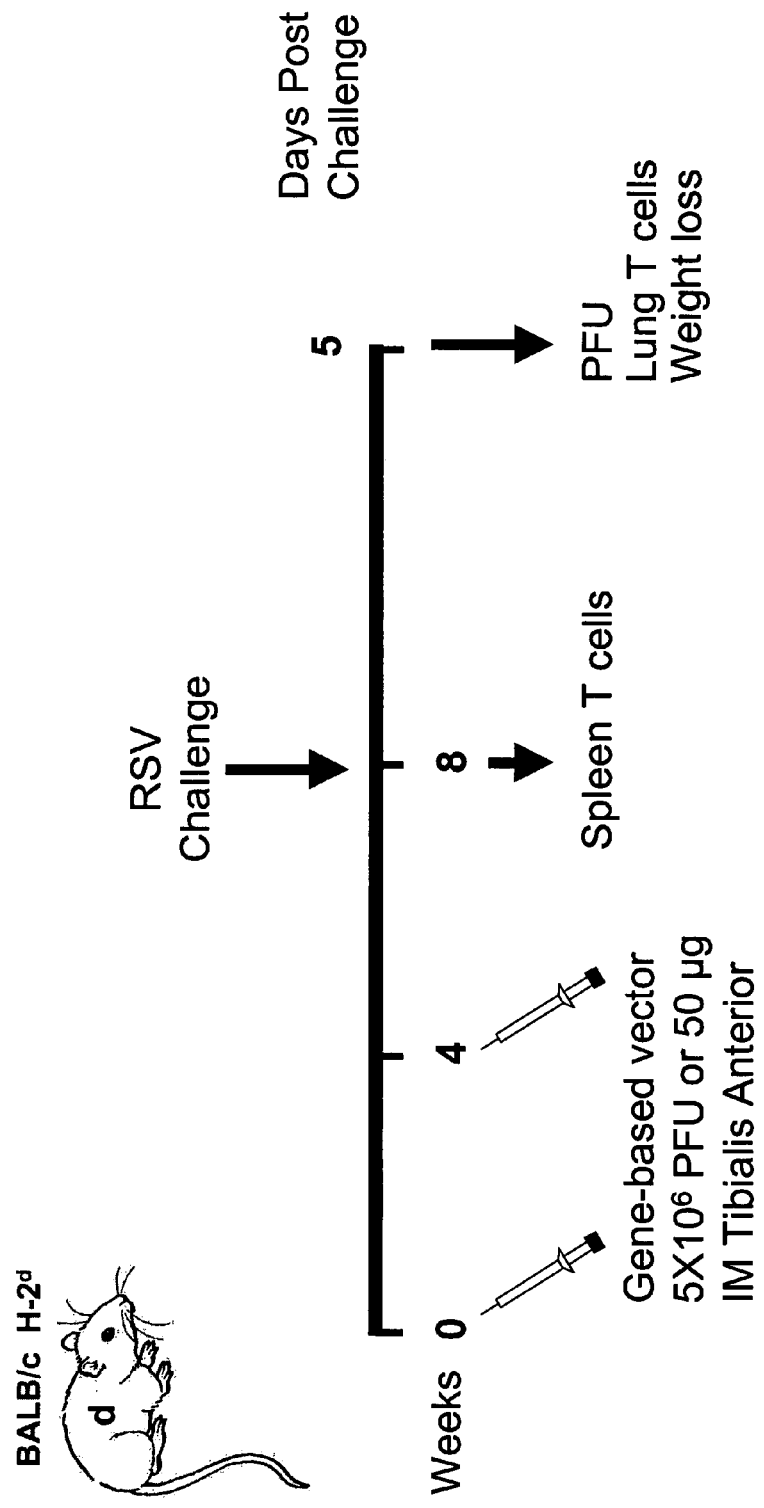
FIG. 5 (a-c) (a) is a schematic showing the experimental protocol schema that was used. (b) shows the gating strategy used for RSV-specific T-cell analysis. (c) is two graphs that show weight loss and virus replication after RSV challenge. BALB/c H-2d mice were immunized with M2 vectors. In the panel of the left, weight loss after RSV challenge is shown as percent of initial weight in days after infection. The inset shows the vector used. The panel on the right shows virus replication as $Log_{10}$ pfu/gram in the lung after RSV challenge.
Figure 5B:
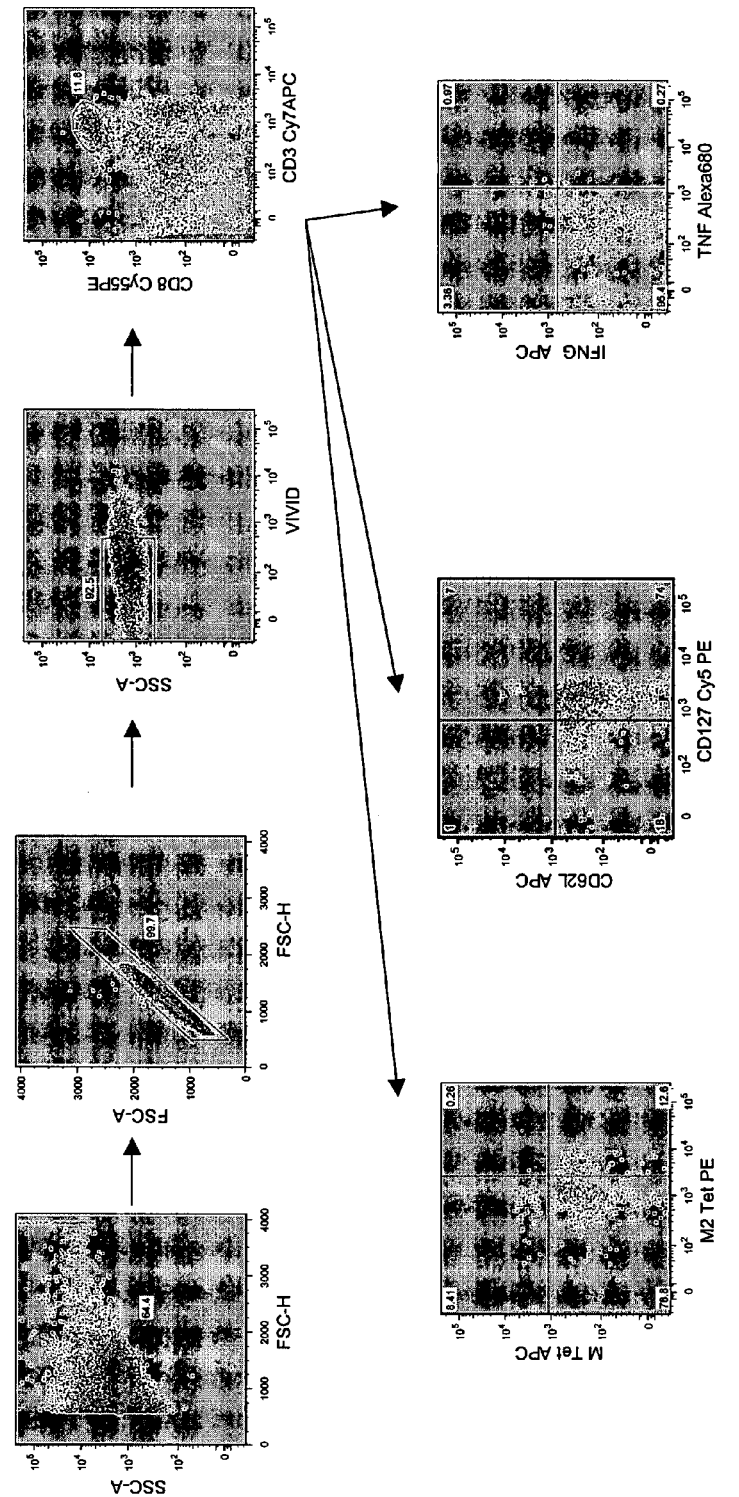
Figure 6:
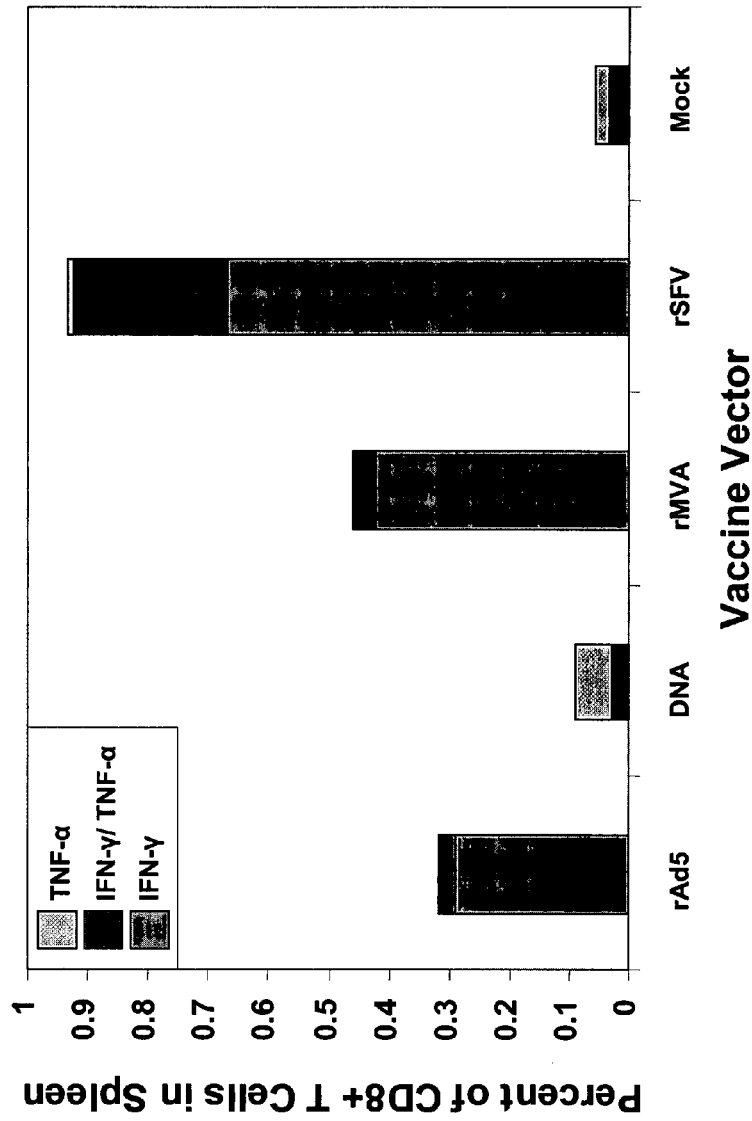
FIG. 6 is a graph showing M2-specific responses in the spleen prior to challenge. BALB/c H-2d mice were immunized with M2 vectors. rAd5, DNA, rMVA, rSFV, and Mock vaccine vectors were used.
Figure 7:
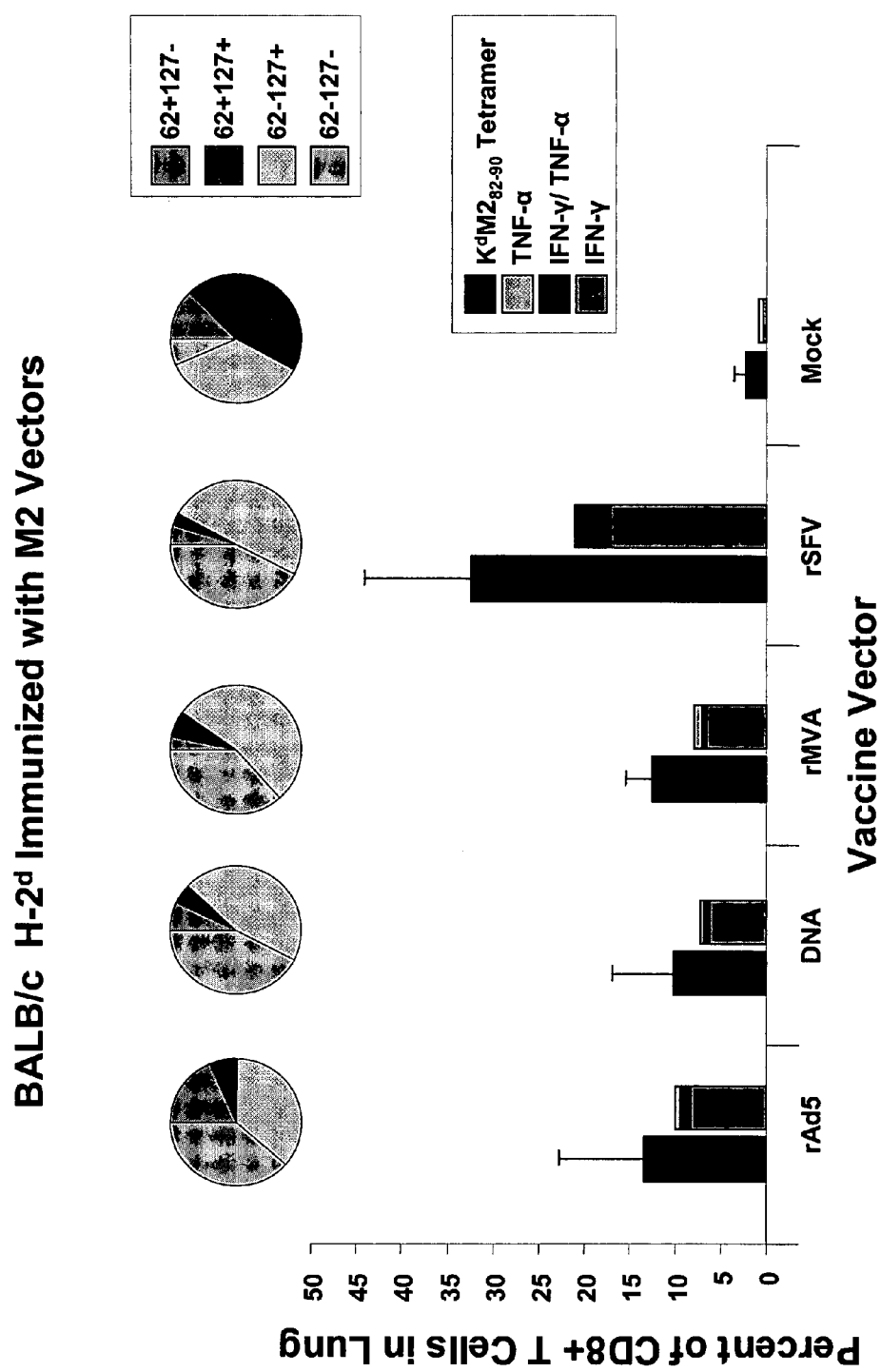
FIG. 7 is a graph showing the M-2 specific CD-8+ T cell responses on day 5 post RSV challenge. BALB/c H-2d mice were immunized with M2 vectors. rAd5, DNA, rMVA, rSFV, and Mock vaccine vectors were used. The bar graph represents the percentage of M2-specific cells and the cytokine production following M2 peptide stimulation. The pie charts represent the relative ratios of effector and memory CD8+ M2-specific populations in each treatment group.
Figure 8:
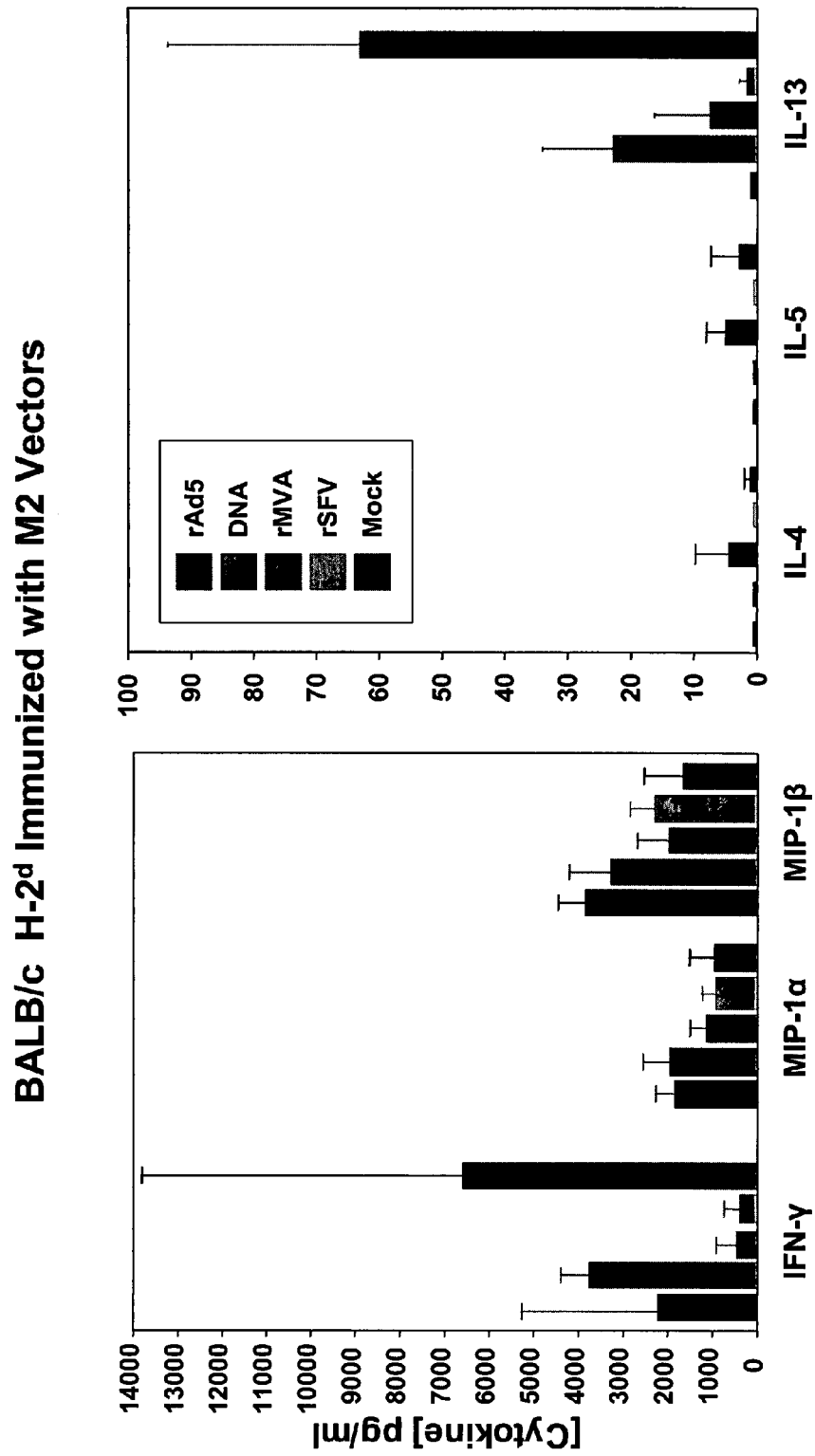
FIG. 8 is two graphs showing cytokine production in the lung on day 5 post RSV challenge. BALB/c H-2d mice were immunized with M2 vectors. Cytokine levels were measured in lung supernatants by ELISA. The inset panel shows the rAd5, DNA, rMVA, rSFV, and Mock vaccine vectors used.
Figure 9A:
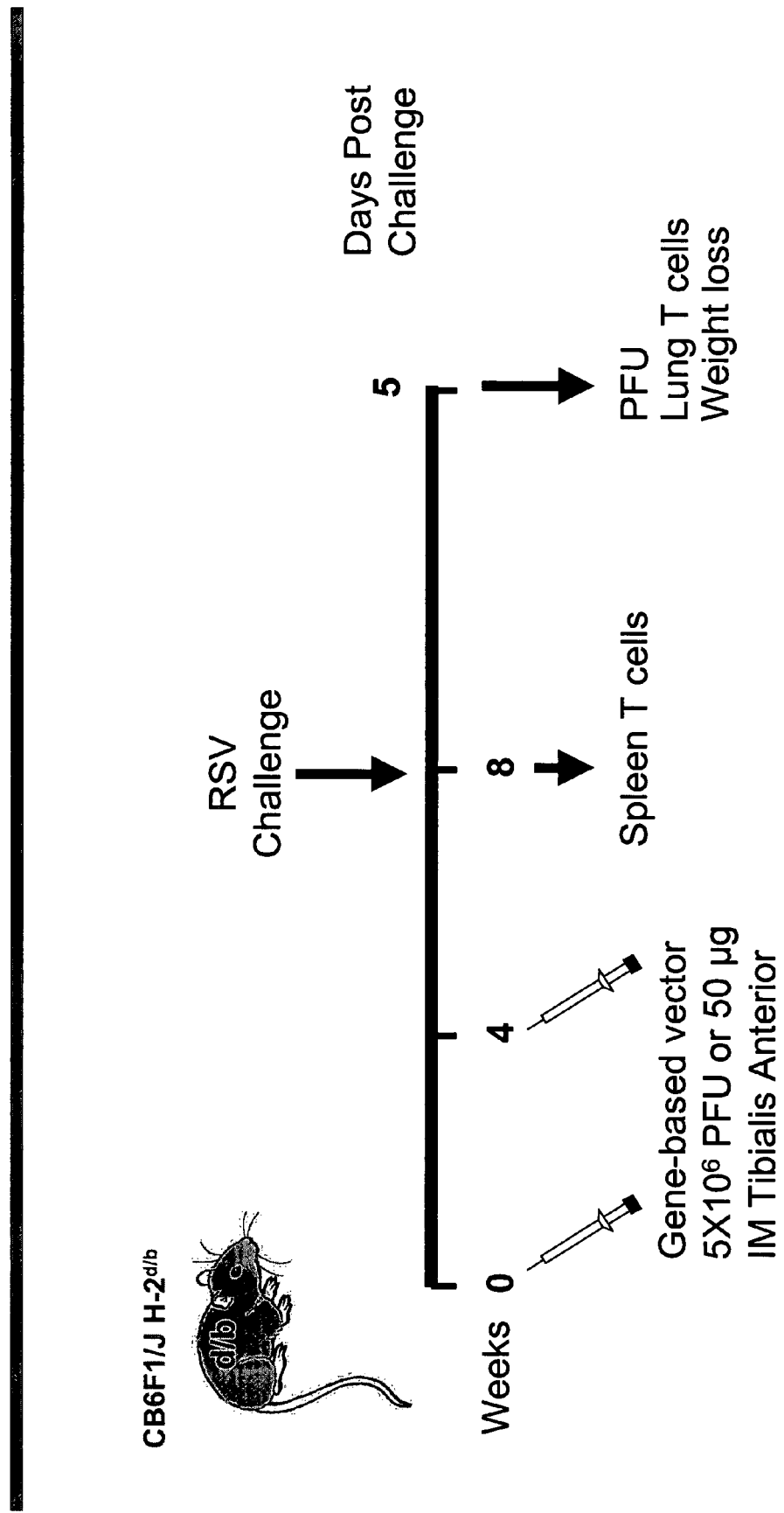
FIG. 9 (a and b) (a) is a schematic detailing the experimental protocol schema. (b) is two graphs that show weight loss and virus replication after RSV challenge. CB6/F1J H-2 d/b mice were immunized with M/M2 vectors. The panel of the left shows the weight loss as a percent of initial weight in grams. rAd5, DNA, rMVA, rSFV, and Mock vaccine vectors were used. The panel on the right shows the virus replication as $Log_{10}$ pfu/gram in the lung after RSV challenge. The same vaccine vectors were used.
Figure 9B:
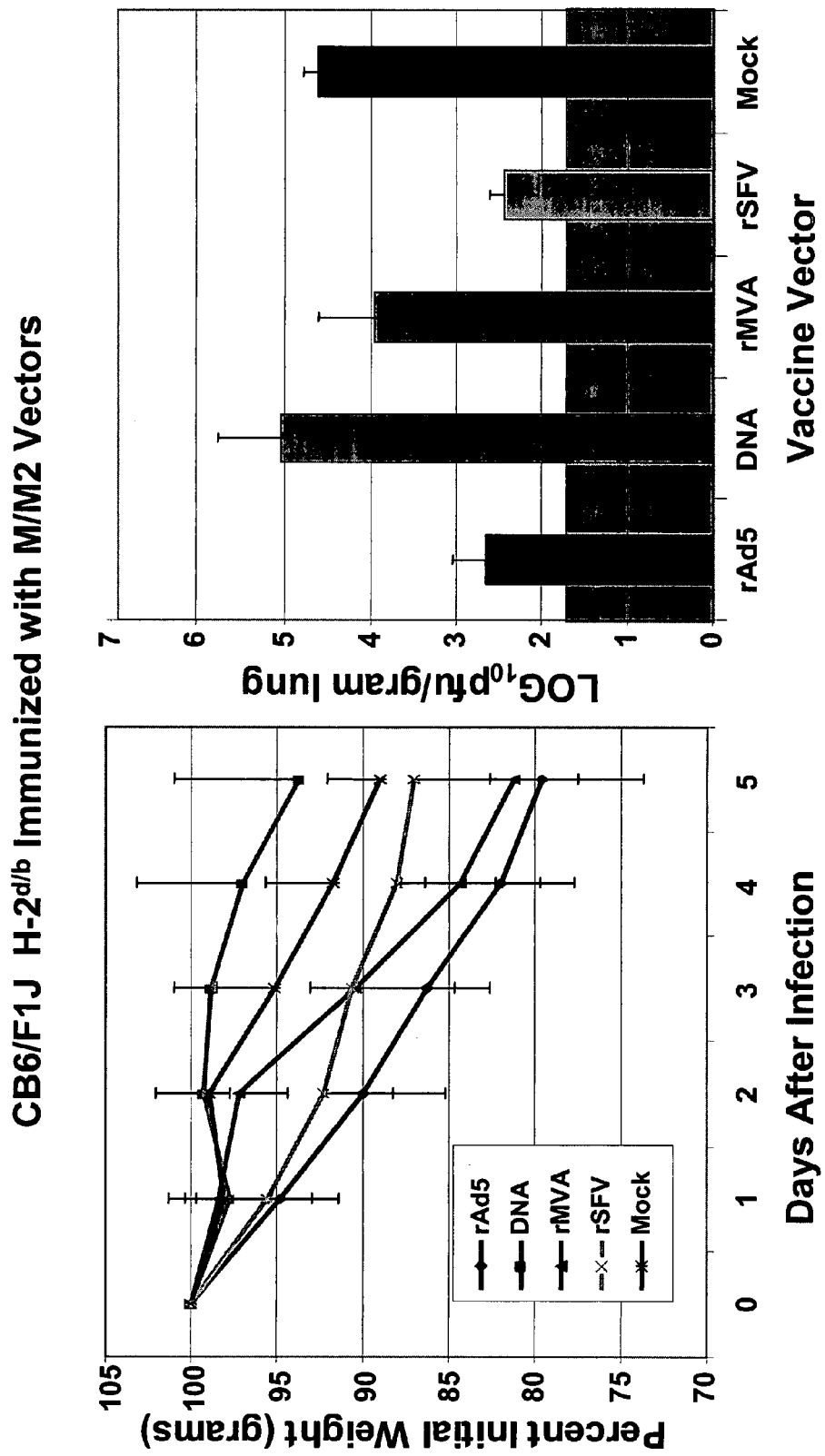
Figure 10:
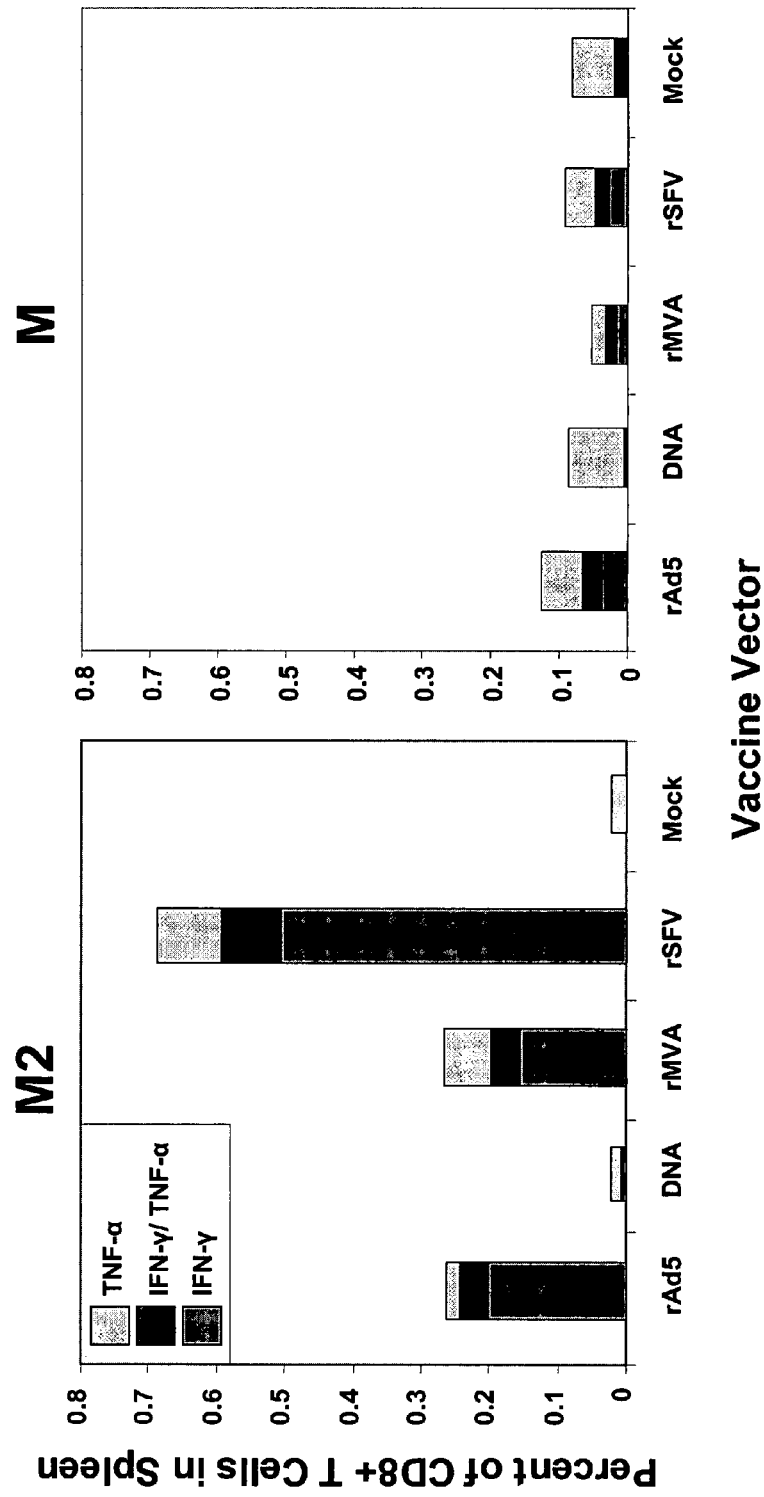
FIG. 10 is two graphs that show M2 or M specific responses in the spleen prior to challenge. CB6/F1J H-$2^{d/b}$ mice were immunized with M/M2 vectors. The graph on the left shows the percent of CD8+ T cells in the spleen prior to challenge, when the M2 was used. The graph on the right shows percent of CD8+ T cells in the spleen prior to challenge, when the M was used. In both cases, RAd5, DNA, rMVA, rSFV, and Mock vaccine vectors were used.
Figure 11:
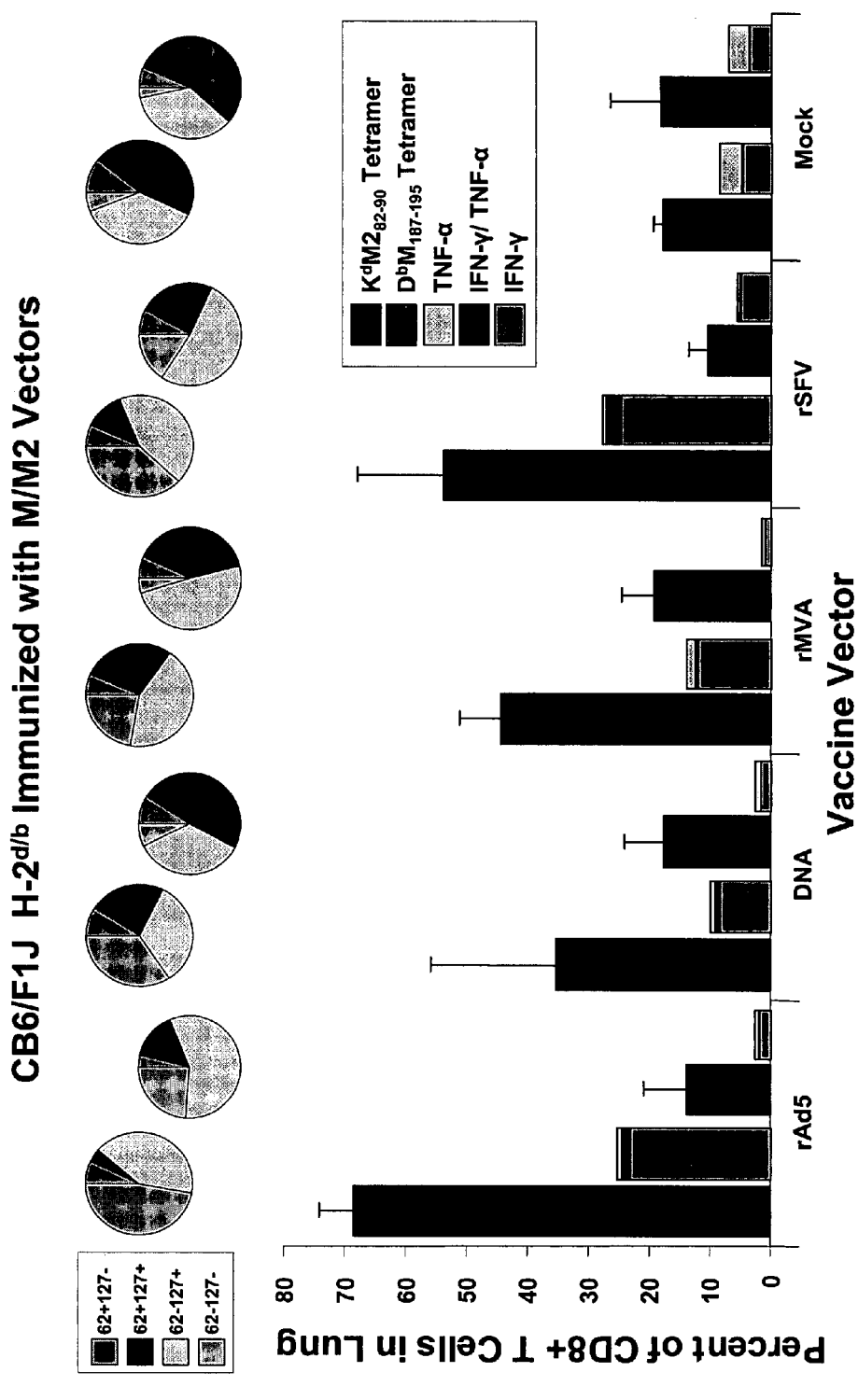
FIG. 11 is a graph that shows the M2 or M specific CD-8+ T cell responses day 5 post RSV challenge. CB6/F1J H-2 d/b mice were immunized with M/M2 vectors. RAd5, DNA, rMVA, rSFV, and Mock vaccine vectors were used. The pie charts represent the relative ratios of effector and memory CD8+M2- or M-specific populations in each treatment group.

A synthetic gene was developed to express a fusion M/M2 protein, and was codon-modified for mammalian expression, as shown in FIG. 4. The fusion gene or individual codon-modified genes for each protein were used to construct experimental vaccine vectors in DNA, replication-defection adenovirus serotype 5 vector (rAd5), modified vaccinia Ankara (rMVA), or a replication-defective Semliki Forest virus vector (rSFV) for subsequent experiments. First, each vaccine vector (DNA, rAd5, rMVA, and rSFV) expressing the M2 protein was compared in BALB/c mice by immunizing twice at 0 and 4 weeks, and then challenging with RSV 4 weeks later. The results are shown in FIG. 5a. T cell responses were analyzed by tetramer staining, staining for CD62 and CD127 to define memory phenotypes, and intracellular cytokine staining (ICS) after peptide stimulation (FIG. 5b). M and M2 are internal proteins and as such do not elicit neutralizing antibody. Thus the focus was on T cell response measurements. Vaccination resulted in reduced virus titer in lungs, but also caused more rapid weight loss following RSV challenge, as shown in FIG. 5c. The weight loss was expected because having a larger T cell response in the absence of neutralizing antibody and challenged with a large virus load will result in immunopathology. It was not expected that the T cell response would reduce virus titer based on prior reports from other groups (Kulkarni A B, Connors M, Firestone C Y, Morse H C 3rd, Murphy B R. The cytolytic activity of pulmonary CD8+ lymphocytes, induced by infection with a vaccinia virus recombinant expressing the M2 protein of respiratory syncytial virus (RSV), correlates with resistance to RSV infection in mice. J. Virol. 1993; 67: 1044-9). The reduction in virus titer correlated with T cell responses measured in the spleen of mice prior to RSV challenge (FIG. 6), and to the post-challenge T cell responses measured in lung (FIG. 7). Importantly, immunization with the gene-based vectors induced responses that did not include Type 2 cytokines (IL-4, IL-5, and IL-13), indicating that the Th2 CD4+ T cell responses associated with the RSV vaccine-enhanced disease, were not induced by this vaccine approach (FIG. 8). Similar results were obtained when the experiment was done in the hybrid mouse using the M/M2 fusion protein expressing vectors, as shown in FIG. 9a. In particular, mice immunized with the rAd5 and rSFV had the greatest reduction in virus titer following RSV challenge (FIG. 9b), which correlated with T cell responses prior to infection in spleen (FIG. 10), and T cell responses post-challenge in lung (FIG. 11). Here, a novel cytolytic assay was employed to ask how well each vector induced CD8+ T cells with the capacity to kill virus-infected target cells (FIG. 12a). The important property of cytolytic activity was greatest in mice immunized with the rAd5 and rSFV vectors and this activity correlated not only with the reduction in virus titer, but with the memory phenotype of the epitope-specific T cells (FIG. 12b, FIG. 13). The rAd5 and rSFV in particular prevented the induction of Type 2 cytokines (FIG. 14).

Figure 15A:
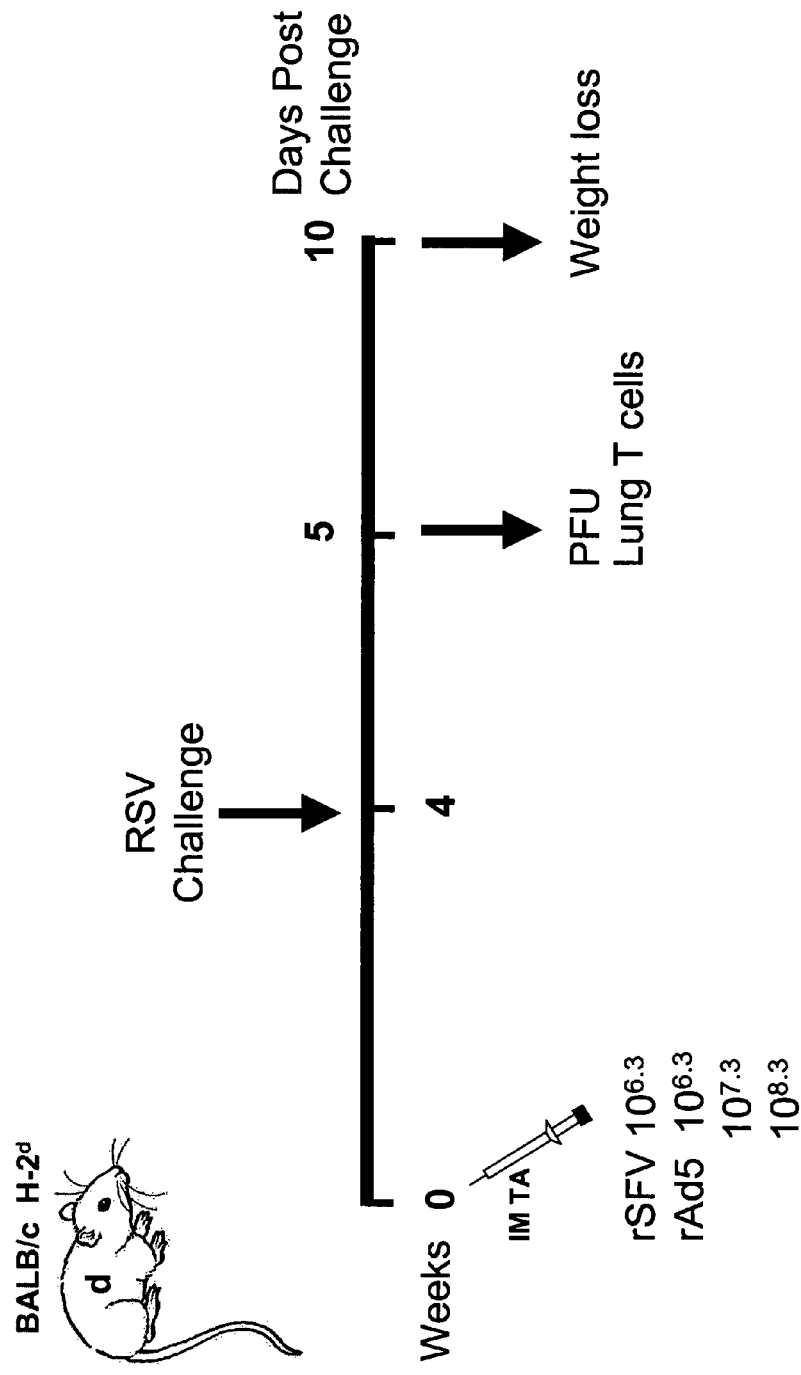
Figure 15B:
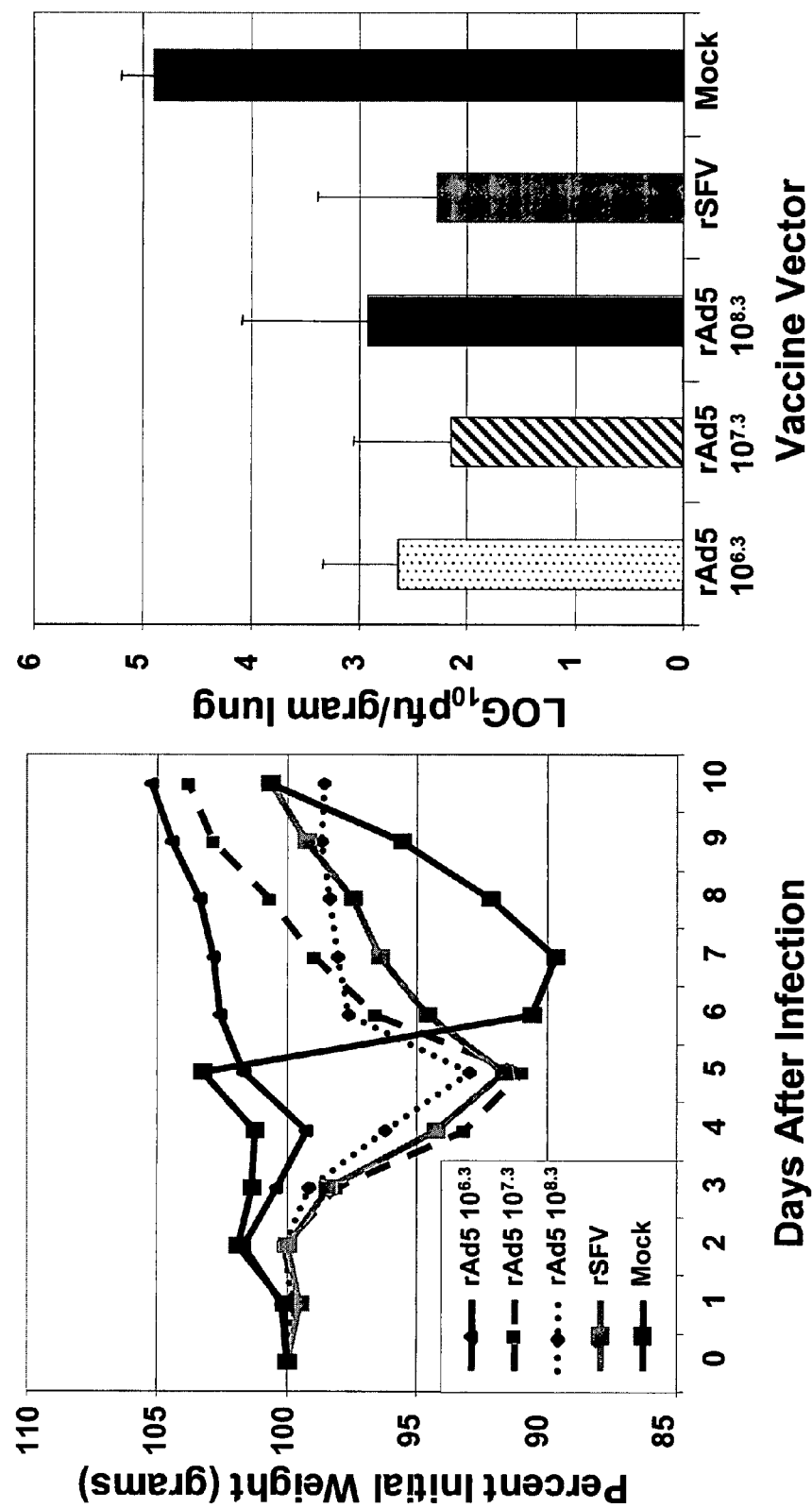

Another experiment was done to evaluate different dosage levels of the rAd5 vector using a single injection of the M2-expressing vectors in BALB/c mice (FIG. 15a). Interestingly, the highest dose of rAd5 expressing the M2 protein not only reduced virus titer, but also prevented illness following RSV challenge, as shown in FIG. 15b. This was not associated with a higher T cell response (FIG. 16), change in the pattern of memory phenotype on days 5 (FIG. 17a) or day 10 (FIG. 17b) after challenge, or with a higher level of cytolytic activity (FIG. 18). There was a trend toward less production of MIP-1 alpha and MIP-1beta (FIG. 19), but a definitive explanation was not found.

Figure 24B:
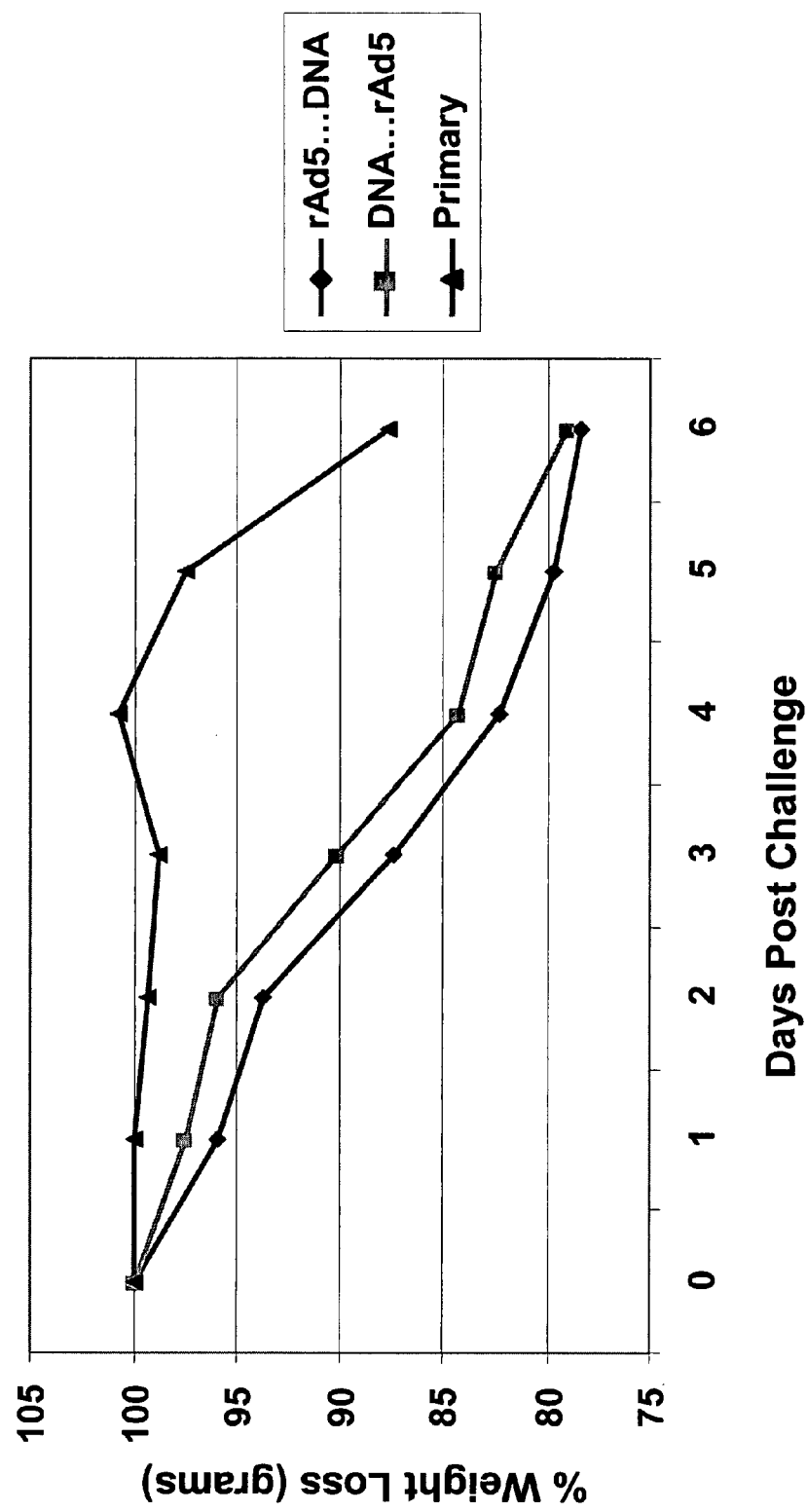
Figure 25A:
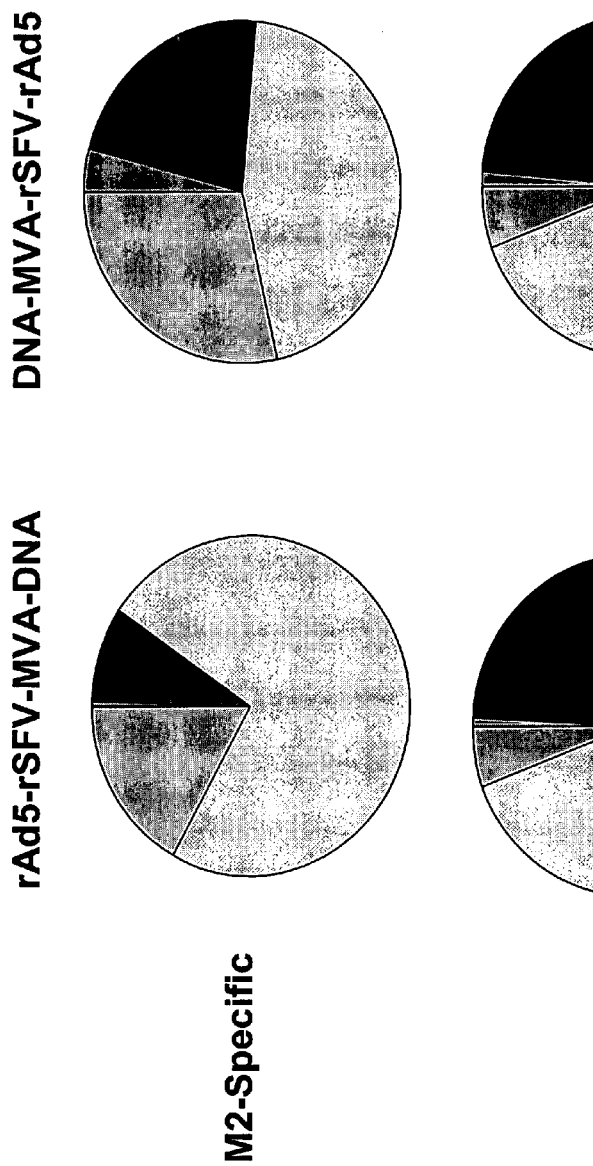
Figure 25B:
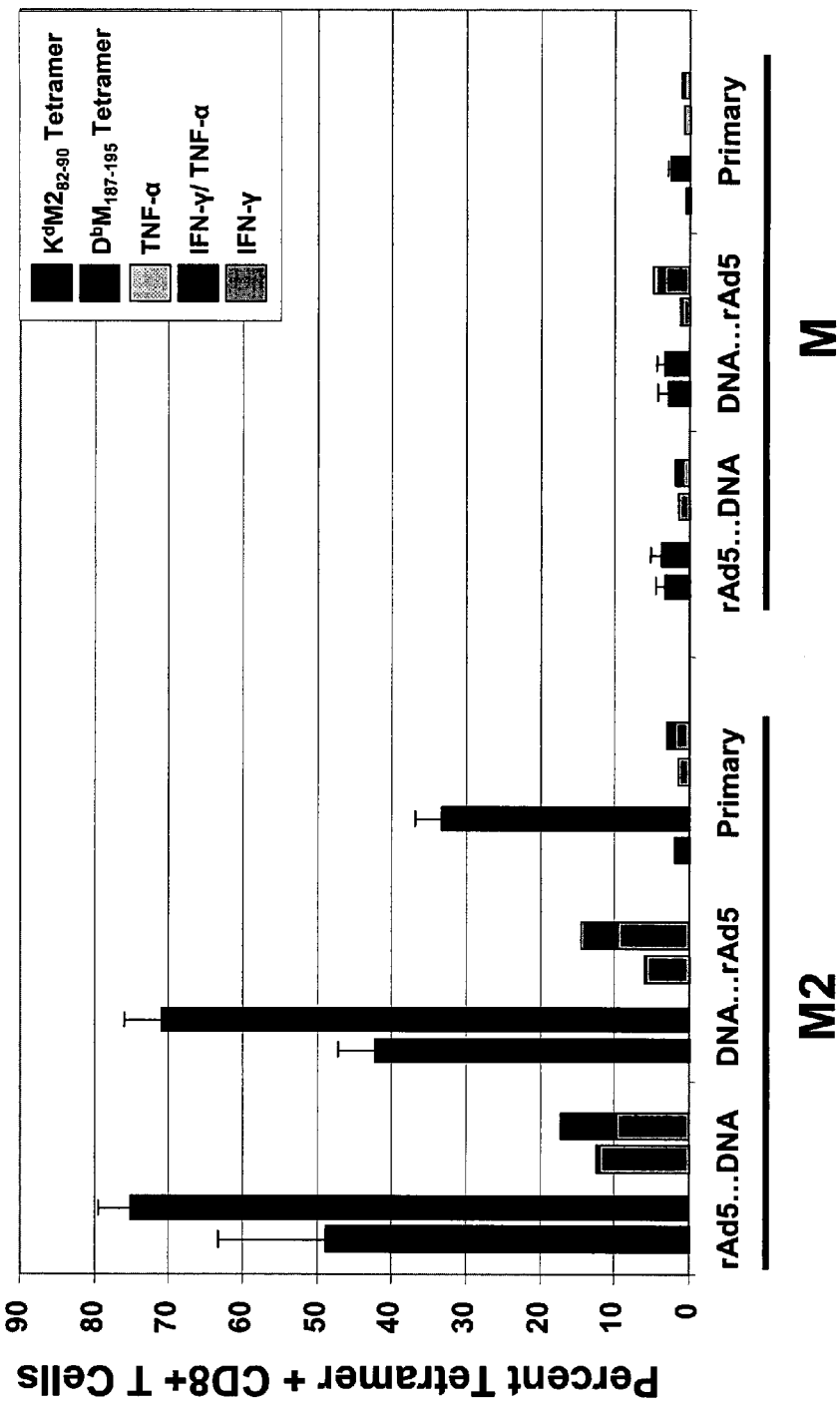
Figure 25C:
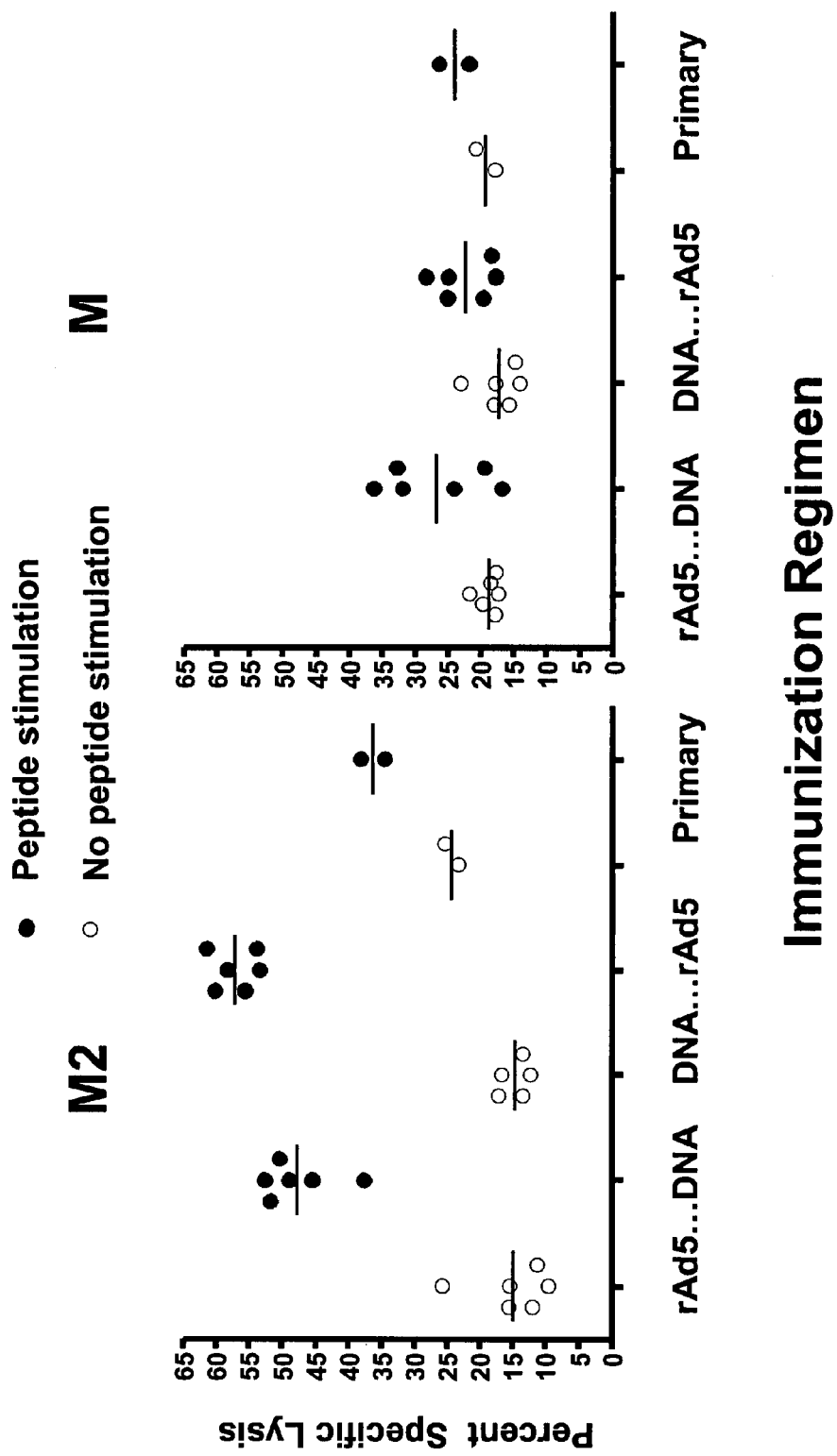
Figure 25D:
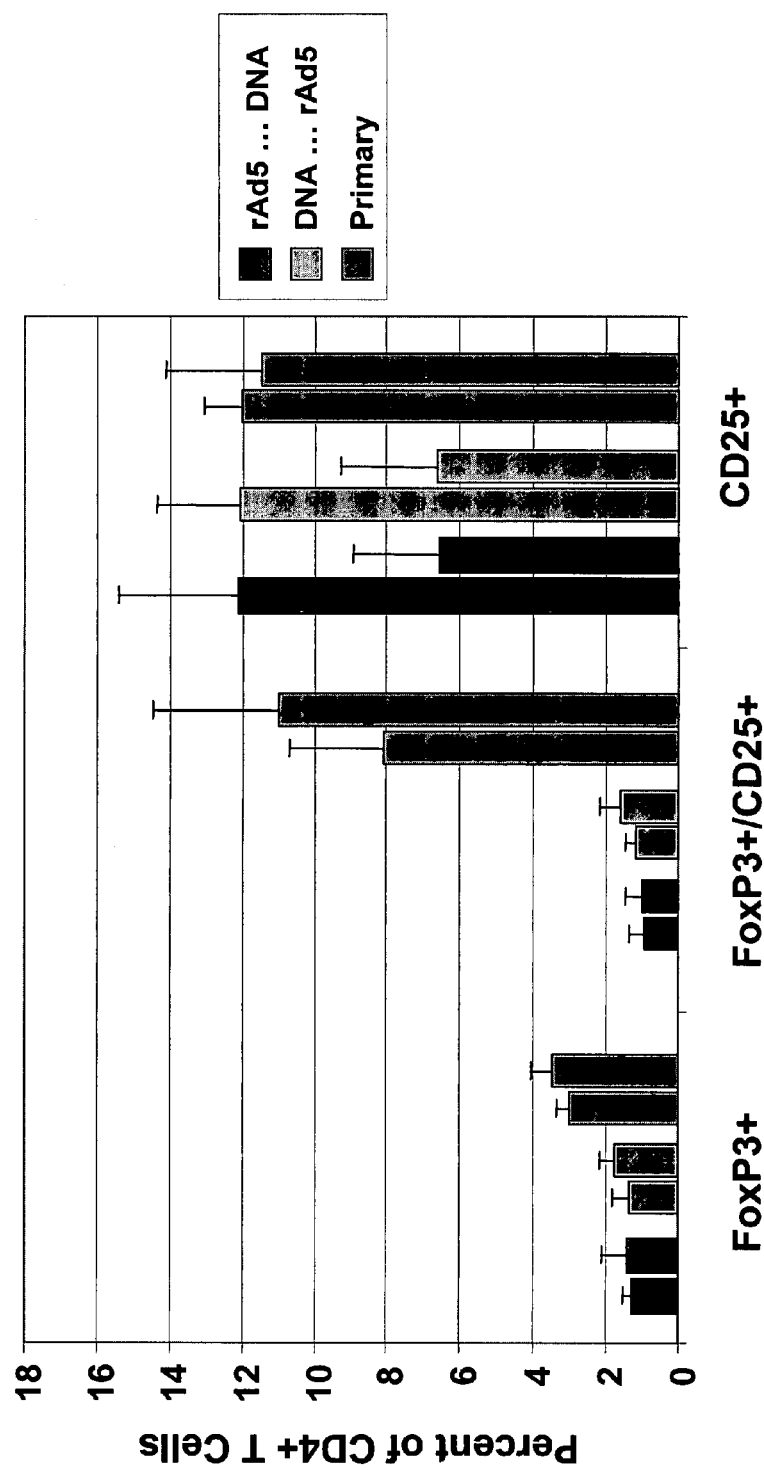
Figure 27A:
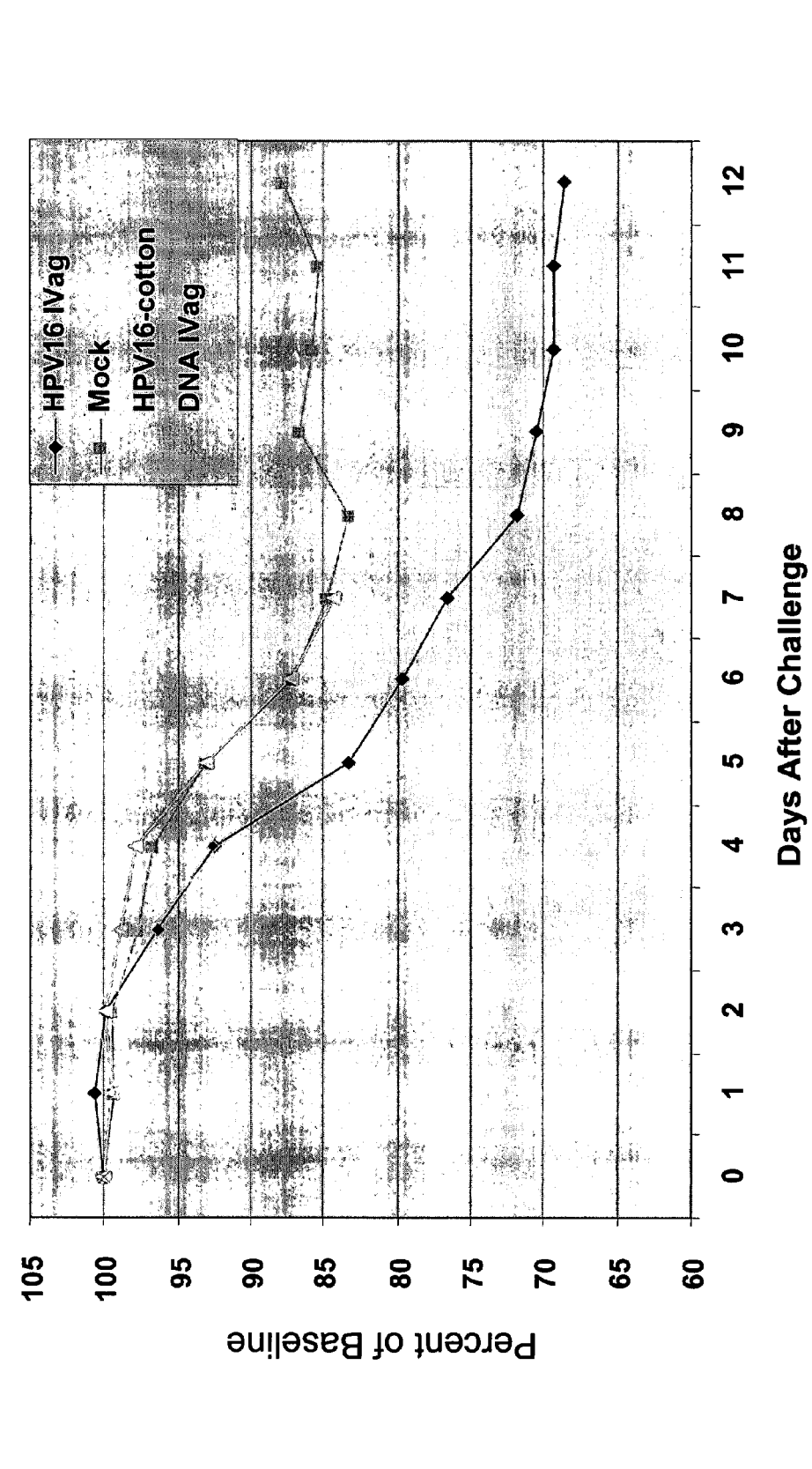
Figure 27B:
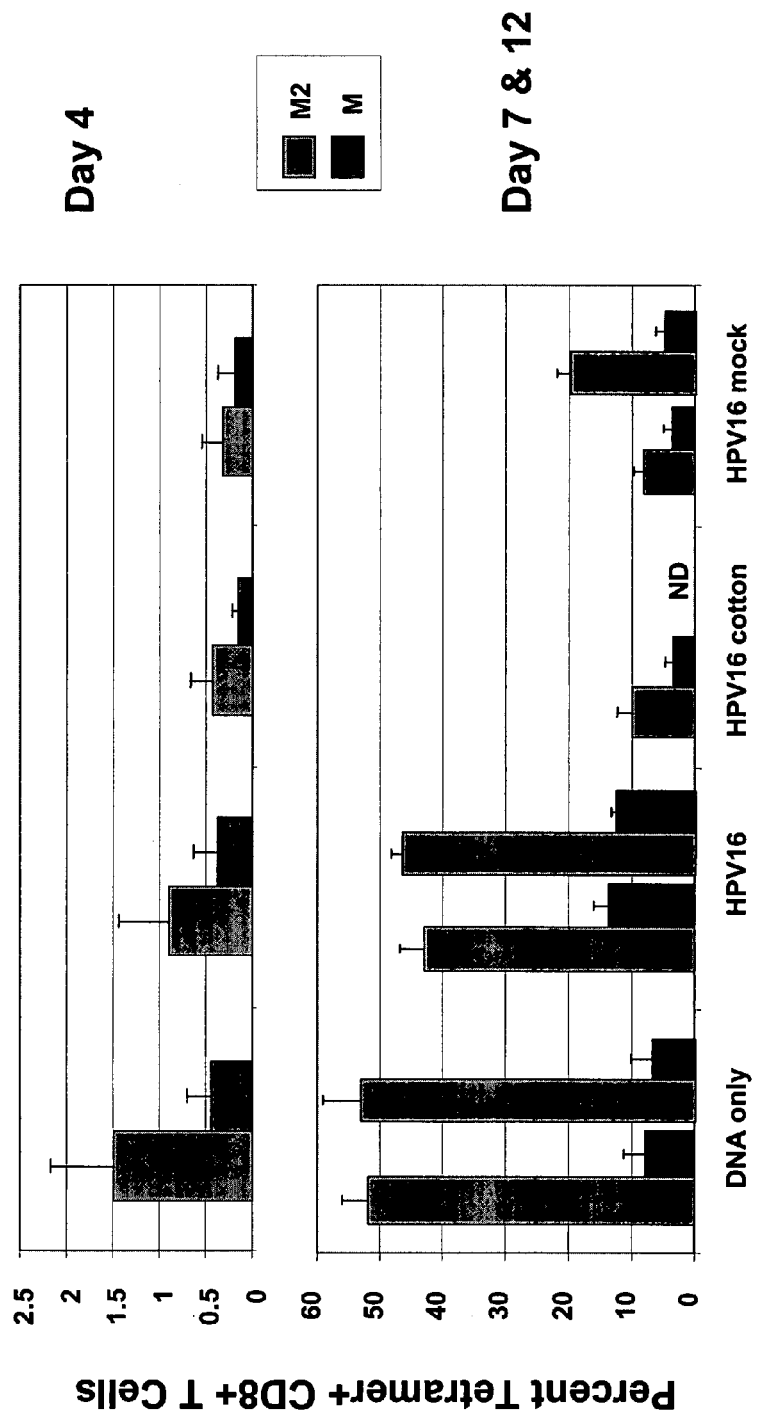

In experiments comparing single or homologous vector boosting as shown in the schema in FIG. 20 and the data in FIG. 21, it was found that heterologous vector prime-boost regimens induce greater antibody responses and more functional T cell responses than giving. This results in greater viral clearance (FIG. 21a) with less immunopathology (FIG. 23). This appears to be related to improved cytolytic function on a per cell basis (FIGS. 22 and 23). The observation that viral clearance with the CD8+ T cell response alone with relatively low immunopathology also occurred with the highest dose level of rAd5 given alone (FIG. 15b). FIG. 24 shows the schema for an experiment evaluating multiple booster injections with heterologous vectors. Both immunization schedules evaluated resulted in a similar level of weight loss following RSV challenge suggesting the T cell responses were similar (FIG. 24b). The phenotypic characteristics of epitope-specific T cells can differ even when induced simultaneously by the same vectors. In this system M2-specific responses are more activated toward effector memory (CD62−CD127+, yellow) while M-specific responses are more characteristic of central memory (CD62+ CD127+, burgundy) T cells (FIG. 25a). Both heterologous vector immunization schedules gave very high levels of tetramer+CD8+ T cell responses in lung post challenge (FIG. 25b) that were associated with high levels of cytolytic activity (FIG. 25c). The highly functional CD8+ T cell response correlated with the reduction in the number of CD4+ T regulatory cells in lung (CD25+FoxP3+) suggesting that immunization with heterologous vectors may drive down Tregs to allow improved effector responses (FIG. 25d). DNA has also been delivered intravaginally either as naked DNA plasmid or packaged in HPV virus-like particles (FIG. 26a) to elicit both M/M2-specific antibody (FIG. 26b) and T cell responses (FIG. 27b) and the intravaginal delivery of naked DNA in particular resulted in diminished weight loss (FIG. 27a). These data suggest that modifications in dose, schedule, delivery route, and vector combinations can all achieve more favorable T cell responses.

In summary, the data presented herein demonstrate that codon-modification of RSV genes allows delivery of gene-based vaccine vectors with excellent potency for inducing CD8+ T cell and antibody responses and avoiding Th2 CD4+ T cell responses. The data presented shows that heterologous vector priming increases T cell cytolytic function. Further, the results show that cytolytic activity per tetramer+CD8+ T cell can correlate with protection from illness. Moreover, the data suggests that this type of approach will be safe with regard to the syndrome of vaccine-enhanced illness associated with the FI-RSV vaccine tested in the 1960's. In addition, the data indicates that a single dose of either the rAd5 or rSFV vector can induce potent and protective immune responses against a high dose challenge. This approach would be immunization of infants prior to 2 months of age feasible and potentially safe. Future experiments that will use structural proteins (F and others) will be able to elicit neutralizing antibodies in addition to the favorable T cell responses that will provide more solid immunity and protection from disease.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An immunogenic composition for eliciting a CD8+ T cell and antibody response comprising a codon-modified gene encoding a Respiratory Syncytial Virus (RSV) F protein, wherein the codon-modified F gene comprises SEQ ID NO: 14, 17, or 18.

2. The immunogenic composition according to claim 1, wherein the codon-modified gene induces an immune response.

3. The immunogenic composition of claim 2, wherein the immune response is a T cell response.

4. The immunogenic composition of claim 1, wherein the codon-modified gene comprises one or more mutations.

5. The immunogenic composition of claim 1, wherein the codon-modified F gene comprises SEQ ID NO: 17 or 18.

6. A kit for use in eliciting an immune response capable of preventing an RSV infection in a subject, the kit comprising:
the immunogenic composition of claim 1; and
a pharmaceutically acceptable carrier.

7. A nucleic acid molecule comprising a codon-modified gene encoding a Respiratory Syncytial Virus (RSV) F protein, wherein said gene comprises SEQ ID NO:14, 17, or 18.

8. A vector comprising a nucleic acid molecule selected from the group consisting of SEQ ID NO: 14, 17, and 18.

9. The vector of claim 8, wherein the nucleic acid molecule is a codon modified sequence that increases expression, optimizes an immunostimulatory signal, or removes a cryptic splice site.

10. The vector of claim 8, wherein the vector is a DNA plasmid.

11. The vector of claim 8, wherein the vector is a replication competent or replication defective vector.

12. The vector of claim 11, wherein the replication competent vector is selected from the group consisting of: parainfluenza virus, Paramyxovirus, Newcastle disease virus, VSV, BCG, vaccinia, reovirus, rhinovirus, poliovirus, and adenovirus.

13. The vector of claim 11, wherein the replication defective vector is selected from the group consisting of: poxviruses, alpha viruses, Venezuelan equine encephalitis viruses (EEV), Sinbis viruses, DNA viruses, adeno associated viruses (AAV), herpes simplex viruses (HSV), adenoviruses, and HPV virus-like particles.

14. A host cell comprising the vector of claim 8.

15. A method of eliciting a CD8+ T cell and antibody response capable of preventing an RSV infection in a subject comprising
administering to the subject the immunogenic composition of claim 1 and a pharmaceutically acceptable carrier.

16. The method of claim 15, wherein the immunogenic composition is administered in a prime boost regimen.

17. The method of claim 16, wherein the prime boost regimen increases T cell cytolytic function.

* * * * *

```
                         SEQUENCE LISTING

<160> NUMBER OF SEQ ID NOS: 20

<210> SEQ ID NO 1
<211> LENGTH: 298
<212> TYPE: PRT
<213> ORGANISM: Human respiratory syncytial virus

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
```

```
                245                 250                 255
Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Pro Pro Asn Thr Pro Arg Gln
    290                 295

<210> SEQ ID NO 2
<211> LENGTH: 896
<212> TYPE: DNA
<213> ORGANISM: Human respiratory syncytial virus

<400> SEQUENCE: 2
atgagcaaga  acaaggacca  gcggaccgcc  aagaccctgg  agagaacctg  ggacaccctg      60
aaccacctgc  tgttcatcag  cagctgcctg  tacaagctga  acctgaagag  cgtggcccag     120 atcccctgt   ctatcctggc  catgatcatc  agcaccagcc  tgatcatcgc  cgccatcatc     180
ttcatcgcca  gcgccaacca  caaagtgacc  cccaccacag  ccatcatcca  ggacgccacc     240
tcccagatca  agaacaccac  ccccacctac  ctgacccaga  ccctcagct   gggcatcagc     300 cctagcaacc  ccagcgagat  cacctctcag  atcaccacca  tcctggcctc  taccacccct     360
ggcgtgaagt  ctaccctgca  gagcaccacc  gtcaagacca  agaacacgac  caccacacag     420
acccagccta  gcaagcctac  caccaagcag  aggcagaaca  agcctcccag  caagcccaac     480
aacgacttcc  actttgaagt  gttcaacttc  gtgccctgca  gcatctgcag  caacaaccct     540
acctgctggg  ccatctgcaa  gcgcatcccc  aacaagaagc  ccggcaagaa  accaccacc      600 aagcccacca  gaagcctac   cctcaagacc  accaagaagg  accccaagcc  ccagaccaca     660
aagagcaagg  aagtgcccac  aaccaagcct  accgaggagc  ccaccatcaa  cacgaccaag     720
accaacatca  tcaccaccct  gctgacctct  aacaccaccg  caacccgta   gctgaccagc     780 cagatggaga  ccttccacag  cacctctagc  gagggcaacc  ctagccctag  ccaagtgagc     840
accacctctg  agtaccctag  ccagcccagc  tctcctccta  ataccctcg   gcagtg         896

<210> SEQ ID NO 3
<211> LENGTH: 256
<212> TYPE: PRT
<213> ORGANISM: Human respiratory syncytial virus

<400> SEQUENCE: 3

Met Glu Thr Tyr Val Asn Lys Leu His Glu Gly Ser Tyr Thr Ala
1               5                   10                  15

Ala Val Gln Tyr Asn Val Leu Glu Lys Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Lys Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
```

-continued

```
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 4
<211> LENGTH: 768
<212> TYPE: DNA
<213> ORGANISM: Human respiratory syncytial virus

<400> SEQUENCE: 4
atggagacct acgtgaataa gctgcacgag ggaagcacct acaccgccgc tgtgcagtac      60
aatgtgctgg agaaggacga tgatcctgct tccctgacca tctgggtgcc catgtttcag     120
tctagcatgc ccgccgatct gctgattaag gagctggcca acgtgaacat cctggtgaag     180
cagatcagca ccccaaaggg accttccctg agagtgatga ttaactccag aagcgccgtg     240
ctggcccaga tgccctctaa gttcacaatc tgcgctaatg tgtccctgga cgagagatcc     300
aagctggctt acgatgtgac caccccatgc gagatcaagg cttgttctct gacctgtctg     360
aagtccaaga atatgctgac caccgtgaag gacctgacaa tgaaaacact gaatcccacc     420
cacgatatca tcgccctgtg tgagtttgag aatatcgtga caagcaagaa ggtcatcatc     480
ccaacatacc tgagatctat ctctgtgagg aataaggatc tgaacacact ggagaatatc     540
acaaccaccg agtttaagaa cgctatcaca aacgccaaga tcatccctta cagcggactg     600
ctgctggtca tcacagtgac cgataacaag ggcgccttca agtacatcaa gccacagtcc     660
cagttcatcg tggatctggg cgcttacctg gagaaggaga gcatctacta cgtgaccacc     720
aactggaagc acacagctac aagattcgcc atcaagccca tggaggac                  768

<210> SEQ ID NO 5
<211> LENGTH: 194
<212> TYPE: PRT
<213> ORGANISM: Human respiratory syncytial virus

<400> SEQUENCE: 5

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60
```

```
Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Val Ser Asp Thr Asn Asp His Ala Lys Asn Asn Asp
            180                 185                 190

Thr Thr

<210> SEQ ID NO 6
<211> LENGTH: 578
<212> TYPE: DNA
<213> ORGANISM: Human respiratory syncytial virus

<400> SEQUENCE: 6
atgagccggc ggaatccatg taagttcgag atcagaggcc actgcctgaa tggaaagaga     60
tgccacttca gccacaacta cttcgagtgg cccccacacg ctctgctggt gagacagaat    120
ttcatgctga accgcatcct gaagagcatg gataagagca tcgacacact gagcgagatc    180
tctggcgctg ccgagctgga tcggacagag gagtacgccc tgggagtggt gggagtgctg    240
gagagctaca tcggctccat caataacatc accaagcaga gcgcctgcgt ggctatgagc    300
aagctgctga ccgagctgaa tagcgatgac atcaagaagc tgagagacaa cgaggagctg    360
aacagcccaa agatcagagt gtacaataca gtgatctctt acatcgagag caataggaag    420
aacaacaagc agaccatcca cctgctgaag agactgcccg ctgatgtgct gaagaaaacc    480
atcaagaata cactggacat ccacaagtct atcacaatca acaatcctaa ggagagcaca    540
gtgagcgata caaacgacca cgctaagaat aatgatac                            578

<210> SEQ ID NO 7
<211> LENGTH: 901
<212> TYPE: DNA
<213> ORGANISM: Human respiratory syncytial virus

<400> SEQUENCE: 7
atgagcaaga acaaggacca gcggaccgcc aagaccctgg agagaacctg ggacaccctg     60
aaccacctgc tgttcatcag cagctgcctg tacaagctga acctgaagag cgtggcccag    120
atcaccctgt ctatcctggc catcatcatc agcaccagcc tgatcatcgc cgccatcatc    180
ttcatcgcca gcgccaacca caaagtgacc cccaccacag ccatcatcca ggacgccacc    240
tcccagatca agaacaccac ccccacctac ctgacccaga accctcagct gggcatcagc    300
cctagcaacc ccagcgagat cacctctcag atcaccacca tcctggcctc taccacccct    360
ggcgtgaagt ctaccctgca gagcaccacc gtcaagacca agaacacgac caccacacag    420
acccagccta gcaagcctac caccaagcag aggcagaaca agcctcccag caagcccaac    480
```

```
aacgacttcc actttgaagt gttcaacttc gtgccctgca gcatctgcag caacaaccct      540
acctgctggg ccatctgcaa gcgcatcccc aacaagaagc ccggcaagaa accaccacc      600 aagcccacca agaagcctac cctcaagacc accaagaagg accccaagcc ccagaccaca      660
aagagcaagg aagtgcccac aaccaagcct accgaggagc caccatcaa cacgaccaag       720 accaacatca tcaccaccct gctgacctct aacaccaccg caaccctga gctgaccagc       780 cagatggaga ccttccacag cacctctagc gagggcaacc ctagccctag ccaagtgagc      840
accacctctg agtaccctag ccagcccagc tctcctccta taccccctcg gcagtgagga      900
t                                                                     901
```

```
<210> SEQ ID NO 8
<211> LENGTH: 1360
<212> TYPE: DNA
<213> ORGANISM: Human respiratory syncytial virus

<400> SEQUENCE: 8
atggagacct acgtgaataa gctgcacgag ggaagcacct acaccgccgc tgtgcagtac       60
aatgtgctgg agaaggacga tgatcctgct tccctgacca tctgggtgcc catgtttcag      120
tctagcatgc ccgccgatct gctgattaag gagctggcca acgtgaacat cctggtgaag      180
cagatcagca ccccaaaggg accttccctg agagtgatga ttaactccag aagcgccgtg      240
ctggcccaga tgccctctaa gttcacaatc tgcgctaatg tgtccctgga cgagagatcc      300
aagctggctt acgatgtgac caccccatgc gagatcaagg cttgttctct gacctgtctg      360
aagtccaaga atatgctgac caccgtgaag gacctgacaa tgaaaacact gaatcccacc      420
cacgatatca tcgccctgtg tgagtttgag aatatcgtga caagcaagaa ggtcatcatc      480
ccaacatacc tgagatctat ctctgtgagg aataaggatc tgaacacact ggagaatatc      540
acaaccaccg agtttaagaa cgctatcaca aacgccaaga tcatccctta cagcggactg      600
ctgctggtca tcacagtgac cgataacaag ggcgccttca gtacatcaa gccacagtcc       660 cagttcatcg tggatctggg cgcttacctg gagaaggaga gcatctacta cgtgaccacc      720
aactggaagc acacagctac aagattcgcc atcaagccca tggaggaccc tgatcaggct      780
atgtctaggc gcaacccttg caagtttgag atccggggac actgtctgaa cggcaagcgg      840
tgtcactttt ctcacaatta ctttgagtgg cctcctcacg ccctgctggt gcggcagaac      900
tttatgctga atagaatcct gaagtctatg gacaagtcta tcgataccct gtccgagatc      960
tccggagccg ctgagctgga cagaaccgag gagtacgctc tgggcgtggt gggcgtgctg     1020
gagtcttaca tcggcagcat caacaatatc acaaagcagt ccgcttgtgt ggccatgtct     1080
aagctgctga cagagctgaa ctctgacgat atcaagaagc tgcgggataa cgaggagctg     1140
aattccccta agatccgcgt gtacaacacc gtgatctcct acatcgagtc caaccgcaag     1200
aataataagc agacaatcca cctgctgaag cggctgcctg ccgacgtgct gaagaaaaca     1260
atcaagaaca ccctggatat ccacaagagc atcaccatca ataccccaa ggagtctacc      1320 gtgtccgaca caaacgatca cgccaagaac aacgacacaa                           1360
```

```
<210> SEQ ID NO 9
<211> LENGTH: 391
<212> TYPE: PRT
<213> ORGANISM: Human respiratory syncytial virus

<400> SEQUENCE: 9

Met Ala Leu Ser Lys Val Lys Leu Asn Asp Thr Leu Asn Lys Asp Gln
```

```
                1               5                   10                  15
        Leu Leu Ser Ser Ser Lys Tyr Thr Ile Gln Arg Ser Thr Gly Asp Ser
                        20                  25                  30

Ile Asp Thr Pro Asn Tyr Asp Val Gln Lys His Ile Asn Lys Leu Cys
                        35                  40                  45

Gly Met Leu Leu Ile Thr Glu Asp Ala Asn His Lys Phe Thr Gly Leu
                        50                  55                  60

Ile Gly Met Leu Tyr Ala Met Ser Arg Leu Gly Arg Glu Asp Thr Ile
         65                 70                  75                  80

Lys Ile Leu Arg Asp Ala Gly Tyr His Val Lys Ala Asn Gly Val Asp
                        85                  90                  95

Val Thr Thr His Arg Gln Asp Ile Asn Gly Lys Glu Met Lys Phe Glu
                        100                 105                 110

Val Leu Thr Leu Ala Ser Leu Thr Thr Glu Ile Gln Ile Asn Ile Glu
                        115                 120                 125

Ile Glu Ser Arg Lys Ser Tyr Lys Lys Met Leu Lys Glu Met Gly Glu
                        130                 135                 140

Val Ala Pro Glu Tyr Arg His Asp Ser Pro Asp Cys Gly Met Ile Ile
        145                 150                 155                 160

Leu Cys Ile Ala Ala Leu Val Ile Thr Lys Leu Ala Ala Gly Asp Arg
                        165                 170                 175

Ser Gly Leu Thr Ala Val Ile Arg Arg Ala Asn Asn Val Leu Lys Asn
                        180                 185                 190

Glu Met Lys Arg Tyr Lys Gly Leu Leu Pro Lys Asp Ile Ala Asn Ser
                        195                 200                 205

Phe Tyr Glu Val Phe Glu Lys His Pro His Phe Ile Asp Val Phe Val
                        210                 215                 220

His Phe Gly Ile Ala Gln Ser Ser Thr Arg Gly Gly Ser Arg Val Glu
        225                 230                 235                 240

Gly Ile Phe Ala Gly Leu Phe Met Asn Ala Tyr Gly Ala Gly Gln Val
                        245                 250                 255

Met Leu Arg Trp Gly Val Leu Ala Lys Ser Val Lys Asn Ile Met Leu
                        260                 265                 270

Gly His Ala Ser Val Gln Ala Glu Met Glu Gln Val Val Glu Val Tyr
                        275                 280                 285

Glu Tyr Ala Gln Lys Leu Gly Gly Glu Ala Gly Phe Tyr His Ile Leu
                        290                 295                 300

Asn Asn Pro Lys Ala Ser Leu Leu Ser Leu Thr Gln Phe Pro His Phe
        305                 310                 315                 320

Ser Ser Val Val Leu Gly Asn Ala Ala Gly Leu Gly Ile Met Gly Glu
                        325                 330                 335

Tyr Arg Gly Thr Pro Arg Asn Gln Asp Leu Tyr Asp Ala Ala Lys Ala
                        340                 345                 350

Tyr Ala Glu Gln Leu Lys Glu Asn Gly Val Ile Asn Tyr Ser Val Leu
                        355                 360                 365

Asp Leu Thr Ala Glu Glu Leu Glu Ala Ile Lys His Gln Leu Asn Pro
                        370                 375                 380

Lys Asp Asn Asp Val Glu Leu
        385                 390

<210> SEQ ID NO 10
        <211> LENGTH: 1191
        <212> TYPE: DNA
        <213> ORGANISM: Human respiratory syncytial virus
```

<400> SEQUENCE: 10

```
atggccctga gcaaggtcaa gctgaacgac accctgaaca aggaccagct gctgtccagc     60
agcaagtaca ccatccagag aagcaccggc gacagcatcg acacccccaa ctacgacgtg    120
cagaagcaca tcaacaagct gtgcggcatg ctgctgatca ccgaggacgc caaccacaag    180
ttcaccggcc tgatcggcat gctgtacgcc atgagcaggc tgggcagaga ggacaccatc    240
aagatcctga gggacgccgg ctaccacgtg aaggccaacg gcgtggacgt gaccacccac    300
aggcaggaca tcaacggcaa ggagaacaag ttcgaggtcc tgaccctggc cagcctgacc    360
accgagatcc agatcaacat cgagatcgag tctaggaaga gctacaagaa gatgctgaag    420
gagatgggcg aggtcgcccc cgagtacagg cacgacagcc ccgactgcgg catgatcatc    480
ctgtgcatcg ccgccctggt catcaccaag ctggctgccg gcgacagaag cggcctgacc    540
gccgtcatca gacgggccaa caacgtgctg aagaacgaga tgaagaggta caagggcctg    600
ctgcccaagg acatcgccaa cagcttctac gaggtgttcg agaagcaccc ccacttcatc    660
gacgtgttcg tgcacttcgg catcgcccag agcagcacca ggggcggcag cagggtggag    720
ggcatcttcg ccggcctgtt catgaacgcc tacggagccg gccaggtcat gctgagatgg    780
ggcgtgctgg ccaagagcgt gaagaacatc atgctgggcc acgccagcgt gcaggccgag    840
atggaacagg tggtggaggt gtacgagtac gcccagaagc tgggcggcga ggccggcaga    900
taccacatcc tgaacaaccc caaggcctcc ctgctgtccc tgacccagtt cccccacttc    960
tccagcgtgg tgctgggcaa tgccgccgga ctgggcatca tgggcgagta cagaggcacc   1020
cccaggaacc aggacctgta cgacgccgcc aaggcctacg ccgagcagct gaaggagaac   1080
ggcgtcatca actacagcgt gctggatctg accgccgagg aactggaagc catcaagcac   1140
cagctgaacc ccaaggacaa cgacgtggag ctgtgatgag gatccgagct c            1191
```

<210> SEQ ID NO 11
<211> LENGTH: 64
<212> TYPE: PRT
<213> ORGANISM: Human respiratory syncytial virus

<400> SEQUENCE: 11

```
Met Glu Asn Thr Ser Ile Thr Ile Glu Phe Ser Ser Lys Phe Trp Pro
1               5                   10                  15

Tyr Phe Thr Leu Ile His Met Ile Thr Thr Ile Ile Ser Leu Leu Ile
            20                  25                  30

Ile Ile Ser Ile Met Ile Ala Ile Leu Asn Lys Leu Cys Glu Tyr Asn
        35                  40                  45

Val Phe His Asn Lys Thr Phe Glu Leu Pro Arg Ala Arg Val Asn Thr
    50                  55                  60
```

<210> SEQ ID NO 12
<211> LENGTH: 193
<212> TYPE: DNA
<213> ORGANISM: Human respiratory syncytial virus

<400> SEQUENCE: 12

```
atggaaaaca ccagcatcac catcgagttc agcagcaagt tctggcccta cttcaccctg     60
atccacatga tcaccaccat catcagcctg ctgatcatca tcagcatcat gatcgccatc    120
ctgaacaagc tgtgcgagta caacgtgttc cacaacaaga ccttcgagct gcccagggcc    180
agggtgaaca cct                                                       193
```

<210> SEQ ID NO 13
<211> LENGTH: 574
<212> TYPE: PRT
<213> ORGANISM: Human respiratory syncytial virus

<400> SEQUENCE: 13

| Met | Glu | Leu | Leu | Ile | Leu | Lys | Ala | Asn | Ala | Ile | Thr | Thr | Ile | Leu | Thr |
|---|---|---|---|---|---|---|---|---|---|---|---|---|---|---|---|
| 1 | | | | 5 | | | | | 10 | | | | | 15 | |

Ala Val Thr Phe Cys Phe Ala Ser Gly Gln Asn Ile Thr Glu Glu Phe
        20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Met Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 14
<211> LENGTH: 1735
<212> TYPE: DNA
<213> ORGANISM: Human respiratory syncytial virus

<400> SEQUENCE: 14

```
atggagctgc tgatcctgaa ggccaacgcc atcaccacca tcctgaccgc cgtgaccttc      60
tgcttcgcca gcggccagaa tatcaccgag gagttctacc agagcacctg tagcgccgtg     120
tccaagggct acctgagcgc cctgagaacc ggctggtaca ccagcgtgat caccatcgag     180
ctgtccaaca tcaaggaaaa caagtgtaac ggcaccgacg ccaaggtgaa gctgatcaag     240
caggagctgg acaagtacaa gaacgccgtg accgagctgc agctgctgat gcagagcacc     300
ccccccacca acaacagagc caggcgcgag ctgccccggt tcatgaacta cacccctgaac    360 aacgccaaga aaaccaacgt gaccctgagc aagaagcgga gcggagatt cctgggcttc     420 ctgctgggag tgggcagcgc catcgccagc ggagtggccg tgtctaaggt gctgcacctg     480
gagggcgagt gaacaagat caagagcgcc ctgctgtcca ccaacaaggc cgtggtgtcc      540
ctgagcaacg gcgtgtccgt gctgaccagc aaggtgctgg atctgaagaa ctacatcgac     600
aagcagctgc tgcccatcgt gaacaagcag agctgctcca tcagcaacat cgagaccgtg     660
atcgagttcc agcagaagaa caaccggctg ctggagatca ccagggagtt cagcgtgaac     720
gccggcgtga ccacccctgt gagcacctac atgctgacca cagcgagct gctgtccctg      780 atcaatgaca tgcccatcac caacgaccag aaaaagctga tgagcaacaa cgtgcagatt     840
gtgaggcagc agagctacag catcatgagc atcatcaagg aagaggtgct ggcctacgtg     900
gtgcagctgc ccgtgacggg cgtgatcgat ccccttgct ggaagctgca caccagccct      960
ctgtgtacca ccaacaccaa ggagggcagc aacatctgcc tgaccaggac cgatagaggc    1020
```

```
tggtactgtg acaatgccgg cagcgtgtcc ttcttccccc aggccgagac ctgtaaggtg      1080
cagagcaacc gggtgttctg tgacaccatg aacagcctga ccctgcccag cgagatcaac      1140
ctgtgtaacg tggacatctt caaccccaag tacgactgta agatcatgac ctccaagacc      1200
gacgtgtcca gcagcgtgat taccagcctg ggcgccatcg tgtcctgcta cggcaagacc      1260
aagtgtaccg ccagcaacaa gaaccggggg atcatcaaga ccttcagcaa cggctgtgac      1320
tacgtgtcaa aagggcatg  gacaccgtgt ctgtgggcaa cacactgtac acgtgaata      1380 agcaggaggg caagagcctg tacgtgaagg gcgagcccat catcaacttc tacgaccccc      1440
tggtgttccc tagcgacgag ttcgatgcca gcatcagcca ggtgaacgag aagatcaacc      1500
agagcctggc cttcatcagg aagagcgacg agctgctgca caatgtgaat gccggcaaga      1560
gcaccaccaa catcatgatc accacaatca tcatcgtgat cattgtgatc ctgctgtctc      1620
tgattgctgt gggcctgctg ctgtactgta aggccagatc caccccgtg  accctgtcca      1680 aggaccagct gtccggcatc aacaacatcg ccttctccaa ctgatgagga tccag           1735

<210> SEQ ID NO 15
<211> LENGTH: 298
<212> TYPE: PRT
<213> ORGANISM: Human respiratory syncytial virus

<400> SEQUENCE: 15

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Ile Ile Ser Thr Ser Leu Ile Ile Ala Ala Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Pro Gly Val Lys Ser Thr Leu Gln Ser
        115                 120                 125

Thr Thr Val Lys Thr Lys Asn Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255
```

Glu Leu Thr Ser Gln Met Glu Thr Phe His Ser Thr Ser Glu Gly
            260                 265                 270

Asn Pro Ser Pro Ser Gln Val Ser Thr Thr Ser Glu Tyr Pro Ser Gln
            275                 280                 285

Pro Ser Ser Pro Pro Asn Thr Pro Arg Gln
            290                 295

<210> SEQ ID NO 16
<211> LENGTH: 574
<212> TYPE: PRT
<213> ORGANISM: Human respiratory syncytial virus

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg

```
                    325                 330                 335
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 17
<211> LENGTH: 1758
<212> TYPE: DNA
<213> ORGANISM: Human respiratory syncytial virus

<400> SEQUENCE: 17
ggtaccgtcg acgccaccat ggagctgctg atcctgaagg ccaacgccat caccaccatc      60
ctgaccgccg tgaccttctg cttcgccagc ggccagaata tcaccgagga gttctaccag     120
agcacctgta gcgccgtgtc aagggctac ctgagcgccc tgagaaccgg ctggtacacc      180
agcgtgatca ccatcgagct gtccaacatc aaggaaaaca gtgtaacgg caccgacgcc      240 aaggtgaagc tgatcaagca ggagctggac aagtacaaga cgccgtgac cgagctgcag      300 ctgctgatgc agagcacccc cgccaccaac aacagagcca ggcgcgagct gccccggttc     360
atgaactaca ccctgaacaa cgccaagaaa accaacgtga ccctgagcaa gagcggaag      420 cggagattcc tgggcttcct gctgggagtg ggcagcgcca tcgccagcgg agtggccgtg     480
tctaaggtgc tgcacctgga gggcgaggtg aacaagatca gagcgccct gctgtccacc      540 aacaaggccg tggtgtccct gagcaacggc gtgtccgtgc tgaccagcaa ggtgctggat      600
ctgaagaact acatcgacaa gcagctgctg cccatcgtga acaagcagag ctgctccatc     660
agcaacatcg agaccgtgat cgagttccag cagaagaaca ccggctgct ggagatcacc      720
```

| | |
|---|---|
| agggagttca gcgtgaacgc cggcgtgacc acccctgtga gcacctacat gctgaccaac | 780 |
| agcgagctgc tgtccctgat caatgacatg cccatcacca acgaccagaa aaagctgatg | 840 |
| agcaacaacg tgcagattgt gaggcagcag agctacagca tcatgagcat catcaaggaa | 900 |
| gaggtgctgg cctacgtggt gcagctgccc ctgtacggcg tgatcgatac cccttgctgg | 960 |
| aagctgcaca ccagccctct gtgtaccacc aacaccaagg agggcagcaa catctgcctg | 1020 |
| accaggaccg atagaggctg gtactgtgac aatgccggca gcgtgtcctt cttccccag | 1080 |
| gccgagacct gtaaggtgca gagcaaccgg gtgttctgtg acaccatgaa cagcctgacc | 1140 |
| ctgcccagcg aggtgaacct gtgtaacgtg acatcttca accccaagta cgactgtaag | 1200 |
| atcatgacct ccaagaccga cgtgtccagc agcgtgatta ccagcctggg cgccatcgtg | 1260 |
| tcctgctacg gcaagaccaa gtgtaccgcc agcaacaaga ccgggggat catcaagacc | 1320 |
| ttcagcaacg gctgtgacta cgtgtccaac aagggcgtgg acaccgtgtc tgtgggcaac | 1380 |
| acactgtact acgtgaataa gcaggagggc aagagcctgt acgtgaaggg cgagcccatc | 1440 |
| atcaacttct acgaccccct ggtgttccct agcgacgagt cgatgccag catcagccag | 1500 |
| gtgaacgaga gatcaacca gagcctggcc ttcatcagga gagcgacga gctgctgcac | 1560 |
| aatgtgaatg ccggcaagag caccaccaac atcatgatca ccacaatcat catcgtgatc | 1620 |
| attgtgatcc tgctgtctct gattgctgtg ggcctgctgc tgtactgtaa ggccagatcc | 1680 |
| accccgtga ccctgtccaa ggaccagctg tccggcatca caacatcgc cttctccaac | 1740 |
| tgatgaggat ccgagctc | 1758 |

<210> SEQ ID NO 18
<211> LENGTH: 1758
<212> TYPE: DNA
<213> ORGANISM: Human respiratory syncytial virus

<400> SEQUENCE: 18

| | |
|---|---|
| ggtaccgtcg acgccaccat ggagctgctg atcctgaagg ccaacgccat caccaccatc | 60 |
| ctgaccgccg tgaccttctg cttcgccagc ggccagaata tcaccgagga gttctaccag | 120 |
| agcacctgta gcgccgtgtc caagggctac ctgagcgccc tgagaaccgg ctggtacacc | 180 |
| agcgtgatca ccatcgagct gtccaacatc aaggaaaaca gtgtaacgg caccgacgcc | 240 |
| aaggtgaagc tgatcaagca ggagctggac aagtacaaga acgccgtgac cgagctgcag | 300 |
| ctgctgatgc agagcacccc cgccaccaac aacagagcca ggcgcgagct gccccggttc | 360 |
| atgaactaca ccctgaacaa cgccaagaaa accaacgtga ccctgagcaa gaagcggaag | 420 |
| cggagattcc tgggcttcct gctgggagtg ggcagcgcca tcgccagcgg agtggccgtg | 480 |
| tctaaggtgc tgcacctgga gggcgaggtg aacaagatca gagcgccct gctgtccacc | 540 |
| aacaaggccg tggtgtccct gagcaacggc gtgtccgtgc tgaccagcaa ggtgctggat | 600 |
| ctgaagaact acatcgacaa gcagctgctg cccatcgtga acaagcagag ctgctccatc | 660 |
| agcaacatcg agaccgtgat cgagttccag cagaagaaca ccggctgct ggagatcacc | 720 |
| agggagttca gcgtgaacgc cggcgtgacc accctgtga gcacctacat gctgaccaac | 780 |
| agcgagctgc tgtccctgat caatgacatg cccatcacca acgaccagaa aaagctgatg | 840 |
| agcaacaacg tgcagattgt gaggcagcag agctacagca tcatgagcat catcaaggaa | 900 |
| gaggtgctgg cctacgtggt gcagctgccc ctgtacggcg tgatcgatac cccttgctgg | 960 |
| aagctgcaca ccagccctct gtgtaccacc aacaccaagg agggcagcaa catctgcctg | 1020 |
| accaggaccg atagaggctg gtactgtgac aatgccggca gcgtgtcctt ctttccgcaa | 1080 |

```
gccgagacct gtaaggtgca gagcaaccgg gtgttctgtg acaccatgaa cagcctgacc    1140
ctgcccagcg aggtgaacct gtgtaacgtg gacatcttca accccaagta cgactgtaag    1200
atcatgacct ccaagaccga cgtgtccagc agcgtgatta ccagcctggg cgccatcgtg    1260
tcctgctacg gcaagaccaa gtgtaccgcc agcaacaaga accgggggat catcaagacc    1320
ttcagcaacg gctgtgacta cgtgtccaac aagggcgtgg acaccgtgtc tgtgggcaac    1380
acactgtact acgtgaataa gcaggagggc aagagcctgt acgtgaaggg cgagcccatc    1440
atcaacttct acgacccct ggtgttccct agcgacgagt tcgatgccag catcagccag     1500
gtgaacgaga agatcaacca gagcctggcc ttcatcagga agagcgacga gctgctgcac    1560
aatgtgaatg ccggcaagag caccaccaac atcatgatca ccacaatcat catcgtgatc    1620
attgtgatcc tgctgtctct gattgctgtg ggcctgctgc tgtactgtaa ggccagatcc    1680 accccgtga ccctgtccaa ggaccagctg tccggcatca caacatcgc cttctccaac      1740 tgatgaggat ccgagctc                                                  1758
```

```
<210> SEQ ID NO 19
<211> LENGTH: 9
<212> TYPE: PRT
<213> ORGANISM: Human respiratory syncytial virus

<400> SEQUENCE: 19

Ser Tyr Ile Gly Ser Ile Asn Asn Ile
1               5

<210> SEQ ID NO 20
<211> LENGTH: 9
<212> TYPE: PRT
<213> ORGANISM: Human respiratory syncytial virus

<400> SEQUENCE: 20

Asn Ala Ile Thr Asn Ala Lys Ile Ile
1               5
```